(12) United States Patent
Ash et al.

(10) Patent No.: US 10,702,797 B2
(45) Date of Patent: Jul. 7, 2020

(54) CARBON BLOCK/FILTRATION BED/CONICAL REACTOR WITH FLUIDIZED BED SYSTEM ALLOWING SMALL SORBENT PARTICLES TO REGENERATE FLUID DURING EXTRACORPOREAL BLOOD TREATMENT

(71) Applicant: Stephen Ash, Lafayette, IN (US)

(72) Inventors: Stephen Ash, Lafayette, IN (US); Tom Sullivan, Lafayette, IN (US); David Carr, Lafayette, IN (US)

(73) Assignee: HEMOCLEANSE TECHNOLOGY LLC, Lafayette, IN (US)

( * ) Notice: Subject to any disclaimer, the term of this patent is extended or adjusted under 35 U.S.C. 154(b) by 253 days.

(21) Appl. No.: 15/624,703

(22) Filed: Jun. 15, 2017

(65) Prior Publication Data

US 2018/0021695 A1  Jan. 25, 2018

Related U.S. Application Data

(60) Provisional application No. 62/350,189, filed on Jun. 15, 2016.

(51) Int. Cl.
*B01D 15/02* (2006.01)
*B01J 20/28* (2006.01)
(Continued)

(52) U.S. Cl.
CPC ........... *B01D 15/02* (2013.01); *A61M 1/1696* (2013.01); *A61M 1/28* (2013.01); *A61M 1/3486* (2014.02);
(Continued)

(58) Field of Classification Search
CPC .............. A61M 1/3679; A61M 1/3486; A61M 1/1696; A61M 1/28; A61M 1/1694;
(Continued)

(56) References Cited

U.S. PATENT DOCUMENTS 3,669,880 A * 6/1972 Marantz ............... A61M 1/1696
210/632
5,817,237 A  10/1998 Lee et al.
(Continued)

FOREIGN PATENT DOCUMENTS

EP  0643614 B1  12/1999
WO  2000071072 A1  11/2000
(Continued)

OTHER PUBLICATIONS

Reiter, Karl, et al. "In vitro removal of therapeutic drugs with a novel adsorbent system." Blood purification 20.4 (2002): 380-388.
(Continued)

*Primary Examiner* — David C Mellon
(74) *Attorney, Agent, or Firm* — D'Hue Law LLC; Cedric A. D'Hue

(57) ABSTRACT

Methods and devices for powdered sorbent regeneration of biologic fluids are disclosed. The present invention includes three novel methods, which may be used singly or in any combination, for constraining or immobilizing powders so that they can be perfused with a biological fluid or dialysate: a porous carbon block filter, a filtration bed of very fine powder, and a cone-shaped reactor.

17 Claims, 53 Drawing Sheets

(51) Int. Cl.

| | |
|---|---|
| *B01J 20/20* | (2006.01) |
| *B01J 20/02* | (2006.01) |
| *A61M 1/16* | (2006.01) |
| *A61M 1/28* | (2006.01) |
| *A61M 1/34* | (2006.01) |
| *A61M 1/36* | (2006.01) |

(52) U.S. Cl.
CPC ........ *A61M 1/3679* (2013.01); *B01J 20/0259* (2013.01); *B01J 20/20* (2013.01); *B01J 20/28004* (2013.01); *B01J 20/28033* (2013.01); *B01J 20/28042* (2013.01); *B01D 2215/02* (2013.01)

(58) Field of Classification Search
CPC ..... A61M 1/34; B01D 15/02; B01D 2215/02; B01J 20/28004; B01J 20/28033; B01J 20/20; B01J 20/28042; B01J 20/0259
See application file for complete search history.

(56) References Cited

U.S. PATENT DOCUMENTS

| | | | |
|---|---|---|---|
| 5,891,417 | A | 4/1999 | Bern et al. |
| 6,099,737 | A | 8/2000 | Sherman et al. |
| 6,497,675 | B1* | 12/2002 | Davankov ........... A61M 1/3472 210/433.1 |
| 6,579,460 | B1 | 6/2003 | Willis et al. |
| 6,579,496 | B1 | 6/2003 | Fausset et al. |
| 6,730,266 | B2 | 5/2004 | Matson et al. |
| 6,960,179 | B2 | 11/2005 | Gura |
| 7,033,498 | B2 | 4/2006 | Wong |
| 7,037,642 | B2 | 5/2006 | Hei |
| 2003/0114787 | A1 | 6/2003 | Gura |
| 2003/0140785 | A1* | 7/2003 | Koslow ................... C02F 1/444 95/90 |
| 2003/0196966 | A1* | 10/2003 | Hughes .................. B01D 15/00 210/758 |
| 2004/0105895 | A1 | 6/2004 | Ash |
| 2009/0124963 | A1* | 5/2009 | Hogard .................... A61M 1/16 604/30 |
| 2013/0072845 | A1* | 3/2013 | Tennison ................ A61M 1/34 604/5.04 |
| 2016/0101225 | A1* | 4/2016 | Smith .................. A61M 1/1635 210/662 |
| 2019/0022623 | A1* | 1/2019 | Tennison ........... B01J 20/28045 |

FOREIGN PATENT DOCUMENTS

| | | |
|---|---|---|
| WO | 2002043859 A2 | 11/2001 |
| WO | 2003043677 A2 | 5/2003 |
| WO | 2003051422 A2 | 6/2003 |

OTHER PUBLICATIONS

De Francisco, Angel Luis Martinez, et al. "Hemodiafiltration with online regeneration of the ultrafiltrate." Kidney International 58 (2000): S66-S71.

Yamakado, Minoru, and Michihito Ise. "Mechanism of oral absorbent AST-120 in lipid abnormalities in experimental uremic rats." Kidney International 56 (1999): S190-S192.

Winchester, James F., et al. "The next step from high-flux dialysis: application of sorbent technology." Blood purification 20.1 (2002): 81-86.

Winchester, F. J., et al. "Sorbent augmented dialysis systems." Hemodialysis Technology. vol. 137. Karger Publishers, 2002. 170-180.

Ronco, C., et al. "Use of sorbents in acute renal failure and sepsis." Contributions to nephrology 133 (2001): 180-193.

Winchester, James F., et al. "Sorbent augmented dialysis: Minor addition or major advance in therapy?." Blood purification 19.2 (2001): 255-259.

Ash, S. R., et al. "Every-other night hemodialysis with single-lumen access, plate dialyzer as blood pump, and sorbent column (SHD)." International Journal of Artificial Organs 23.8 (2000): P102-P102.

Steczko, J., et al. "Effect of hemodiabsorption and sorbent-based pheresis on amino acid levels in hepatic failure." The International journal of artificial organs 23.6 (2000): 375-388.

Ronco, Claudio, et al. "Blood flow distribution in sorbent beds: analysis of a new sorbent device for hemoperfusion." The International Journal of artificial organs 23.2 (2000): 125-130.

Ash, S. R., et al. "Changes in plasma amino acid levels in hepatic failure paients during sorbent-based dialysis and sorbent-based pheresis treatment." Hepatology. vol. 30. No. 4. Independence Square West Curtis Center, STE 300, Philadelphia, PA 19106-3399 USA: WB Saunders Co, 1999.

Peter, A. T., et al. "Push-pull sorbent-based pheresis treatment in an experimental canine endotoxemia model: preliminary report." The International journal of artificial organs 22.3 (1999): 177-188.

Hoenich, N. A. "Biocompatibility of sorbent systems." Hemodialysis Technology. vol. 137. Karger Publishers, 2002. 165-169.

Ash, Stephen R., et al. "Treatment of acetaminophen-induced hepatitis and fulminant hepatic failure with extracorporeal sorbent-based devices." Advances in renal replacement therapy 9.1 (2002): 42-53.

Ash, Stephen R., et al. "Treatment of severe tricyclic antidepressant overdose with extracorporeal sorbent detoxification." Advances in Chronic Kidney Disease 9.1 (2002): 31-41.

Ash, Stephen R. "Extracorporeal blood detoxification by sorbents in treatment of hepatic encephalopathy." Advances in renal replacement therapy 9.1 (2002): 3-18.

Winchester, James F., et al. "Sorbent hemoperfusion in end-stage renal disease: an in-depth review." Advances in Chronic Kidney Disease 9.1 (2002): 19-25.

Ash, Stephen R. "Powdered sorbent liver dialysis and pheresis in treatment of hepatic failure." Therapeutic Apheresis and Dialysis 5.5 (2001): 404-416.

Ash, Stephen R., et al. "Treatment of Systemic Inflammatory Response Syndrome by Push-Pull Powdered Sorbent Pheresis: A Phase 1 Clinical Trial." Therapeutic Apheresis and Dialysis 5.6 (2001): 497-505.

Polaschegg, N. D., et al. "Characterization of flow-dynamic pattern in a new sorbent cartridge for combined hemoperfusion-hemodialysis." Dialysis, Dialyzers and Sorbents. vol. 133. Karger Publishers, 2001. 154-165.

Kramer, L., et al. "A controlled study of sorbent suspension dialysis in chronic liver disease and hepatic encephalopathy." The International journal of artificial organs 24.7 (2001): 434-442.

Ash, Stephen R. "Biocompatibility of sorbent suspension dialysis in cirrhotic patients with hepatic encephalopathy." American Journal of Kidney Diseases 38.1 (2001): 219-220.

Soylak, M., et al. "Sorbent extraction of copper, lead, nickel and cadmium ions in dialysis concentrates before their atomic absorption spectrometric determinations." Trace elements and electrolytes 19.1 (2002): 15-19.

"Media: Sorbent Improves Kidney Dialysis", High Tech Separation News, Mar. 2000, 2 pages.

Ronco, Claudio, and James F. Winchester, eds. Dialysis, Dialyzers, and Sorbents: Where are We Going?. vol. 133. Karger Medical and Scientific Publishers, 2001, 29 pages.

Winchester, James F., et al. "History of sorbents in uremia." Dialysis, Dialyzers and Sorbents. vol. 133. Karger Publishers, 2001. 131-139.

Lameire, Norbert H., and an S. De Vriese. "Adsorption techniques and the use of sorbents." Dialysis, Dialyzers and Sorbents. vol. 133. Karger Publishers, 2001. 140-153.

Ronco, Claudio, et al. "First clinical experience with an adjunctive hemoperfusion device designed specifically to remove β2-microglobulin in hemodialysis." Blood purification 19.2 (2001): 260-263.

Winchester, James F., et al. "Rationale for combined hemoperfusion/hemodialysis in uremia." Dialysis, Dialyzers and Sorbents. vol. 133. Karger Publishers, 2001. 174-179.

Roberts et al. "The REDY® recirculating dialysis sorbent system: Dialyzers with spacer yarn." Journal of the American Society of

(56) References Cited

OTHER PUBLICATIONS

Nephrology, 33rd Annual Meeting of the American Society of Nephrology and the 2000 Renal Week, Program and Abstract Issue, Sep. 2000, 1 page.

* cited by examiner

| Funnel Reactor Design Calcs | | 10/26/2012 | | | | NOTE: SETTLING VELOCITIES AND PARTICLE S | | | |
|---|---|---|---|---|---|---|---|---|---|
| Cone+Cyl. | Cone+Cyl. | | | | | | | | |
| Free | Free | Cone Only | | 9 - 11 um | | Cone + Cylinder | | 9 - 11 um | |
| Diddle | Diddle | old | old | new | | old | old | new | |
| AnHyd | DiHyd | AnHyd | AnHyd | AnHyd | DiHyd | AnHyd | AnHyd | AnHyd | DiHyd |
| | | | | | | | | 8 | |
| | | | | | | | | 0.0004 | |
| | | | | | | | | 0.02968126 | |
| 2.92 | 2.31 | 2.92 | 2.92 | 2.92 | 2.31 | 2.92 | 2.92 | 2.92 | 2.31 |
| 1.005 | 1.005 | 1.005 | 1.005 | 1.005 | 1.005 | 1.005 | 1.005 | 1.005 | 1.005 |
| 1.0751052 | 1.0751052 | 1.075105 | 1.0751052 | 1.075105 | 1.075105 | 1.075105 | 1.075105 | 1.07510525 | 1.075105 |
| 0.0004 | 0.0003171 | 0.002132 | 0.0045484 | 0.0004 | 0.000317 | 0.002132 | 0.004548 | 0.0004 | 0.000317 |
| 8 | 6.342689 | 42.63692 | 90.968816 | 8 | 6.342689 | 42.63692 | 90.96882 | 8 | 6.342689 |
| 0.0296813 | 0.021817 | 0.068522 | 0.1000884 | 0.029681 | 0.021817 | 0.068522 | 0.100088 | 0.02968126 | 0.021817 |
| 1.7808756 | 1.3090197 | 4.111322 | 6.0053022 | 1.780876 | 1.30902 | 4.111322 | 6.005302 | 1.78087561 | 1.30902 |
| 117 | 86 | 89 | 130 | 117 | 86 | 89 | 130 | 117 | 86 |
| 9.146 | 9.146 | 5.25 | 5.25 | 9.146 | 9.146 | 5.25 | 5.25 | 9.146 | 9.146 |
| 65.698019 | 65.698019 | 21.64754 | 21.647537 | 65.69802 | 65.69802 | 21.64754 | 21.64754 | 65.6980192 | 65.69802 |
| 1.7808756 | 1.3090197 | 4.111322 | 6.0053022 | 1.780876 | 1.30902 | 4.111322 | 6.005302 | 1.78087561 | 1.30902 |
| 250 | 186 | 275 | 275 | 275 | 275 | 250 | 250 | 250 | 250 |
| 140.38038 | 142.09106 | 66.88846 | 45.792866 | 154.4184 | 210.0809 | 60.80769 | 41.62988 | 140.380383 | 190.9826 |
| 13.369288 | 13.4505 | 9.22849 | 7.63579 | 14.02183 | 16.35492 | 8.79902 | 7.28044 | 13.3692877 | 15.5938 |
| 5.2634991 | 5.2954726 | 3.633264 | 3.0062165 | 5.520404 | 6.438943 | 3.464181 | 2.866315 | 5.26349911 | 6.139292 |
| 30 | 30 | 15 | 9 | 24 | 27 | 15 | 9 | 30 | 30 |
| 0.5235988 | 0.5235988 | 0.261799 | 0.1570796 | 0.418879 | 0.471239 | 0.261799 | 0.15708 | 0.52359878 | 0.523599 |
| 0.5773503 | 0.5773503 | 0.267949 | 0.1583844 | 0.445229 | 0.509525 | 0.267949 | 0.158384 | 0.57735027 | 0.57735 |
| 5 | 5 | 5 | 5 | 5 | 5 | 5 | 5 | 5 | 5 |
| 11.578143 | 11.648475 | 17.2206 | 24.10524 | 15.74677 | 16.04916 | 16.41919 | 22.98344 | 11.5781428 | 13.50463 |
| 1.5 | 1.5 | 2 | 2 | 2 | 2 | 2 | 2 | 2 | 2 |
| 13.078143 | 13.148475 | 19.2206 | 26.10524 | 17.74677 | 18.04916 | 18.41919 | 24.98344 | 13.5781428 | 15.50463 |
| 18.078143 | 18.148475 | 24.2206 | 31.10524 | 22.74677 | 23.04916 | 23.41919 | 29.98344 | 18.5781428 | 20.50463 |
| 15.101339 | 15.182551 | 10.30029 | 8.2693277 | 15.80274 | 18.39302 | 9.870817 | 7.913978 | 15.6786888 | 17.9032 |
| 20.874841 | 20.956054 | 12.97978 | 9.8531721 | 20.25503 | 23.48827 | 12.55031 | 9.497822 | 21.4521915 | 23.6767 |
| 8.2184414 | 8.2504149 | 5.110149 | 3.8792916 | 7.974421 | 9.247351 | 4.941066 | 3.7393 | 8.44574469 | 9.321537 |
| 2062.3805 | 2086.5451 | 1068.287 | 790.59548 | 2443.172 | 3329.093 | 965.7159 | 708.1059 | 2238.27918 | 3009.283 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 2062.3805 | 2086.5451 | 1068.287 | 790.59548 | 2443.172 | 3329.093 | 965.7159 | 708.1059 | 2238.27918 | 3009.283 |
| 11.578143 | 11.648475 | 17.2206 | 24.10524 | 15.74677 | 16.04916 | 16.41919 | 22.98344 | 11.5781428 | 13.50463 |
| 541.78137 | 551.71474 | 383.853 | 367.94935 | 810.5304 | 1123.874 | 332.8044 | 318.9327 | 541.781374 | 859.7163 |
| 895.55193 | 905.21011 | 416.6377 | 268.53463 | 980.6743 | 1328.513 | 382.6186 | 245.9515 | 965.337921 | 1258.697 |
| 1676.3623 | 1698.6856 | 950.506 | 735.87869 | 2140.928 | 2927.083 | 852.4537 | 655.5993 | 1839.171 | 2559.739 |
| 386.01821 | 387.8593 | 117.7813 | 54.71679 | 302.2446 | 402.0099 | 113.2623 | 52.50661 | 399.108179 | 449.5434 |
| 0.8 | 0.8 | 0.8 | 0.8 | 0.8 | 0.8 | 0.8 | 0.8 | 0.8 | 0.8 |
| 1.7337004 | 2.3729666 | 1.116954 | 1.0703981 | 2.357907 | 3.269452 | 1.064974 | 1.020585 | 1.7337004 | 2.731092 |

Orange cells indicate limiting factor

Figure 46A

| | | | | | | | | | | | |
|---|---|---|---|---|---|---|---|---|---|---|---|
| ZES ARE AROUND -2 SIGMA FROM MEAN. | | | | | | | | | | | |
| | | | | | | | | | | | |
| Units: cgs | | | | | | | | | | | |
| | | | | | | | | | | | |
| (all units cm, min, ml, cc, cm^2, cm^3) | | | | Unless otherwise indicated | | | | | | | |
| Particle sizes that are known - um | | | | | | | | | | | |
| radius of known particle, cm | | | | | | | | | | | |
| v in cm/s | | | EXPERIMENTAL RESULT | | | | | | | | |
| Particle density | | | | | | | | | | | |
| 0.9% NaCl density | | | | | | | | | | | |
| k = Sqrt (8g / (3C) ) calculated | | | | | | | | | | | |
| Calculated particle radius | | | | | | | | | | | |
| Entered | Calculated | Particle diameter in microns | | | | | | | | | |
| Calculated settling velocity, cm/s | | | | | | | | | | | |
| Calculated settling velocity, cm/min | | | | | | | | | | | |
| Q at 21.5 cm height of cloud | | | EXPERIMENTAL RESULT | | | | | | | | |
| Dia at 21.5 cm height of cloud | | | EXPERIMENTAL RESULT | | | | | | | | |
| Area | | | EXPERIMENTAL RESULT | | | | | | | | |
| Linear v | | | EXPERIMENTAL RESULT | | | | | | | | |
| Design max Q | | | 130 is too high, but probably closest | | | | | | | | |
| Required area | | | These are limits in tube, not cone results. | | | | | | | | |
| Required diameter | | This is CLOUD height, also Diameter of Cone Plus Cylinder | | | | | | | | | |
| Diameter in INCHES | | | | | | | | | | | |
| Cone Angle, deviation from vertical, degrees | | | | | | | | | | | |

Figure 46B1

| | | Typical Cone Angles From Vertical | | |
|---|---|---|---|---|
| Radians | | | | |
| Increase in Radius / Increase in Height | | | | |
| Required headspace | Note: Test headspace of 6 cm found not quite adequate. | | | |
| Cloud top height | | | | |
| Cone top margin | | | | |
| Required Cone Height | | 7 Imhoff Cone | | |
| Total Height | | | | |
| Required Cylinder Diameter | | | | |
| Cone Top Diameter With HeadSpace | | 20.5 Narrow Powder Funnel #2 | | |
| Cone Top in INCHES | | 30 Typical Liquid Funnel #5 | | |
| Cone Volume | | Estimate of Cloud Volume | | EXPERIMENTAL RESULT |
| Porous Plastic Diameter | | 25 g | load | |
| Height from theoretical cone point to porous plastic | | 8.3 cm | height | |
| Inlet volume | | 5.25 cm | diameter | |
| Active volume, excluding porous plastic, fittings, etc. | | 179.6746 cm^3 | volume | |
| Height between top of cloud and porous plastic | | 50 g | desired load | |
| Cloud Volume | | 359.3491 cm^3 | Required dense cloud volume | |
| Cylindrical Headspace Volume | | | | |
| Total Volume for Cylinder on Top of Cone | | | | |
| Volume savings due to use of cone plus cylinder instead of straight cone. | | | | |
| Dwell Time Fudge Factor | | | | |
| Calculated Dwell Time | | | | |

Figure 46B2

| h | r | v | | |
|---|---|---|---|---|
| 4.918 | 3.125 | 50.29412 | Funnel | cone |
| 1 | 3.125 | 10.22654 | Intermedia | cone |
| -0.5 | 3.125 | -5.11327 | Headspac | cylinder |
| 2 | 3.25 | 66.36614 | carbon | area |
| 9.875 | 1.5 | 69.80226 | | |
| -4.9375 | 1.25 | -24.2369 | | |
| 9.875 | 0.625 | 12.11845 | | |
| | | 179.4573 | Sum | cuin |
| | | 2940.779 | | cc |
| | | 5.08 | Headspace cm | |

Figure 47

CARBON BLOCK/FILTRATION BED/CONICAL REACTOR WITH FLUIDIZED BED SYSTEM ALLOWING SMALL SORBENT PARTICLES TO REGENERATE FLUID DURING EXTRACORPOREAL BLOOD TREATMENT

CROSS REFERENCE

This application is a U.S. non-provisional patent application which claims the benefit of U.S. provisional patent application Ser. No. 62/350,189, filed Jun. 15, 2016, the disclosure of which is expressly incorporated by reference.

FIELD

Methods and devices for powdered sorbent regeneration of biologic fluids.

BACKGROUND

Toxins in the body (human or animal) may be of either external origin or a result of physiologic processes. Where renal or hepatic failure or insufficiency hampers normal metabolism or excretion of waste products or toxins, serious illness or death results, even though the waste products or toxins may be normally present in the body in non-toxic concentrations.

Although antidotes sometimes may be employed for specific toxins, at the present time, treatments for toxins in the body typically involve either replacement of body fluids (e.g., blood or plasma replacement/transfusion) or purification of the blood by external means. An example of such blood purification is the fairly common process of renal dialysis (either standard or peritoneal). In the most common methods of dialysis, highly pure water on one side of a membrane (e.g., the peritoneum or an artificial membrane in a dialyzer) is used to create osmotic transport of toxins from the blood to the water. The water, after passing once through the dialyzer, is discharged to the drain. In a standard dialysis system, the patient's blood is pumped through the dialyzer, while the highly pure water, combined with essential electrolytes, is passed through the dialyzer on the opposite side of the dialyzer membrane.

Where a large supply of highly pure water is not available or undesirable, it is possible to re-circulate the dialysis water by purifying it. Such purification is accomplished with active carbon, often in conjunction with ion-exchange media. The Redy™ 2000 and Allient™ dialysis machines are examples of such a system. In these machines, the dialysate is purified (regenerated) by layers of granular carbon and ion exchange resins in a single cartridge (the Sorb™ column). In principle, multiple cartridges, each containing a single substance, could be connected in series to achieve the same result. The active carbon adsorbs various toxins. Hemodialysis circuits are typically clean, but not sterile. The Sorb column is also clean, but not sterile and the carbon layer actually removed many bacteria. Since the dialysis treatments of the Redy and Allient machines were of limited duration, up to 8 hours, recirculating dialysate through the Sorb column did not result in significant growth of bacteria in the dialysate.

Another method of blood purification is hemoperfusion, where the patient's blood is pumped directly through a bed of granular active carbon. The active carbon adsorbs toxins directly from the blood. This method is rarely used due to thrombogenicity and other issues.

In other, typically more recent and experimental extracorporeal treatments, plasma is separated from the patient's blood by a filter or centrifuge. The plasma is then treated by contact with purification media such as active carbon and/or ion exchange media, which adsorb toxins from the plasma.

Of interest here is the role of active carbon. Carbon is a natural adsorbent for many organic compounds including toxins. Thermal, steam, or chemical treatment of carbon can create a highly porous form of carbon with very high surface area per unit weight, typically on the order of 100 to 2000 square meters per gram. Such treated carbon is called, variously, activated carbon, activated charcoal, active carbon, active charcoal, etc. The term "active carbon" is used herein. The pore structure of active carbon is commonly classified according to size as macropores, mesopores and micropores. See FIG. 1. It is the pore structure which gives active carbon its high surface area per unit weight, and thus its "activity" or affinity which enables it to adsorb significant and useful quantities of toxins. Toxins thus adsorbed are thus, obviously, removed from the patient.

Pores typically become finer as one penetrates deeper into a particle of carbon. The larger, outer, macropores lead to the smaller mesopores (variously defined as being 2-100 μm), which in turn, lead to the yet smaller micropores (variously defined as <2-10 μm).

Since adsorption is a physical, equilibrium-governed process, particles of carbon will rapidly and immediately adsorb a small initial charge of toxin, but then adsorption will cease unless the toxin diffuses into the pore structure of the carbon particle where the toxin is able to reach areas of low toxin concentration. Hence, diffusion of the toxin into the interior pore structure is critical as most of the available surface area of the carbon is in the pore structure, particularly the mesopores and micropores. This being the case, highly microporous carbons are typically selected for small molecular weight toxins and highly mesoporous carbons are typically selected for larger molecular weight toxins. Where mixes of toxins are encountered, a carbon with a mix of mesopores and micropores will be selected.

Many processes govern diffusion of molecules into the pores. In generalhowever, the longer the pore, the more time it will take for target molecules to reach the inner portions of the pores. The result is that the larger the particle of active carbon, the slower the diffusion of target (toxin) molecules into the pores and the slower the adsorption kinetics, other parameters being equal.

One obvious method of reducing the mean path length of the pore structure is to use smaller particles of carbon. Whereas industrial purification processes typically use granular carbon and treatment times of hours, carbon given as general oral antidote for poisoning is finely powdered.

FIG. 2 compares the effects of particle size on adsorption kinetics. In FIG. 2, reaction time was limited. During this time, the same granules which adsorbed little bilirubin (a typical toxin) adsorbed much more bilirubin when powdered. The very finely powdered oral adsorbent used as a general antidote to accidental poisoning (Norit Powder) adsorbed very much more bilirubin.

This phenomenon, at its core, is simple: Smaller particles have shorter mean pore length so they adsorb toxins more quickly.

When active carbon is used as an oral sorbent, or when employed in a suspension, very fine particles rapidly adsorb toxins and are thus much more effective than larger particles where time of contact between the active carbon and the solution containing the toxins is limited.

FIG. 3 is presented as an example of a use of fine particles of active carbon as an adsorbent to detoxify patient blood. The diagram shows an extracorporeal system using a suspension of finely pulverized (<10 μm, typical) active carbon. Blood is pumped from the patient through a filter, which may be a plasma filter, dialyzer or similar device. The filtrate (e.g., dialysate, albumin, or patient plasma) is passed through a reactor which mixes fine active carbon particles with the treated fluid, separates the treated fluid from the carbon, and returns the treated fluid either to the dialyzer or directly to the patient. This type of system is relatively fast and is therapeutically effective, but is costly and complex due to the need to separate very fine carbon particles from the exiting fluid.

It is important to note that in most cases, fluid volume is a critical limitation. There are two such limitations. First, to provide adequate treatment, i.e., to remove a clinically significant amount of toxin from the patient, a large volume of the patient's blood must be treated in a reasonable amount of time. Since treated blood is returned to the patient immediately, toxin removal follows an exponential decay curve. Secondary processes include diffusion of toxins from the interstitial fluid to the blood and from cells to the interstitial fluid and blood. FIG. 4 shows theoretical toxin removal by a perfect adsorbent over time for various plasma flow rates for a particular system which used a plasmafilter and an active carbon sorbent to treat rat plasma in a manner similar to that of FIG. 3, but which used solid block carbon.

As may be seen, improvements in plasma flow rate (Q) produce improvements in toxin clearance. The reason for this is that over a given period of time, higher flow rates treat more of the patient's blood and thus remove more toxin.

While the first volume limitation mandates a high treated fluid volume, safety considerations dictate that only a limited amount of blood may be withdrawn from a patient at any one time. Extracorporeal systems necessarily withdraw blood from the patient and present not only a short-term loss to the patient, but also present a hazard of long-term blood loss in the event of machine failure or clotting in the system. Hence, there is a second fluid volume limitation in that only a minimal amount blood is available for treatment at any one time.

In a particular practical extracorporeal system treating plasma, for example, plasma is presented to the active carbon for only seven minutes. Rapid adsorption kinetics is thus a necessity. Even in the case of regenerating aqueous dialysate, there may be practical fluid volume limitations, particularly when it is necessary to retain patient nutrients and desirable blood components which would otherwise be lost in standard "down the drain" hemodialysis.

As noted above, small particles may be used in a stirred suspension, but the apparatus is complex and costly. Packed columns would, at first, appear to be a reasonable alternative. Unfortunately, small particles present substantial hydraulic resistance when packed into a column. Making a column shorter and of increased cross-sectional area produces benefits, but this method has severe limitations due to problems with channeling in the charcoal bed, lack of even flow distribution and mechanical constraints. The problem is greatly compounded when the active carbon must treat proteinaceous fluids such as albumin or plasma which are viscous. The matter is more severe yet when column outlet frits (filters) must pass very large molecular weight substances found in plasma such as albumin and globulins. Carbon particle fines in the outlet frit may reduce the effective frit pore size to such small dimensions as to produce molecular sieving, a phenomenon which the inventors have observed. In certain cases, using high pressure can overcome some of these limitations, but this is costly, particularly where biohazard considerations dictate disposable wetted pump components.

We are thus left with the quandary that small particles give therapeutically useful fast sorption kinetics, while large particles may be readily contained in inexpensive columns which treat fluid at reasonable pressures. It is the object of the present invention to resolve this conundrum.

In general principle, an approach to providing a short mean diffusion path length in the pore structure of the carbon, while using large, easily-constrained carbon pieces, is to use large carbon pieces which are "geometrically complex" and which have a fine structure. A sponge roughly illustrates the concept. The sponge is a large object, but it has relatively small features. If the geometrically complex carbon is porous and allows the treated fluid to pass through it, then the useful fast reaction kinetics of small particles is provided by the small features. The overall particle is large and easily constrained in a reactor.

It is important to clarify some terminology at this point. Active carbon has a large surface area which is created by the pore structure. But we may define, "gross surface area," as that surface which is presented by the outer surface outside of the pore structure. For example, generally spherical carbon particles of any size would have gross surface area of $4\pi r^2$. Obviously, the distinction between "gross surface" and the beginnings of the pores is fuzzy, but this does not invalidate the usefulness of the concept.

We desire pieces of carbon which have high gross surface area and fine features which give a short mean pore path length.

One form of geometrically complex active carbon that has been developed is fractal spherical carbon developed by Vladimir Nikolaev as shown in FIG. 5 which is used for hemoperfusion.

This carbon has performed well in specific applications, but is costly, not readily available and the spheres must be confined in a column by a frits or other means. Since the particles are on the order of 100 μm, pressure drop through a column, while not excessive, is significant, especially for plasma treatments.

SUMMARY

Extracorporeal blood treatments remove blood from a patient, purify it in some manner and return the blood to the patient. Standard hemodialysis is an example of such treatments. Some extracorporeal blood treatments use active carbon sorbents to adsorb various toxins from the blood (directly or indirectly) and it is this type of treatment to which the present invention applies. While in hemoperfusion, the carbon contacts the blood directly, more typically, patient plasma or another circulating fluid contacts the active carbon.

In order for an extracorporeal blood treatment to be effective in removing toxins from a patient's body, a substantial volume of fluid must be treated. At the same time, safety and physiological constraints limit the amount of blood that can be removed from the patient at any one time. Other constraints also typically limit the amount of fluid available for sorption treatment at any one time. The natural consequence of these two simultaneous limitations is that a treatment device has only a few minutes in which to adsorb the toxins from the treated fluid. As a result, sorption kinetics must be sufficiently rapid or the device will be ineffective.

It is in the nature of active carbon sorbents that fluid containing toxins to be adsorbed (and thus removed from the patient) must diffuse into the pore structure of the carbon, a process which takes a certain amount of time. Given a certain otherwise same set of diffusion conditions, and especially for larger molecular weight toxins, it is obvious that the shorter the mean path length of the pore structure, the more rapidly the active sites in the carbon will be utilized and thus the more rapidly the toxin will be adsorbed. It is for this reason that commonly used large granules of active carbon have sorption kinetics which are too slow for effective and efficient extracorporeal use, especially for toxins of more than a few hundred Daltons molecular weight.

One obvious way to achieve a short mean pore path length is to use small particles of carbon as opposed to the larger granules in common use. However, active carbon in the form of small particles is difficult to use. If used in a stirred suspension, separation of the treated fluid from the suspension after treatment is difficult. If the small particles are packed into a column, pressures are excessive, particularly with proteinaceous fluids. The common opinion of chemical engineers is that it is impossible to construct a column with even flow distribution and modest pressure drop from particles smaller than 50 microns, and even that particle size works in a column only if the particles are nearly perfectly spherical.

In general principle, an approach to providing a short mean diffusion path length in the pore structure of the carbon, while using large, easily-constrained carbon pieces, is to use large carbon pieces which are "geometrically complex" and which have a fine structure. A sponge roughly illustrates the concept. The sponge is a large object, but it has relatively small features. If the geometrically complex carbon is porous and allows the treated fluid to pass through it, then the useful fast reaction kinetics of small particles is provided by the small features. The overall particle is large and easily constrained in a reactor. We desire very small pieces of carbon which have high external surface area and fine features which give a short mean pore path length, but which are constrained or immobilized in a manner to allow perfusion of fluids around every particle. Commonly available commercial drinking water filters made of porous powdered carbon extruded with fine plastic fibers have this desirable complex geometry, being constructed of powders ranging from 1 to 20 microns in size and having short mean pore path length. The fluid pathways in such carbon blocks may range from a fraction of a micron to five microns, and thus the surface acts as a very uniform filter preventing passage of larger particles. Thus, the carbon block would not be suitable for blood perfusion, but would be suitable for treating other biological fluids such as plasma or peritoneal fluid or dialysate which is a salt solution which accumulates toxins from blood by passage across semipermeable membranes. The filtering surface of the carbon block is also of benefit for restraining very small particles of other sorbents besides charcoal.

The present invention includes three novel methods, which may be used singly or in any combination, for constraining or immobilizing powders so that they can be perfused with a biological fluid or dialysate:

A porous carbon block (CB) filter (such as is typically used as drinking water filters) is used to regenerate fluid during extracorporeal blood treatments. Surprisingly, we know of no medical device that currently includes a carbon block for removing toxins, either from any dialysate or any biological fluid.

A filtration bed (FB) of very fine powder which is created by passing a fluid containing suspended particles through the filtering surface of the carbon block (or a similar filter) and then holding the particles in fixed position by continued fluid flow. This filtration bed allows particles of a few microns diameter to be used for perfusion and depuration like a column, but breaking the above described "50 micron" rule and providing even flow distribution within the layer of very small particles.

A cone-shaped reactor (CR) designed to suspend particles in a "fluidized bed" in which an upward flow of dialysate or biological fluid exactly equals the sedimentation rate of fine particles. The particles then move around within the suspension of fluid, mixing evenly with all the passing fluid. The conical shape provides a continuously decreasing upward velocity of fluid flow, to create one level where the majority of powdered particles do not pass upwards. Those particles which are smaller than most in the suspension pass upward from the CR and form the FB around the CB.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 46A—Spreadsheet, First worksheet (part 1 of 2): The output for Funnel Reactor Design Calculations FIG. 46B1—Spreadsheet, First worksheet (part 2 of 2; top): The output for Funnel Reactor Design Calculations FIG. 46B2—Spreadsheet, First worksheet (part 2 of 2; bottom): The output for Funnel Reactor Design Calculations FIG. 47—Spreadsheet, Second Worksheet: The summary of the Funnel Reactor Design calculations Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

Figure 45:
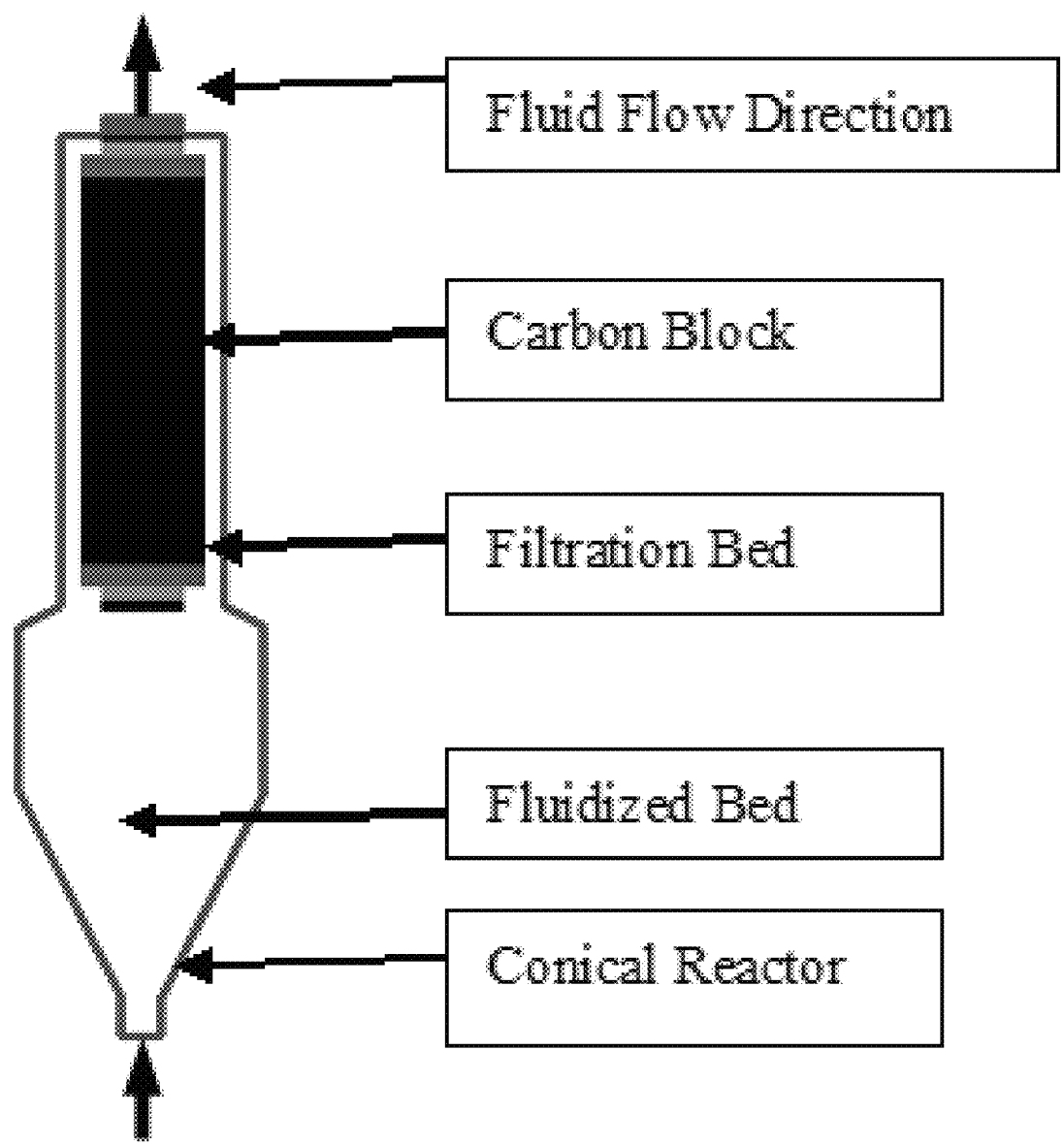
FIG. 45—The Combined system

We envision the combined system to be arranged as in FIG. 45, so that particles which are too small to stay within the fluidized bed travel upwards to form the filtration bed around the carbon block. When fluid flow is stopped, the particles falling off of the carbon block will return to the fluidized bed.

Section A: Carbon Block for Toxin Removal from Biological Fluids

The use of porous "solid block" active carbon results in the rapid sorption kinetics necessary for effective and efficient toxin removal, coupled with other desirable features such as easy constraint of the carbon, mechanical simplicity and low cost.

Laboratory data show that porous active carbon block is generally equal to or superior to alternative sorption systems using active carbon.

Additionally, the author has a developed novel method of priming a reactor using the above invention which excludes harmful air and permits rapid and easy insertion of such a reactor into an existing treatment system. The method consists of evacuating the reactor to a high vacuum. When the user fills the reactor from a standard IV bag, the reactor is immediately ready to use without otherwise difficult to remove entrained air.

The invention consists of a novel application of an existing product to the problem at hand. The existing product is the common solid-block carbon water filter cartridge. The novel application is to apply the solid block carbon filter to the field of extracorporeal blood treatments, including, but not limited to:

Hemoperfusion—Direct adsorption of toxins from blood

Plasma treatment—adsorption of toxins from patient plasma

Dialysate purification and regeneration
  Single pass purification of dialysate prior to entering the dialyzer
  Recirculating dialysate purification—the dialysate fluid is purified after acquiring toxins across the dialysis membrane and thence sent back to the dialyzer after the carbon has adsorbed the toxins.
  Recirculating dialysate purification where the solid block carbon purifies the dialysate from tap or other water prior to beginning of treatment Peritoneal dialysate purification and regeneration
  Single pass purification of dialysate prior to entering the dialyzer
  Recirculating dialysate purification—the dialysate is purified after acquiring toxins across the peritoneum and thence sent back to the peritoneum after the carbon has adsorbed the toxins. In this application, an added value of the carbon block is that it will filter white cells and fibrin material from the peritoneal fluid, thus keeping the fluid very clear on outflow from the peritoneum. This may diminish the tendency for obstruction of inflow and outflow catheters.
  Recirculating dialysate purification where the solid block carbon purifies the dialysate from tap or other water prior to beginning of treatment Purification of other circulating fluids such as albumin or plasma when used in a dialysis or plasmapheresis circuit or other extracorporeal blood treatment device.

Figure 1:
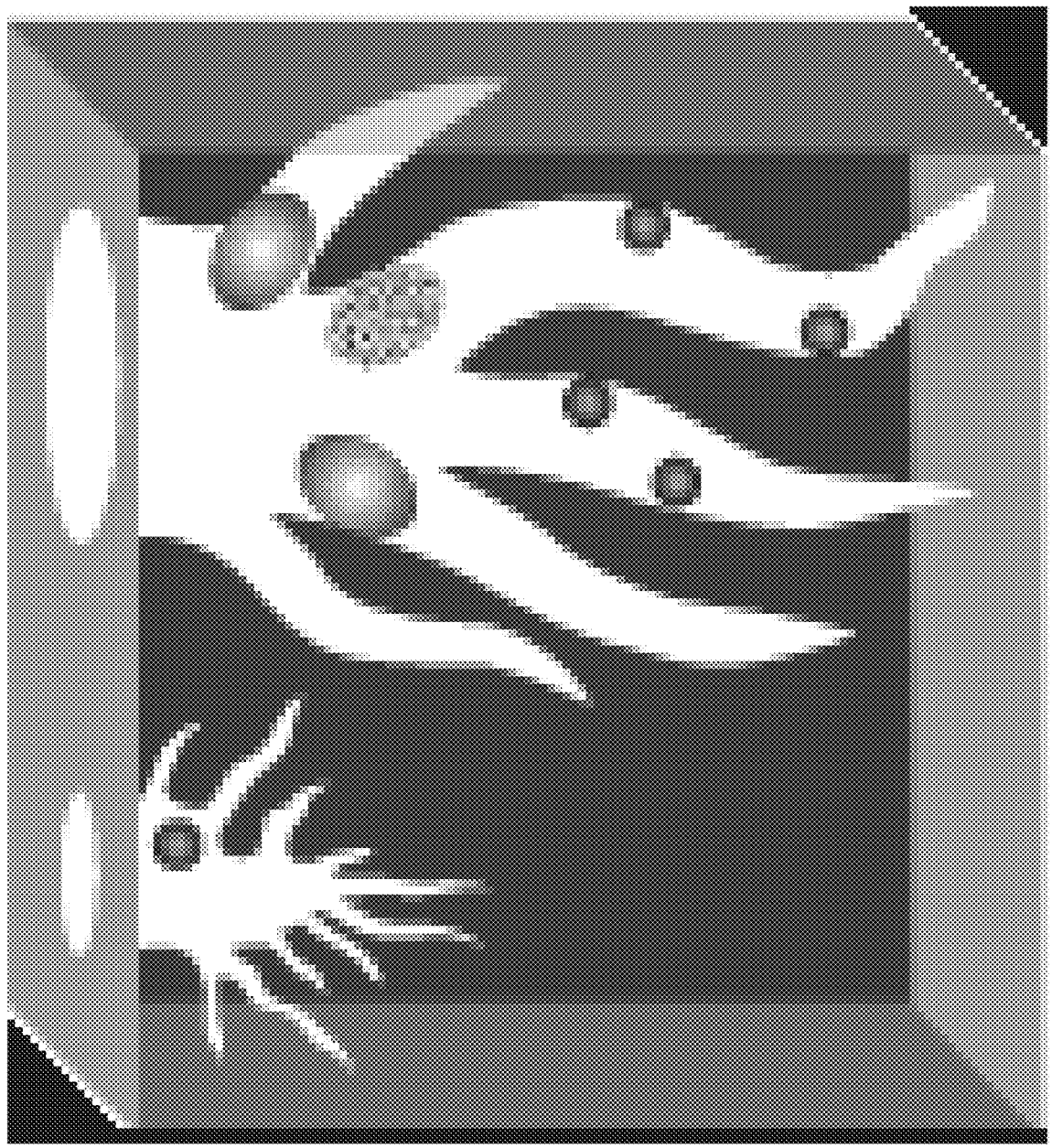
FIG. 1—Typical Active Carbon Pore Structure Schematic
FIG. 2—Effects of Particle Size on Sorption Kinetics
FIG. 3—Extracorporeal Blood Treatment System Using Suspension of Active Carbon
FIG. 4—Theoretical Treatment Efficacy as a Function of Plasma Flow Rate
FIG. 5—Fractal Carbon Spheres
FIG. 6A—Example of a Solid Block Active Carbon Filter
FIG. 6B—Example of a Solid Block Active Carbon Filter
FIG. 7—Solid Carbon Block Flow and Holder/Reactor
FIG. 8—Example Insertion Point of a Solid Block Carbon Reactor to an Existing Disposable Kit for Hemodialysis (B Braun Diapact CRRT Machine) (From Diapact™ manual)
FIG. 9—SBR Disposable
FIG. 10—Auxiliary Priming Disposable
FIG. 11A—Comparison of Biologic DT Circulating Active Carbon Suspension with Solid Block Active Carbon Reactor Using Aqueous Dialysate
FIG. 11B—Comparison of Biologic DT Circulating Active Carbon Suspension with Solid Block Active Carbon Reactor Using Aqueous Dialysate
FIG. 12A—Performance Comparisons Between Solid Block Carbon and Other Carbon Forms
FIG. 12B—Performance Comparisons Between Solid Block Carbon and Other Carbon Forms
FIG. 13—Results of Gamma Irradiation of Carbon Blocks
FIG. 14—Conventional CVVHD
FIG. 15—Modification of Conventional CVVHD Using a Carbon Block
FIG. 16—Combination of Conventional and Carbon Block Methods with Infusate
FIG. 17—Addition of Effluent Pump and Reservoir
FIG. 18A—Calcium Phosphate Powder Without Fluid Flow
FIG. 18B—Calcium Phosphate Powder With Fluid Flow
FIG. 19A—Differences between a standard column and the carbon block/filtration bed approach
FIG. 19B—Surfactants in the fluid may possibly be included in the fluid to aid in meeting particle size, fluid density and viscosity, other fluid characteristics, fluid/particle affinity, surface tension, etc.
Figure 2:
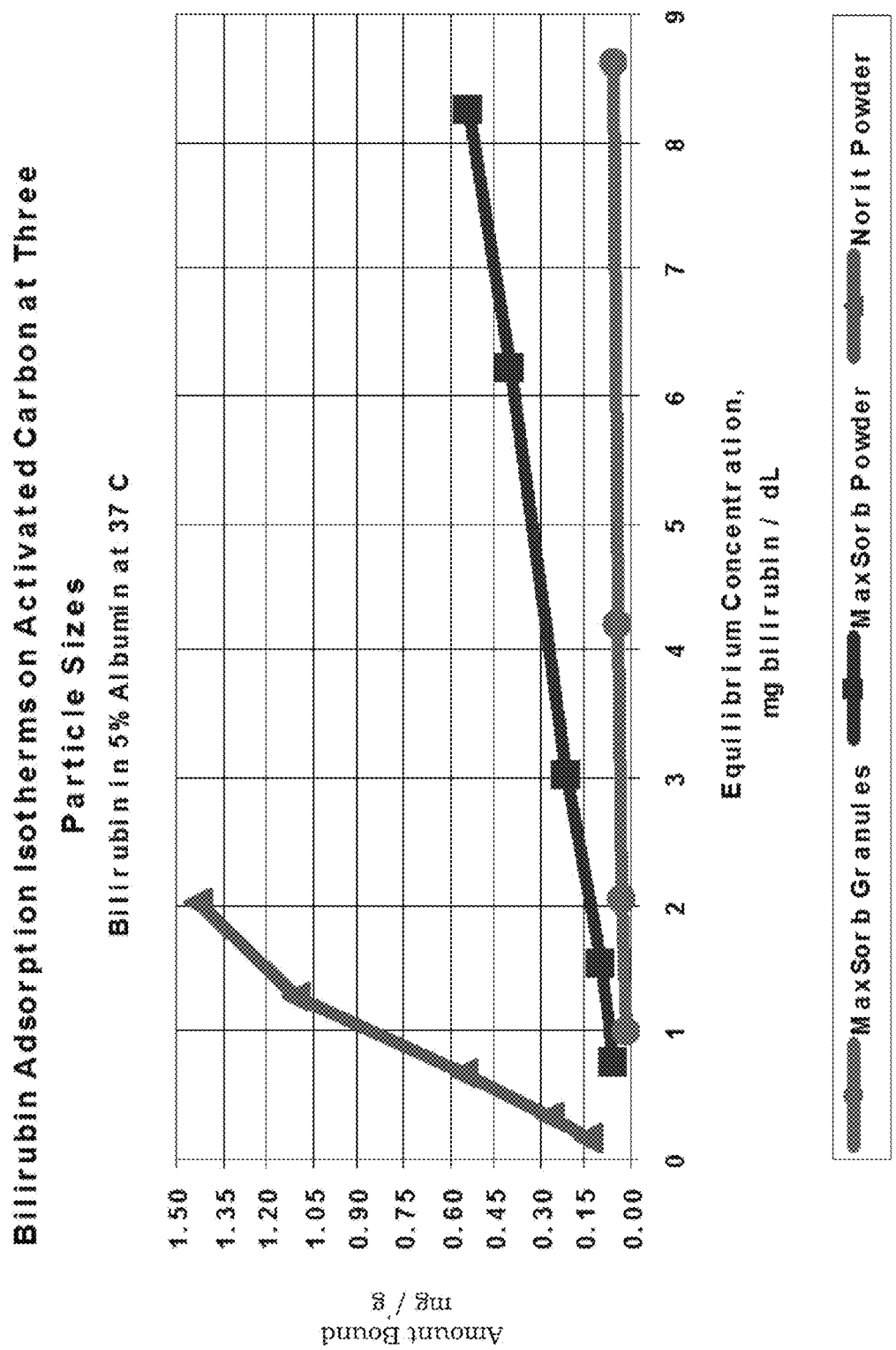
Figure 3:
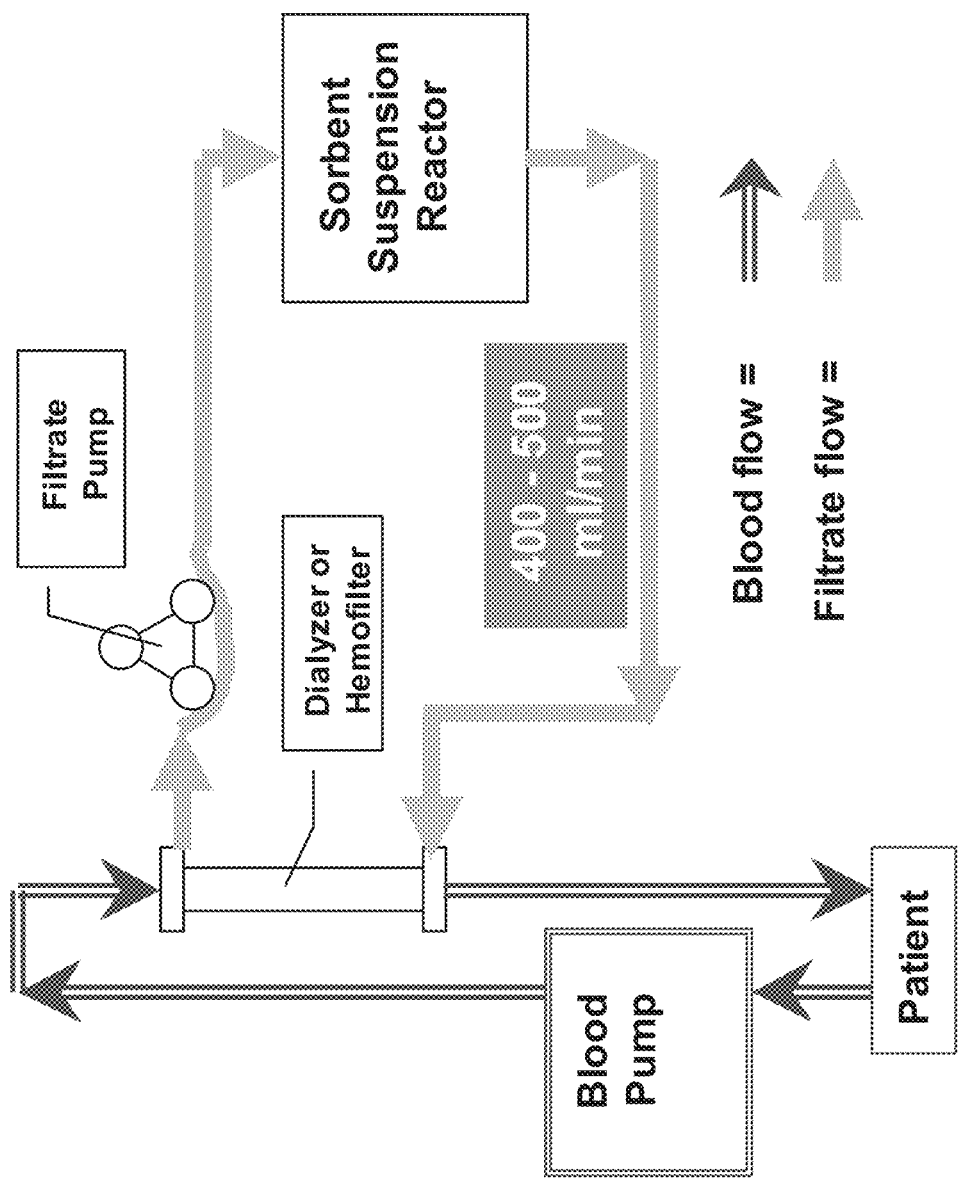
Figure 4:
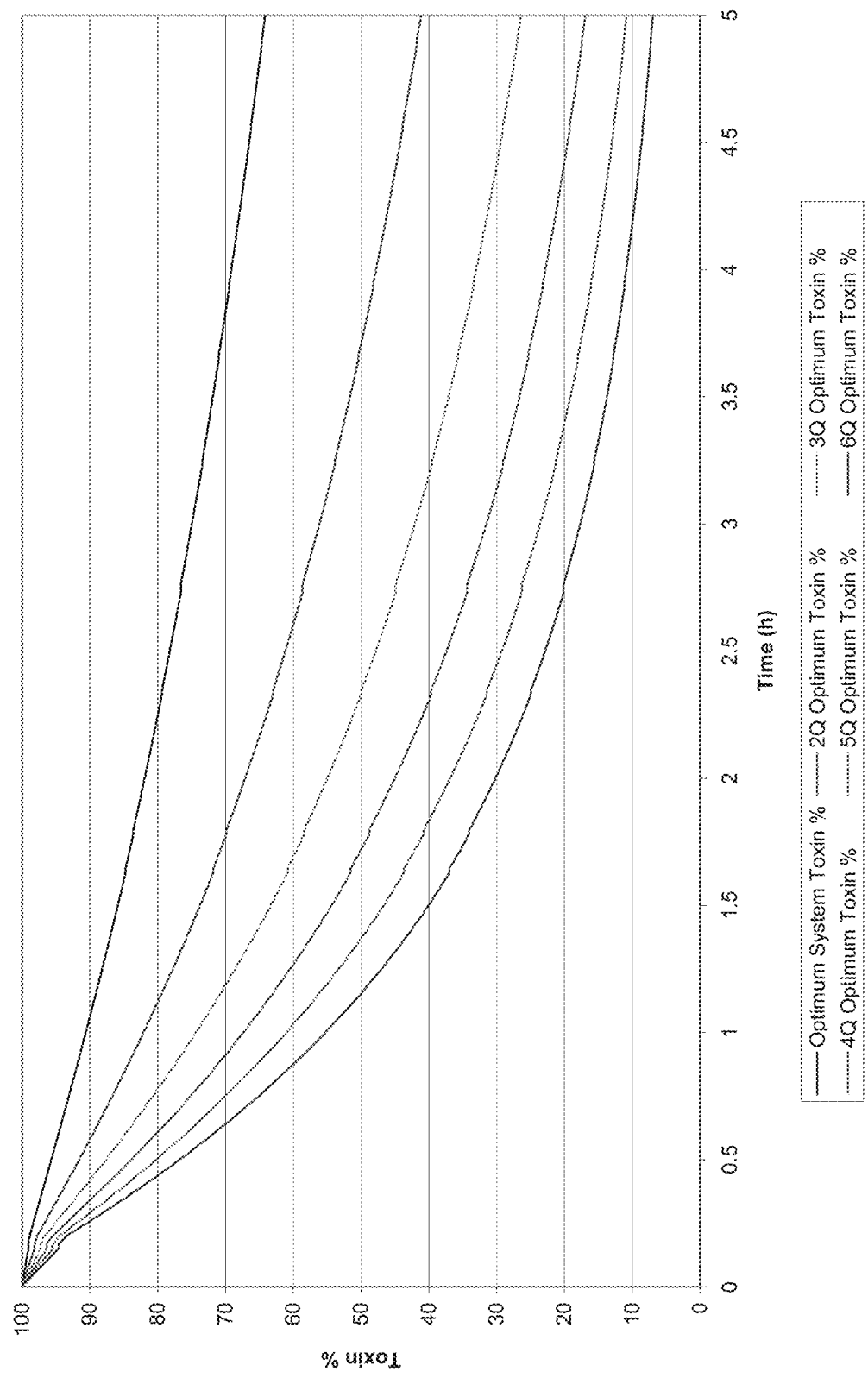
Figure 5:
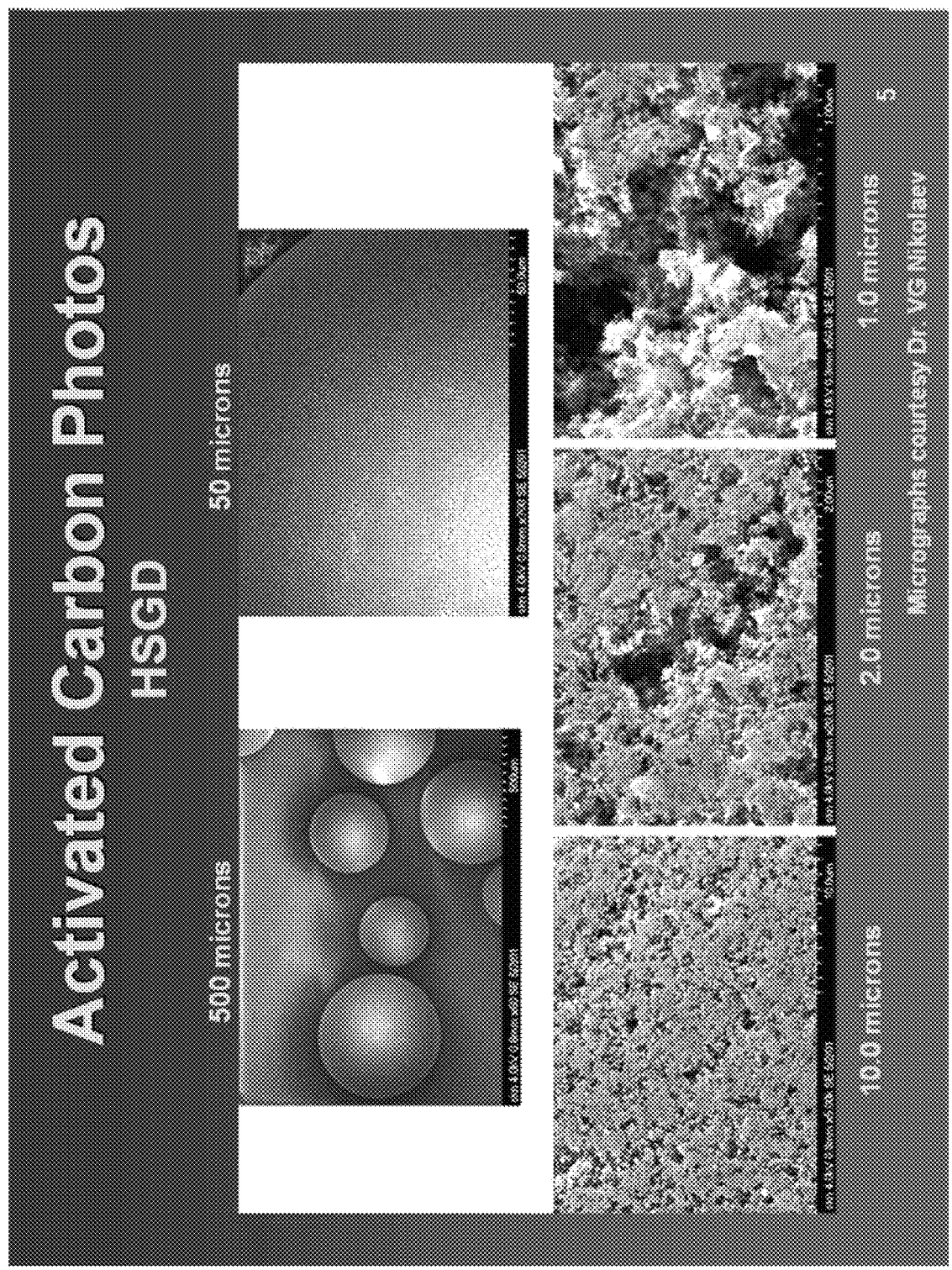
Figures 6A, 6B:
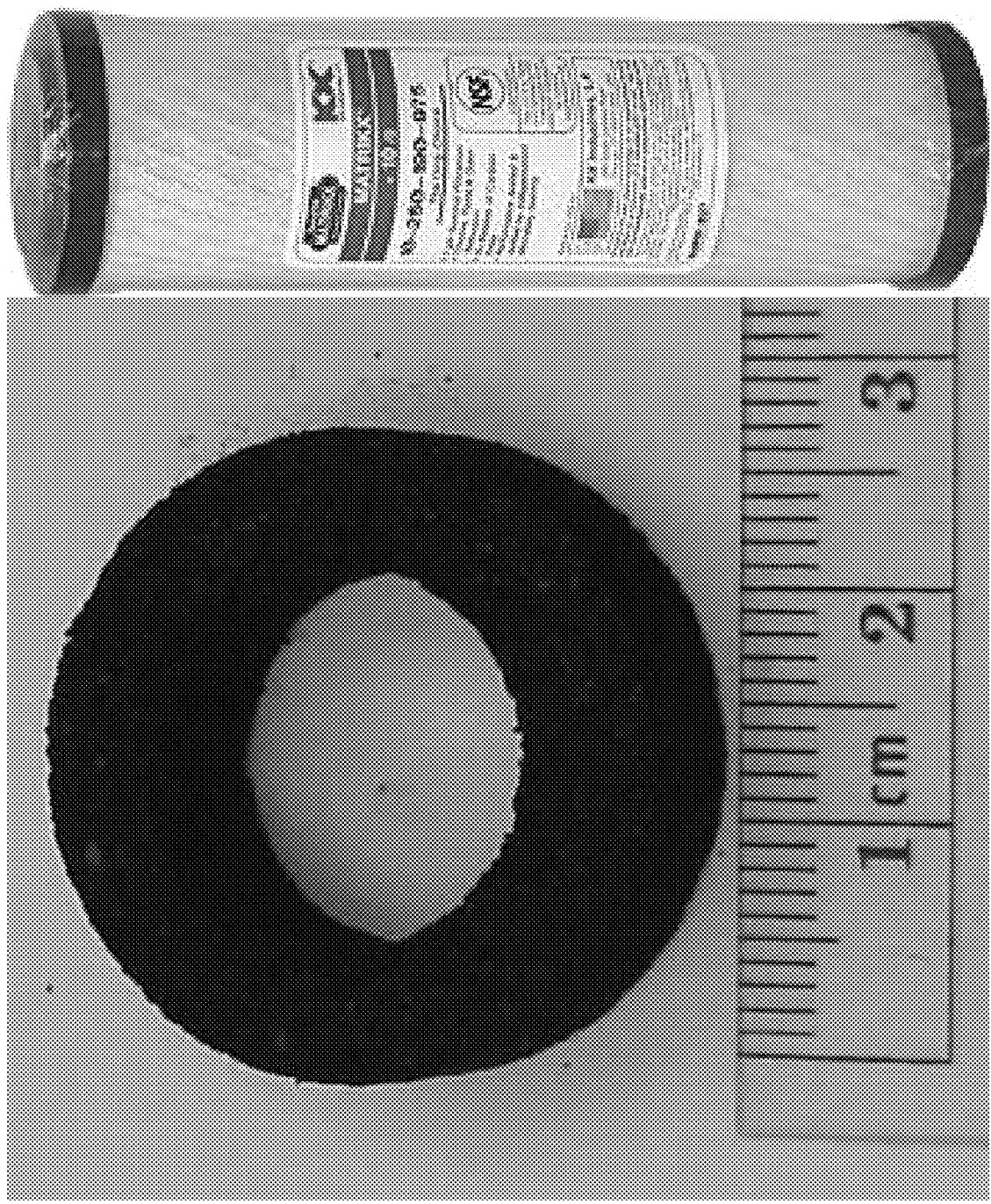

Multiple vendors produce solid block carbon filters for both commercial and consumer use. See FIGS. 6A and 6B for examples, including the KX-5carbon block from Matrixx, Inc.

These solid block filters are solid only in the sense that the active carbon is a single piece; they are actually porous with nominal mean pore sizes typically in the 0.5 to 10 µm range. They are made by taking pulverized active carbon, mixing it with a binder and extruding or otherwise processing it into a hollow cylinder. Fluid passes through the block, typically from the outer perimeter of the cylinder, through the active carbon matrix and thence to the center hole. Although this flow arrangement is generally satisfactory and results in minimal flow resistance, there is no reason why other geometries cannot be used to produce other combinations of hydraulic characteristics and column adsorption characteristics. One example of an alternate geometry would be a solid cylinder used in a manner similar to a classic packed column where flow is from top to bottom.

It should be noted that it is the bare carbon block that is of interest here. Other accessory components of a typical cartridge such as end caps, sealing rings, preliminary filter wrapping, etc., may or may not be useful in specific applications and such may be used or omitted as desired.

A very common use for these filters is for whole-house residential drinking water filtration. They remove sediment and other particulates (such as sand from a well) by virtue of their porous structure. They also adsorb undesirable taste and odor causing substances by virtue of the active carbon which makes up the porous structure. Some are also rated to remove certain toxins such as lead or chlorine. Rated flow can be in the 11 gpm range. Some carbons are also capable of chemisorption as well as the more usual van der Waals sorption.

Although the sorbent capabilities are of primary interest here, in some applications, the filtration function may be useful as well.

Figure 7:
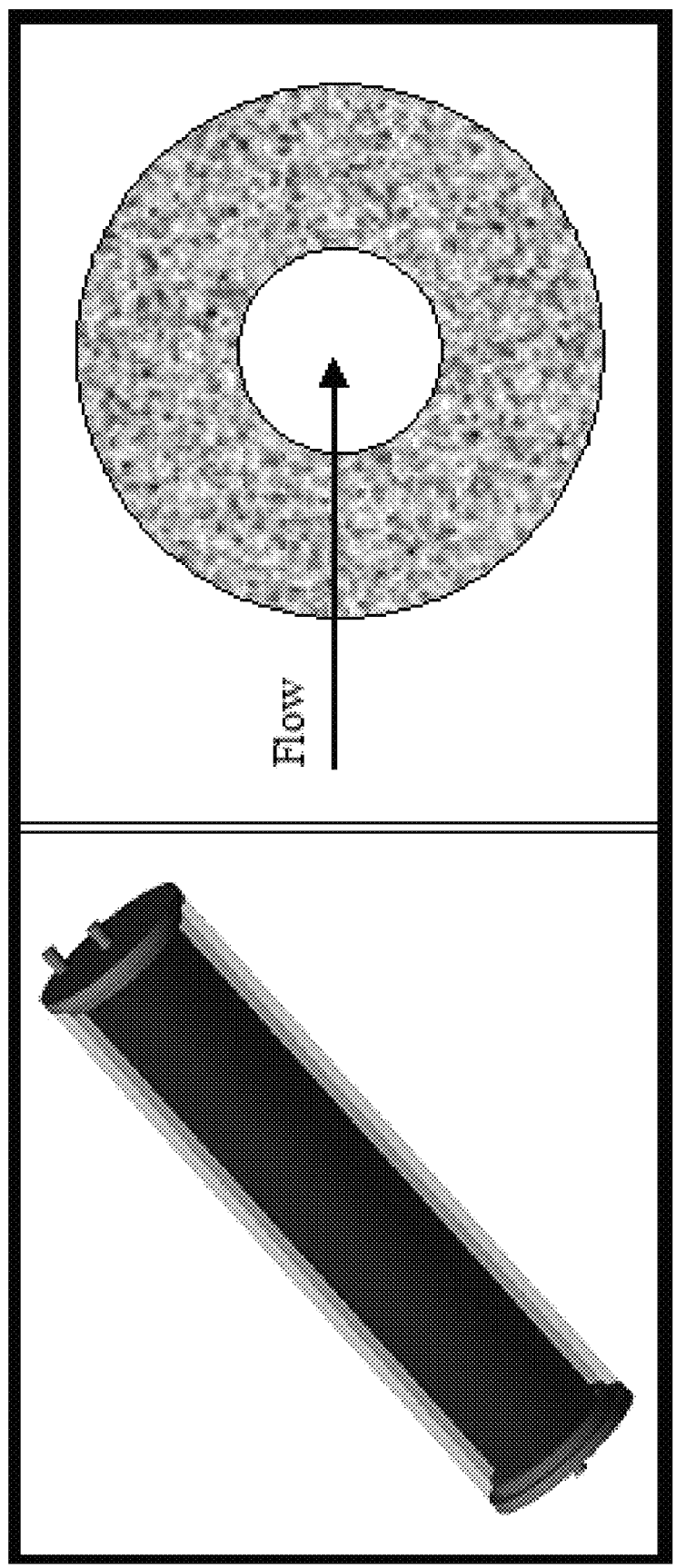

Such filters typically have the following characteristics: The carbon is a whole piece. Thus, no means is required to constrain the carbon from "leaking out" from the reactor as fluid passes through it. The geometry is complex, resulting in fine features as would be the case with powdered active carbon. The mean effective pore length is thus small, resulting in rapid sorption kinetics. They are available in different nominal pore sizes. They are relatively inexpensive, often mass-produced consumer items. Application is simple. The reactor to contain the solid carbon block need only admit fluid to the outer perimeter, collect it from the center hole and seal the ends of the block. (See FIG. 7). They are typically designed for high water flow rates. The hydraulic resistance thus presented even to albumin or plasma at normal dialysis flow rates is modest, typically <200 mmHg.

A Solid Block Reactor (SBR) includes a block of porous, solid block active carbon, along with a suitable container which seals the ends and allows proper fluid flow. The SBR will typically also include other features such as test, evacuation and fill ports, mounting appurtenances, labels, etc.

Figure 8:
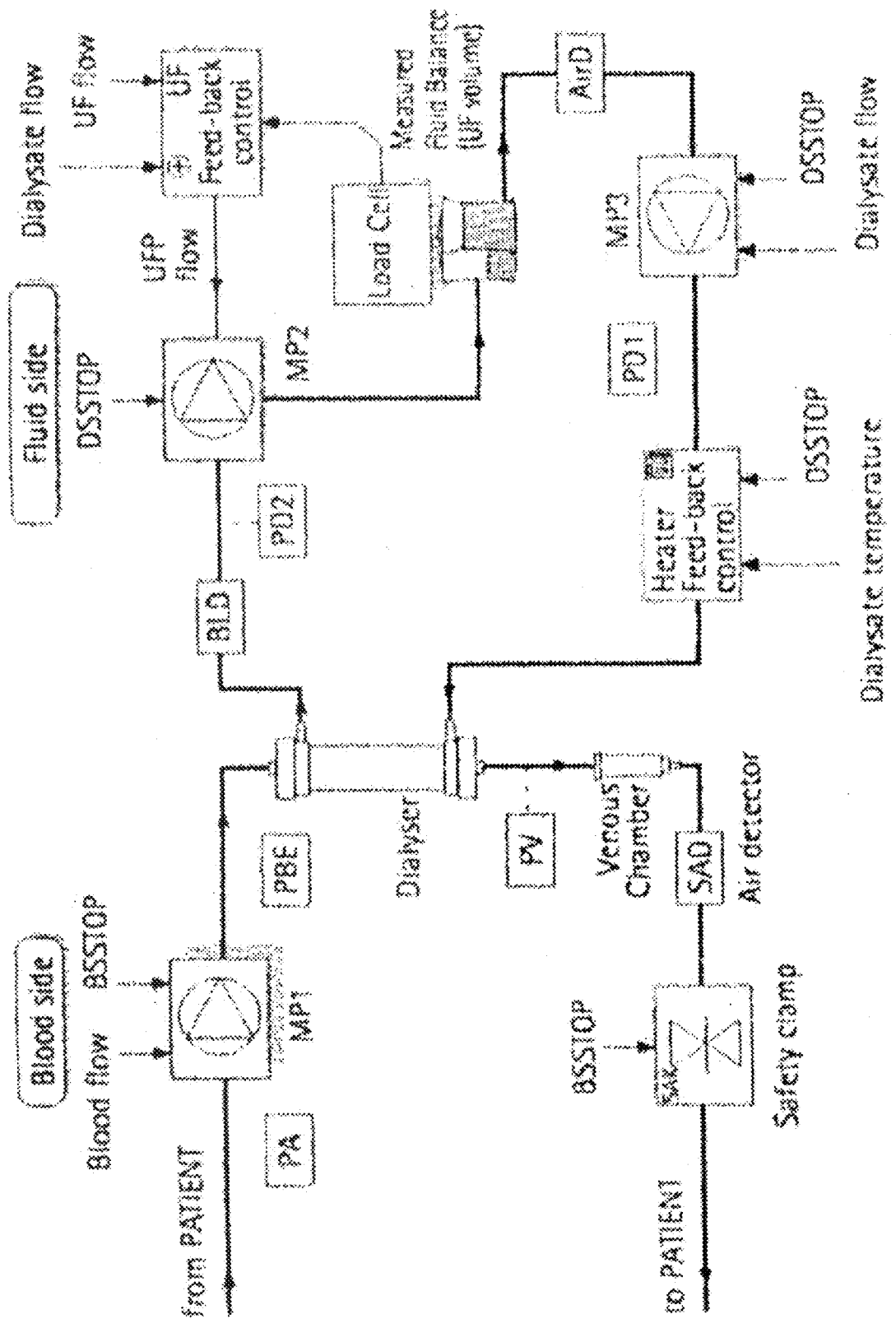

FIG. 8 shows an example of how the solid block reactor (SBR) containing a solid carbon block of active carbon could be used with an existing hemodialysis system. From the patient on the left, blood is pumped through a dialyzer and then returned to the patient. The dialyzer circuit withdraws dialysate from the top of the dialyzer, pumps it through the SBR and thence to a fluid bag. A third pump pumps dialysate out of the fluid bag and returns it to the dialyzer. The difference in flow between the two dialysate pumps creates ultrafiltrate (or an infusion).

It was found in laboratory testing that the surface tension of fluids tends to permit air to be entrained in the porous active carbon block for some considerable amount of time after liquid flow has begun. Such air has at least two undesirable effects. First, in some machine configurations, this air could be returned to the dialyzer or plasma filter, and thus, for some blood filtration devices, to the patient's bloodstream. In severe cases, this could cause air emboli. Secondly, air removes the carbon which it contacts from active participation in toxin sorption.

Figure 9:
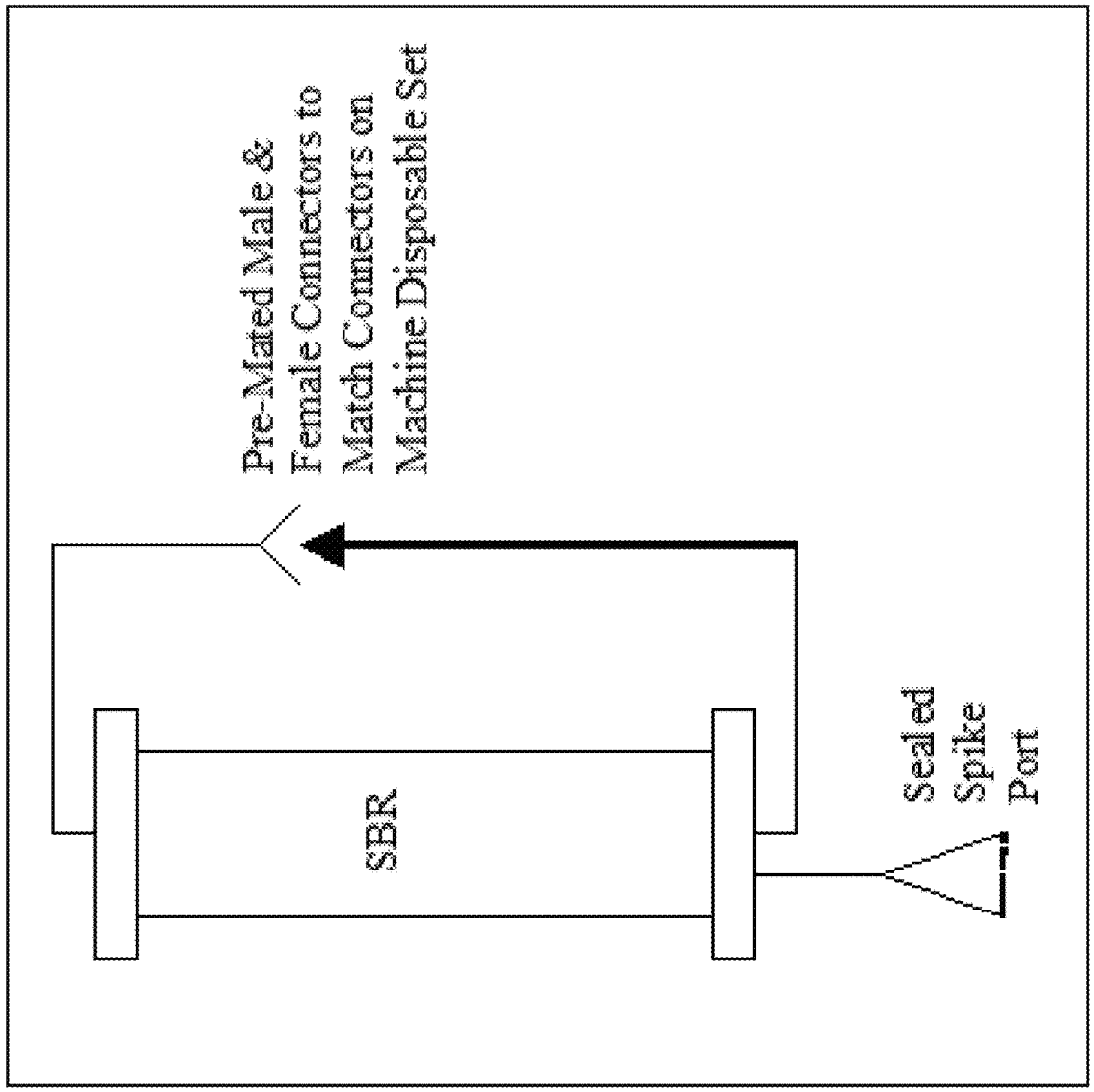

The novel solution to the air is to evacuate the reactor containing the active carbon. A vacuum of 25 mm Hg vacuum or better has proven very effective. Prior to use, the reactor is spiked and filled with one or more bags of priming fluid. Standard sealed IV bag spike ports are used in the reactor so the vacuum is maintained as bags of fluid are connected. It is important that aqueous priming fluid be used to prime the carbon in all cases since proteinaceous fluids such as albumin tend to foam in the presence of air. An example of such a disposable kit ready for vacuum priming is shown in FIG. 9.

An additional benefit is also obtained. Extracorporeal treatment machines are "primed" before use by filling the entire fluid pathway with fluid prior to connection to the patient. The goals of priming are to exclude air from the circuit, and typically, check out the machine operation and discharge any impurities in the fluid circuit.

With an evacuated SBR, the SBR is easily filled with fluid from standard IV bags. Thus, the host machine is primed normally, and the now fluid-filled SBR is then inserted prior to treatment without need for changes in the machine's existing operating protocol. The SBR thus becomes simple to install and apply.

It should be noted that vacuum assisted priming is only an option, not necessarily a requirement; most carbon blocks cease to emit air after 30 to 45 minutes after start of priming at 200 mL/min and would take less time at higher flow rates.

Figure 10:
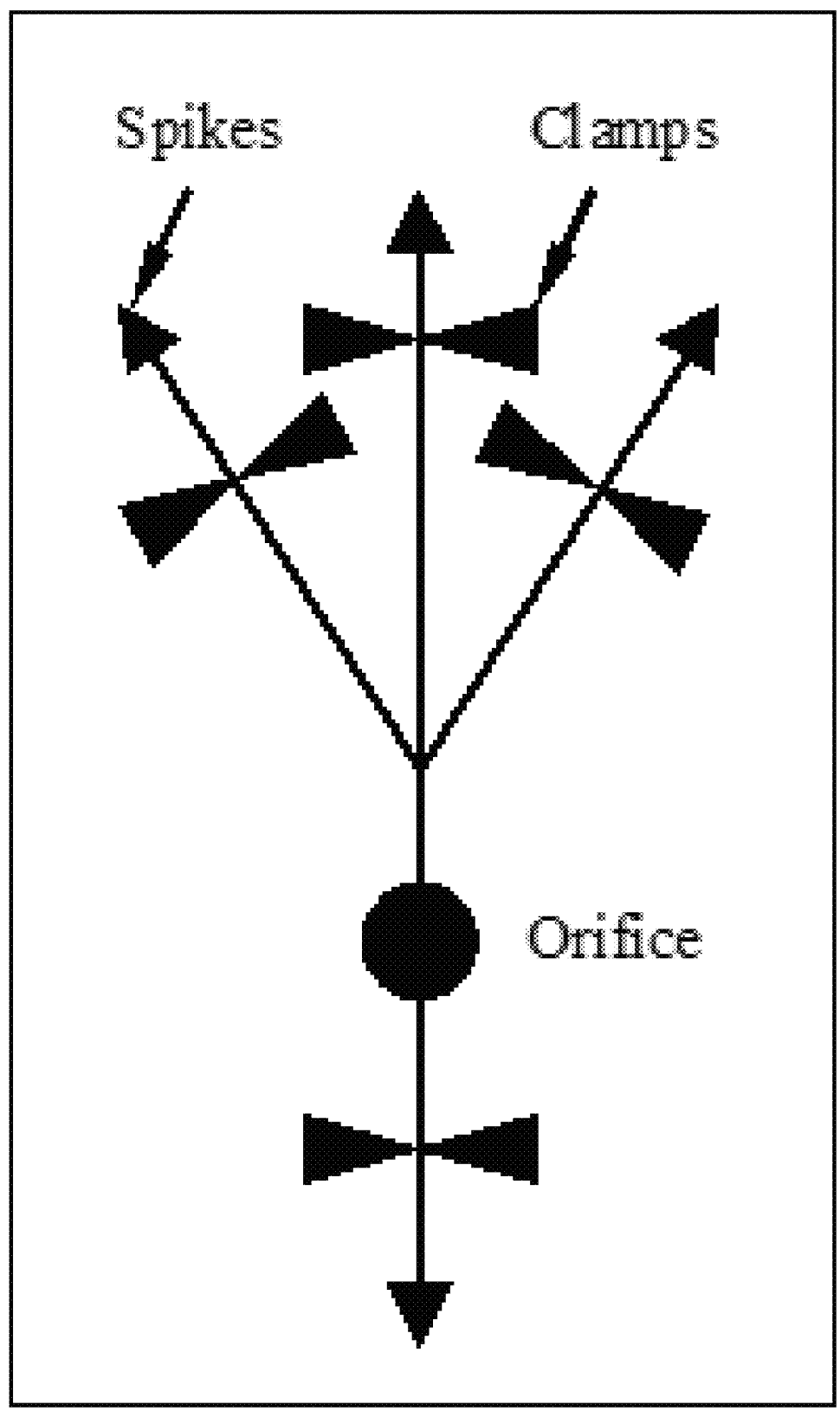

As shown in FIG. 10, an orifice may be provided to prevent the SBR from exhausting an IV bag faster than the operator can react to close off a nearly empty bag and open a fresh bag. This prevents air in the bag from entering the SBR.

Laboratory Results

Presented below are comparisons between an active carbon SBR and other methods of utilizing active carbon as they apply to different treatments. These data serve to illustrate the benefits of the SBR and demonstrate that the use of an SBR does not result in any significant decrease in therapeutic performance.

The Biologic DT has, as a major labeled use, the treatment of patients with acetaminophen overdose. This machine uses a circulating suspension of powdered active carbon on the dialysate side of a flat plate dialyzer. The results are compared with a laboratory test using an SBR. No dialyzer was used in this test; the load on the SBR active carbon was thus the more severe.

Figure 11A:
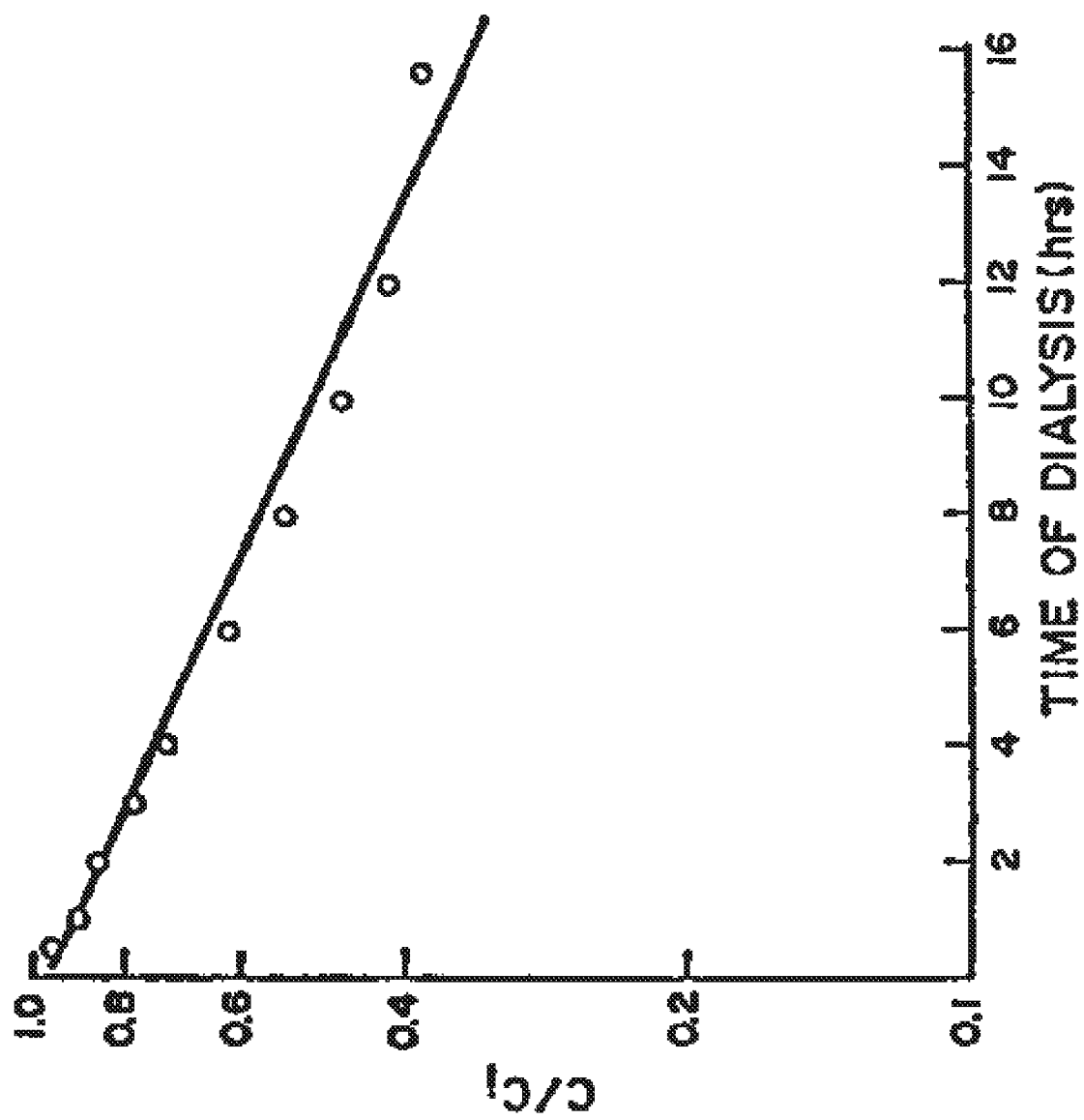
Figure 11B:
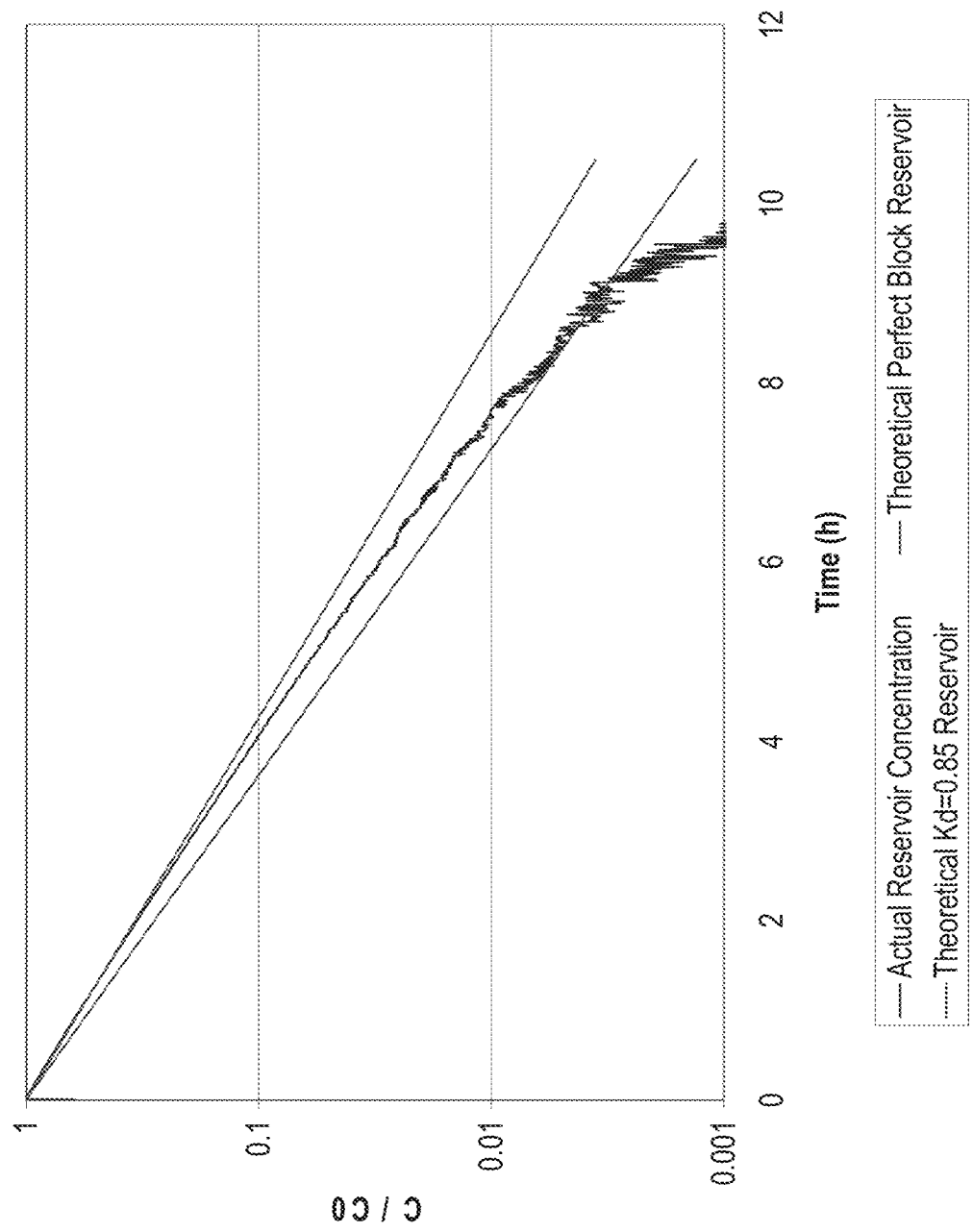

In the data in FIG. 11B, the Theoretical Perfect Block Reservoir shows the concentration of acetaminophen in aqueous dialysate using a simulated 40L patient if the active carbon were a perfect "black hole" for acetaminophen. The Theoretical Kd=0.85 Reservoir is the same data, but assuming the use of a dialyzer in the circuit in order to make the data comparable to the graph on the left. As may be seen, there is massive improvement over the older circulating suspension technology. (Note graph scales carefully.)

The SBR was compared with granules and other forms of carbon using highly mesoporous carbon block. The dwell time, the time between when fluid enters the reactor and when it exits, was seven minutes. Dwell time is simply the volume of the SBR divided by the flow rate. Three different markers, Methylene Blue (MW=320), Albumin (MW≈65K) and Blue Dextran (MW≈2M) were used with aqueous buffer and a fourth, Bilirubin (MW=585) was used with bovine plasma. In that graph, the "Nanofiber" was similar to KX Industries' "Plekx" material.

Finally, the SBR was compared with some cytokines (various MW) which are implicated as sepsis mediators. Note that the HSDG was optimized for cytokine removal.

Figure 12A:
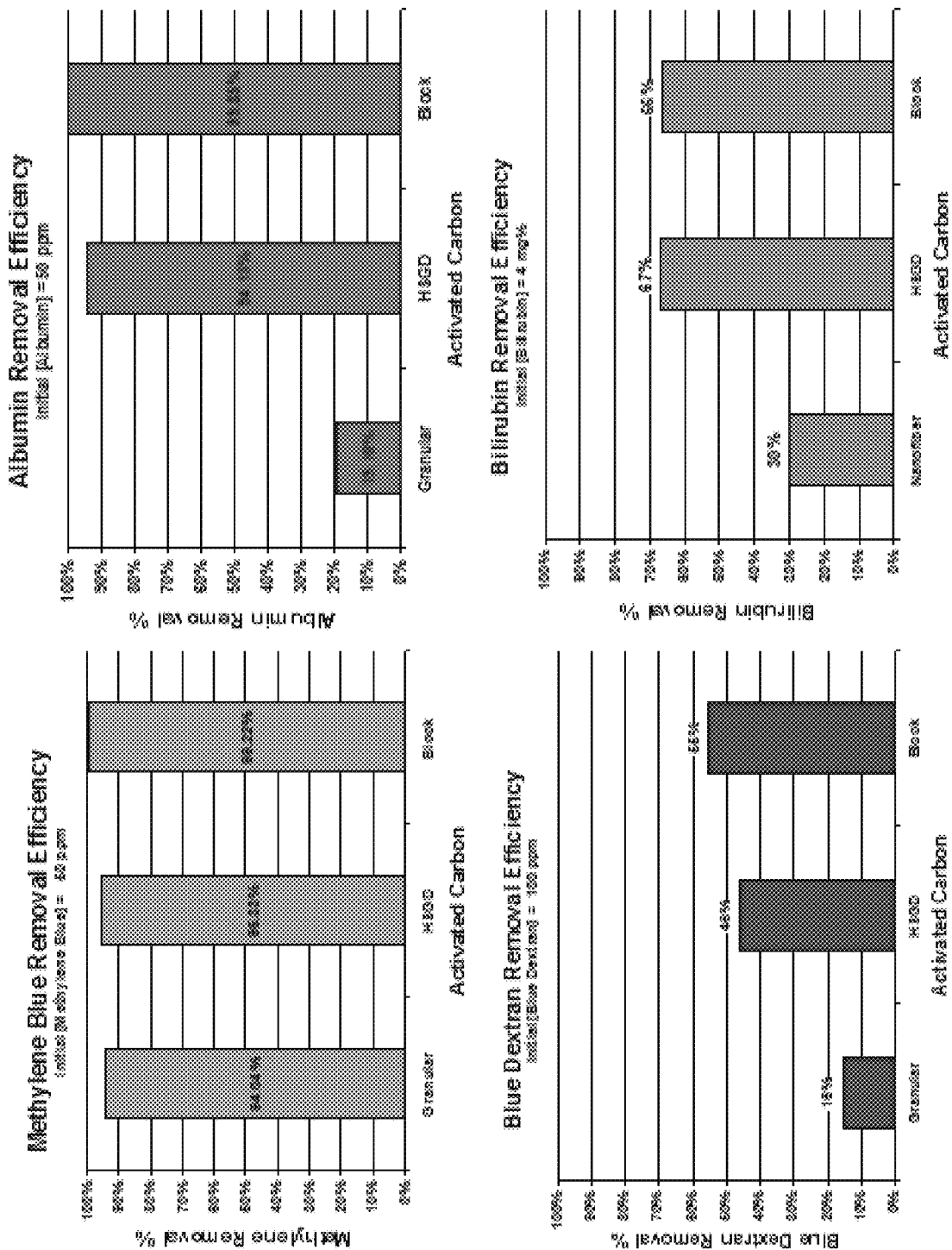
Figure 12B:
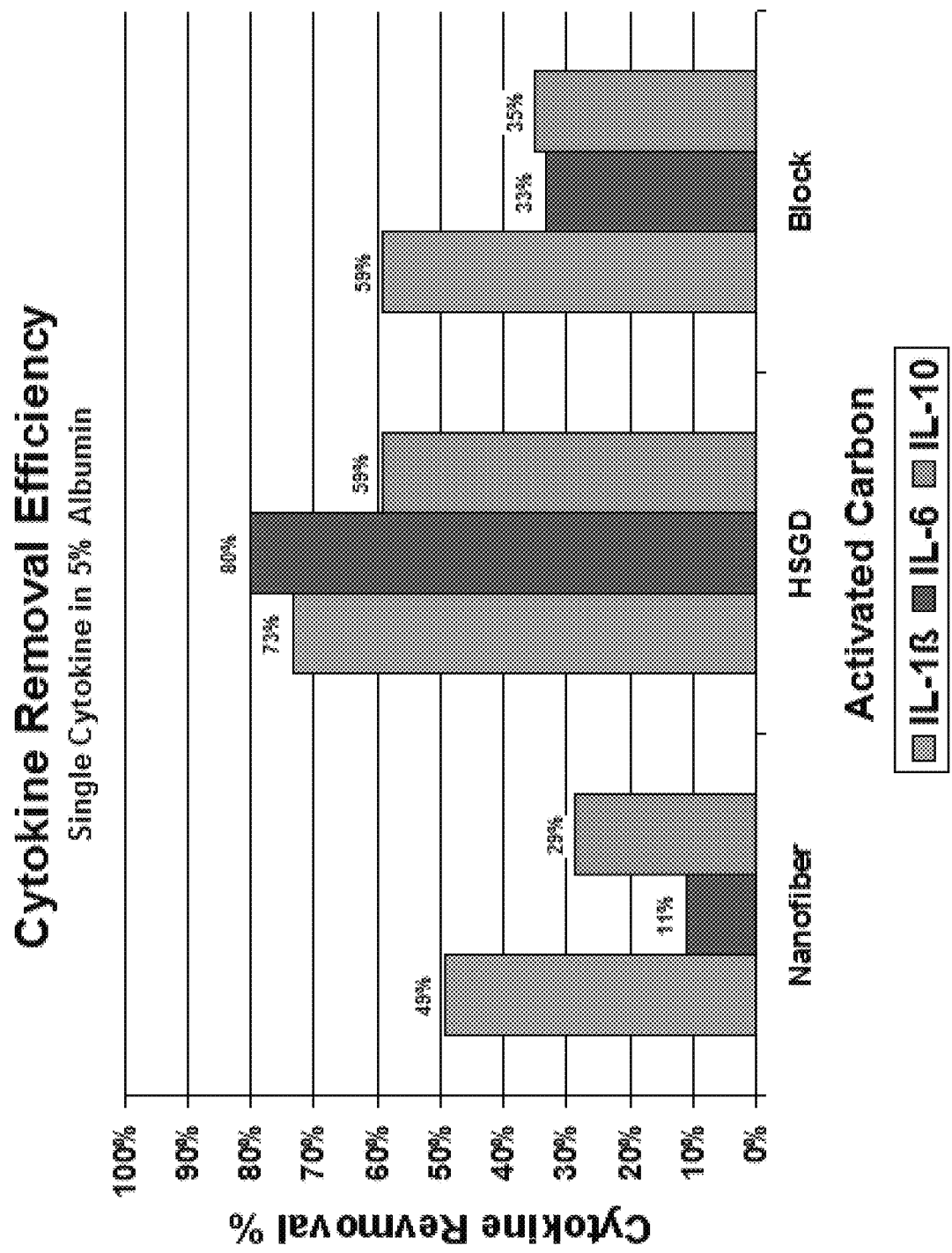

The results are shown in FIGS. 12a and 12b. Clearly, the application of porous solid block carbon to extracorporeal blood treatments is beneficial and useful.

Another clinical application of the carbon block will likely be in a dialysate regenerating circuit that is used to remove toxins which develop during whole body hyperthermia (a potential therapy for cancer). This will be done to provide the same chemical function we had with the Bio-Logic-HDT system, which used powdered charcoal, a cation exchanger and a precipitated calcium phosphate as a sorbent suspension (described in Section C). We have collaborated with the KX Company to create carbon blocks containing the same powdered carbon as was included in our BioLogic-HDT system (derived from coconut shells). We have tested these carbon blocks and shown that binding of toxins is essentially the same as for the powdered carbon in suspension. The carbon block we plan to use will be packaged in a clear plastic housing, evacuated of air, and be clean but not sterile. It contains about 300 grams carbon and is approximately 10" long and 2.5" in diameter.

Section A-2: Special Applications of Sterile Carbon Block

As described above, regeneration of dialysate during standard hemodialysis can be performed using sorbents which are clean but not sterile. In a treatment of 3-8 hours, bacterial proliferation is not a problem. However one type of hemodialysis therapy is performed for very long periods, up to 72 hours, and therefore utilizes sterile dialysate. This type of dialysis is called "Continuous veno-venous hemodialysis" or "CVVHD." A variation of this therapy is "Continuous veno-venous hemofiltration" or "CVVH." In this therapy, the removal of toxins is by hemofiltration (convection) across the dialyzer membranes, and sterile fluid is infused to the blood to replace the filtered fluid. Here also, sterile fluid is used for infusion to the blood returning to the patient. A combination of hemodialysis and hemofiltration techniques is also used, called CVVHDF. In any of these applications, if the dialysate or hemofiltrate is to be regenerated by carbon block, the carbon block must be sterile and provided within in a sterile perfusion cartridge.

Gamma radiation is a practical method for sterilizing many medical devices. Carbon is relatively insensitive to gamma radiation; it is used extensively in nuclear applications as a neutron moderator in nuclear reactors and in high-energy particle accelerator installations to receive beam dumps. Carbon blocks that are made with binder typically use either polypropylene or polyethylene in various molecular weight formulations. The latter has been shown to withstand gamma radiation doses up to 1000 kGy. It is thus a reasonable expectation that carbon blocks may be successfully sterilized by gamma radiation, but there does exist some concern that the pore structure might be modified by the sterilizing gamma dose. To test this concern, four carbon blocks were tested, two of which received a gamma dose measured to have been between 35.62 and 37.84 kGy over 1000 minutes.

Figure 13:
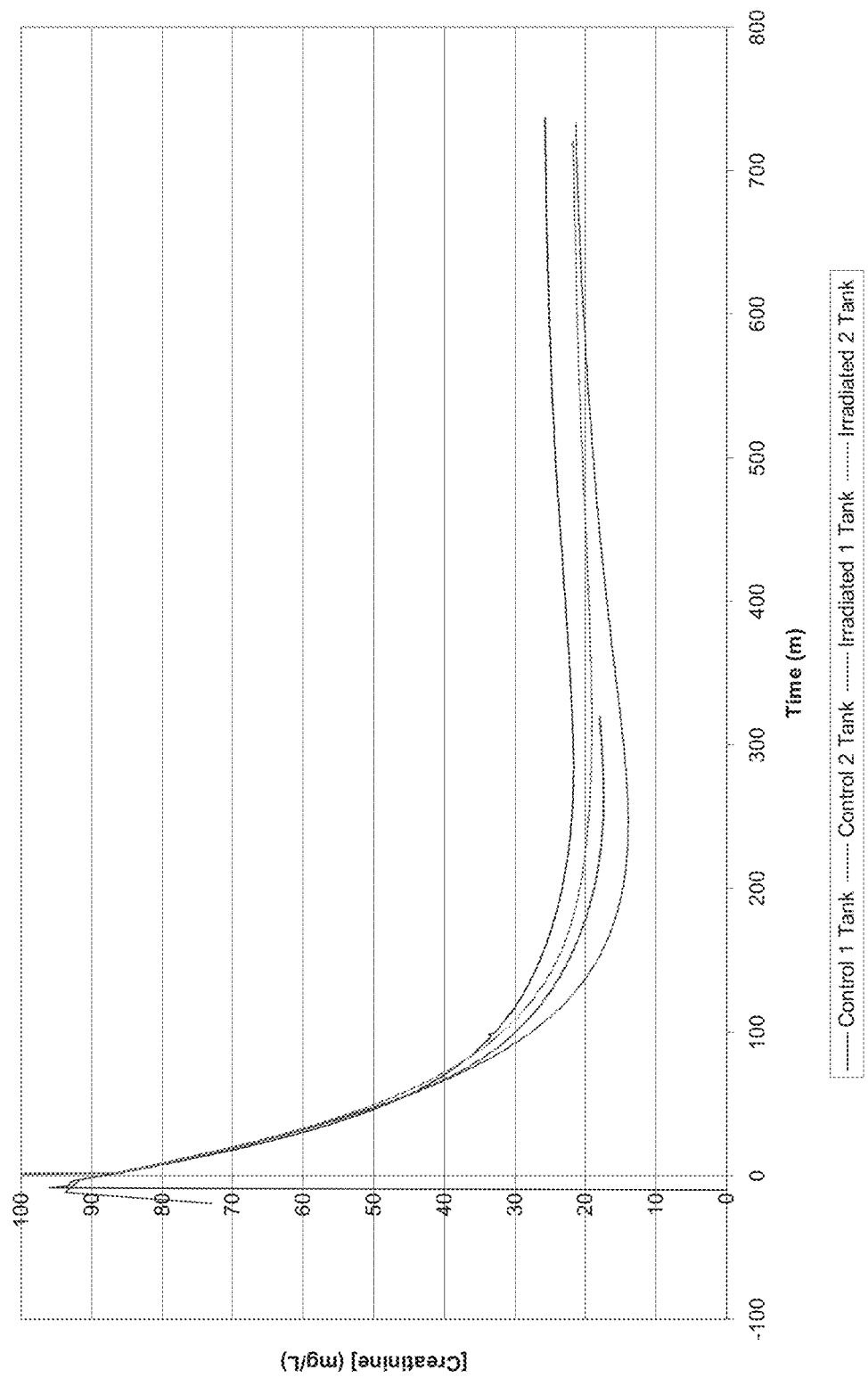

As may be seen in FIG. 13, there is not a significant difference in creatinine adsorption performance; the curves for the two irradiated blocks are bracketed by the curves of the two non-irradiated blocks.

As described above, granulated carbon has been successfully used in dialysis, for example in the REDY, Biologic DT, and Allient machines in a non-sterile circuit. However, in some dialysis therapies, such as CVVHD (Continuous Veno Venous HemoDialysis), treatments are of long duration (up to 72 hours) and require a sterile dialysate circuit. In many cases, patient toxin (e.g., bilirubin) or ion (e.g., potassium) loads may be low or it may be deemed desirable to not remove beneficial substances from the patient (e.g., glucose). This may particularly be the case for patients suffering from drug overdose.

Figure 14:
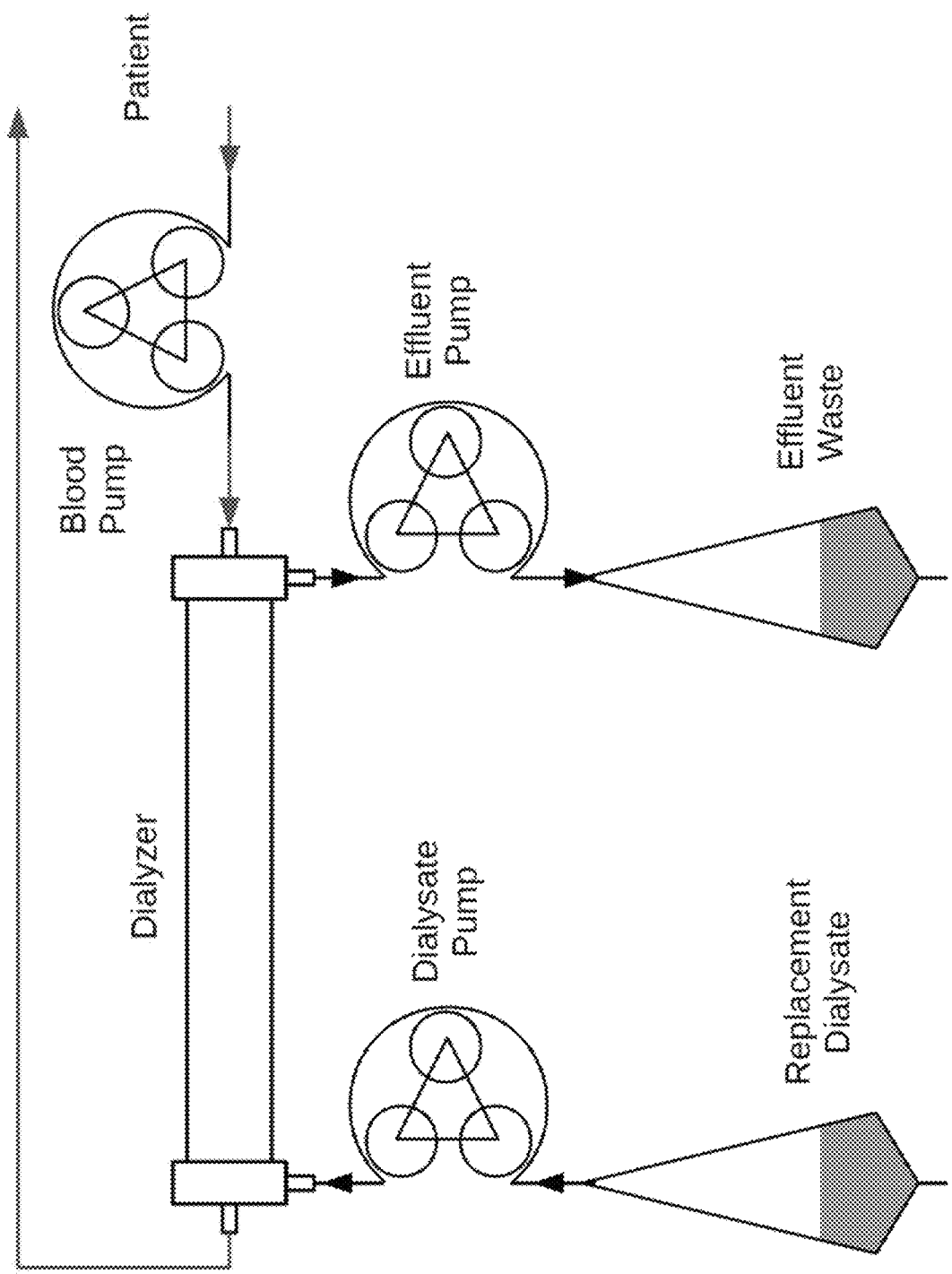

By way of an example treatment modality, FIG. 14 shows a simplified schematic of CVVHD. The dialyzer provides a bidirectional exchange of substances across the dialyzer for the purpose of equalizing concentrations of substances in the patient's bloodstream with the concentrations in the dialysate. This equalization is never perfect, but is a function of relative concentrations, time, and the permeability of the dialyzer membrane for a given substance. To move this equalization process forward, there typically must be continual replacement of the dialysate. Thus, the operation of the system is basically straightforward; fresh dialysate is simply pumped through the dialyzer into a waste container. To remove fluid from the patient (ultrafiltrate), the effluent pump pumps more fluid from the dialyzer than the replacement dialysate pump. The conventional method can require fairly high volumes of fluid and typically requires careful preparation of the replacement dialysate to assure sterility and purity. In this and succeeding figures, many required accessories such as blood leak and pressure monitors are not shown.

Figure 15:
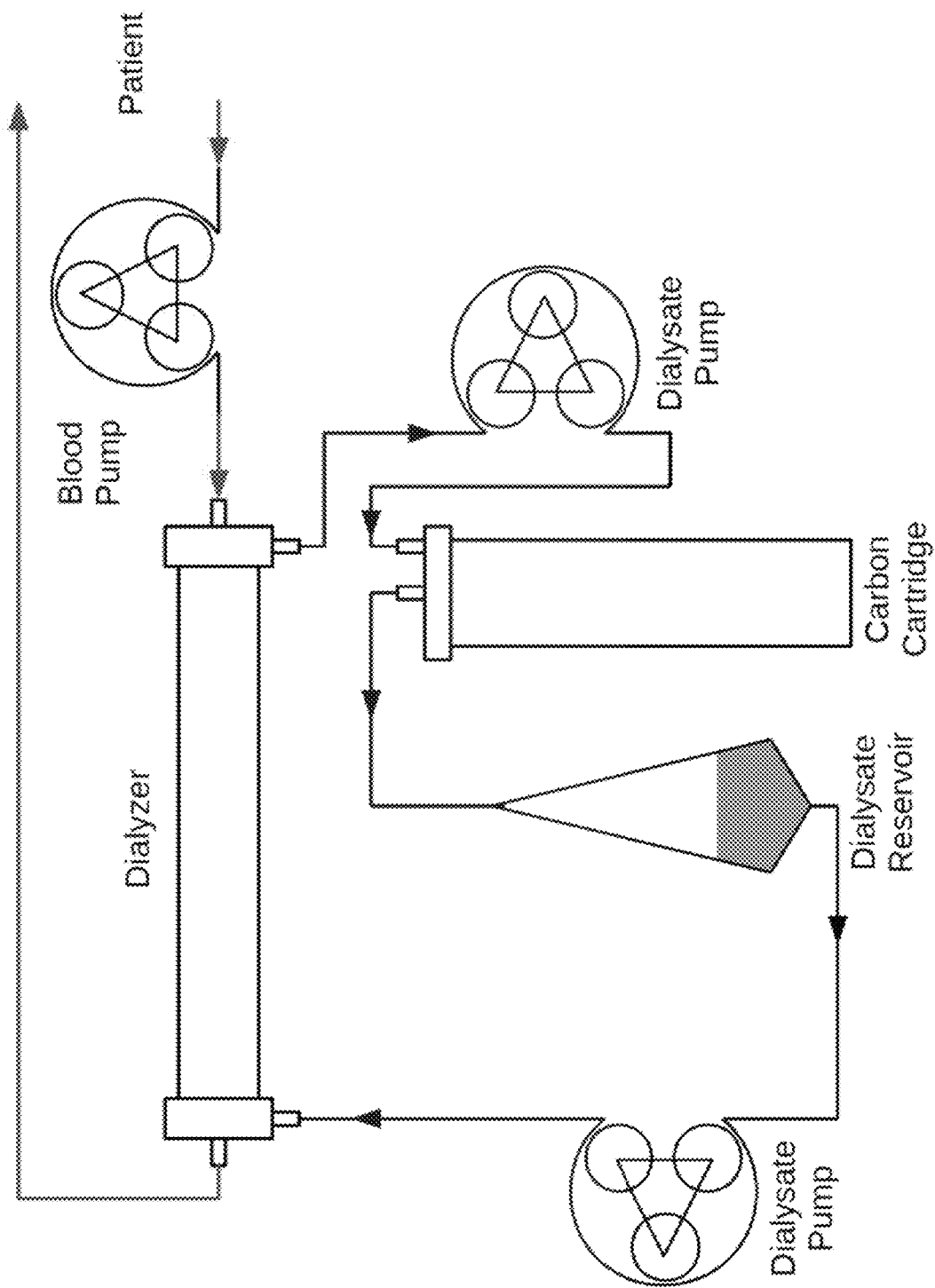

FIG. 15 shows how a carbon block can be used to purify the dialysate. This purification can take place both with respect to contaminants in the dialysis fluid as supplied, and also of substances removed from the patient. Due to the porous nature of the carbon block, air will be emitted from the block for some considerable time, so the arrangement shown or some other method will be necessary to prevent air from reaching the dialyzer. Such air does not normally enter the patient's bloodstream across the dialyzer membrane, but it does remove useful surface area from the dialyzer.

Those substances which are prescribed to be added to the patient may be loaded into the dialysate bag prior to the start of treatment. During a treatment, the carbon block, the dialysate bag, or both may be changed as needed.

Figure 16:
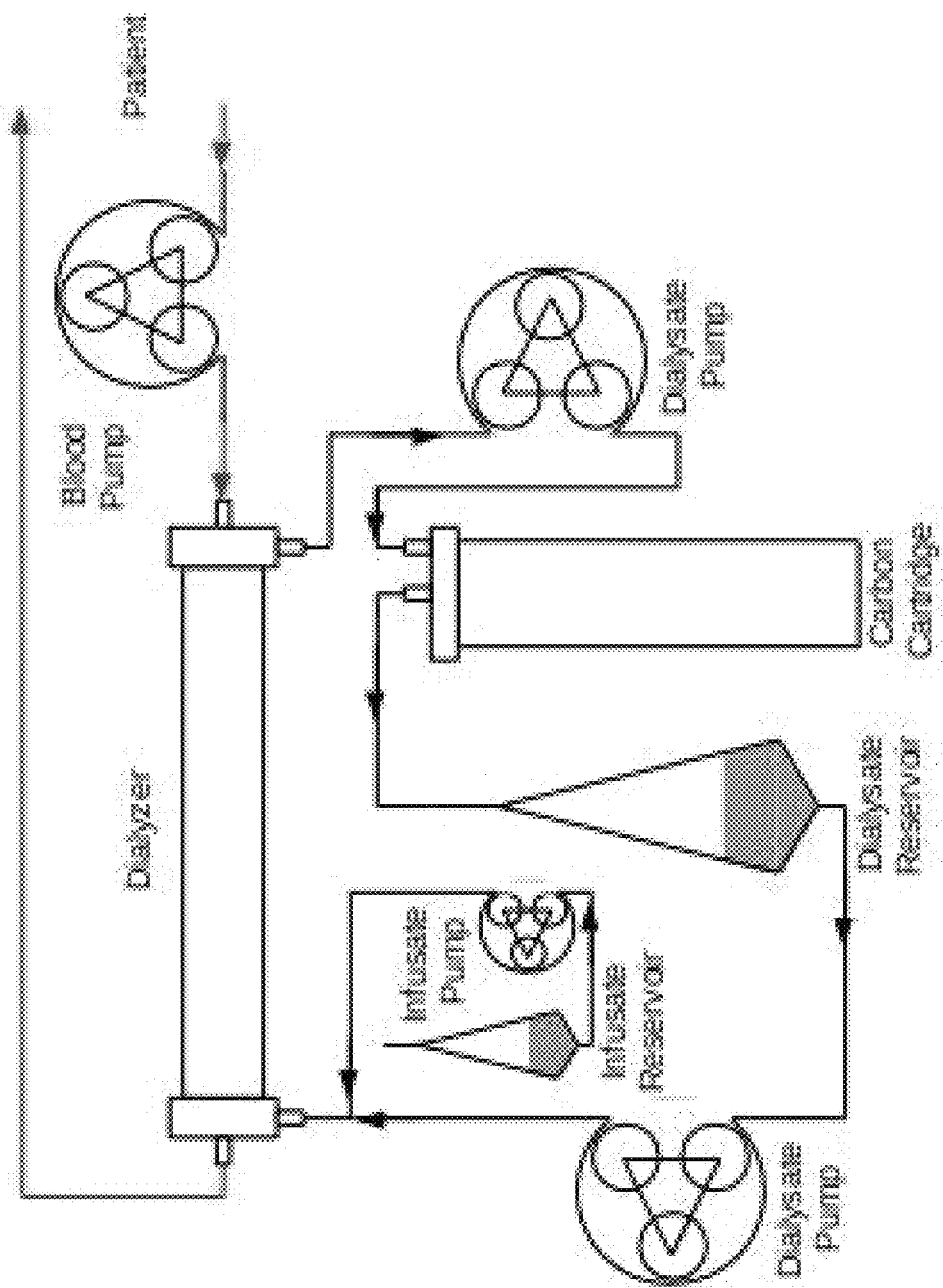

As shown in FIG. 16, instead of, or in addition to, preloading the dialysate bag with prescribed substances, a separate infusion pump and infusate reservoir may be added in order to provide a continuous addition of substances to the patient.

Figure 17:
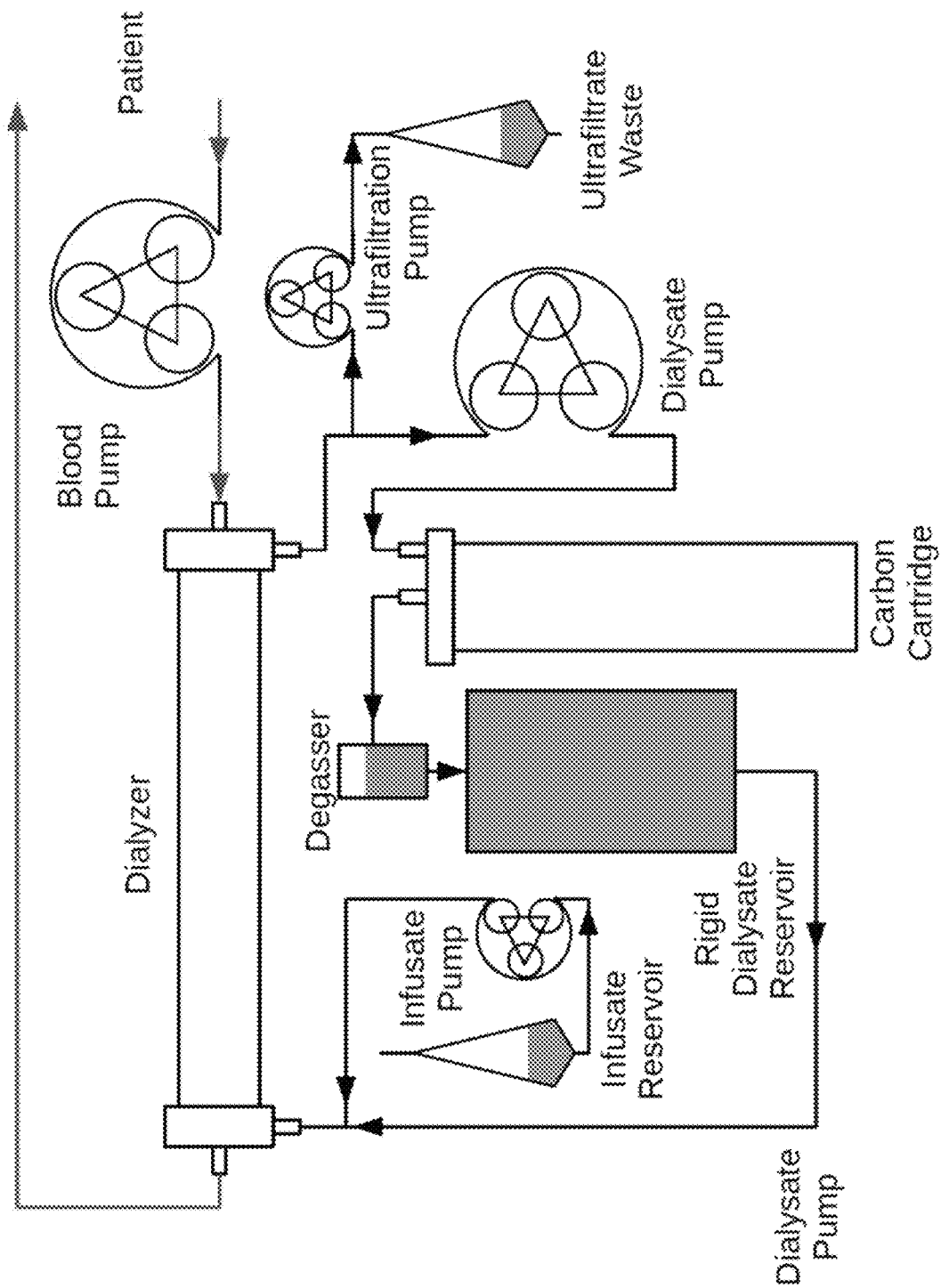

FIG. 17 shows another addition; by adding an effluent pump and reservoir, there can be a continuous exchange of dialysate. In this case, the flow of dialysate from the infusate reservoir to the effluent reservoir can remove substances from the patient which are not well removed by the carbon block. (Note that in the former case, infusate will be delivered in relatively small amounts, while in this case, infusate will be used to exchange the dialysate in relatively large amounts.)

In certain other treatment methods, rather than adding infusate to the dialyzer, the infusate or other replacement fluid can be added directly to the patient's blood before the dialyzer, after the dialyzer or both. This may be done alone or in combination with any of the above described methods.

Although CVVHD is used as an example, the concept of using a sterile carbon block to regenerate all or part of the dialysate is applicable to a wide variety of therapies. Each of these therapies will have its own special plumbing arrangements; such different arrangements fall within the scope of this disclosure.

In regeneration of dialysate, carbon removes principally organic toxins greater than 100 m.w. This includes many "middle molecules" that have been shown to cause illness during kidney failure. However, there are some smaller and charged toxins of kidney failure that are not removed by carbon, including: urea, phosphate, sodium, potassium and acid. The acidity of blood is represented by a deficiency in concentration of various bases in the blood, and is corrected by addition of basic compounds such as bicarbonate. More complicated columns such as the Sorb include layers to remove these various small and charged toxins, but they require some careful management and priming to produce just the desired changes in body chemistry. With carbon regeneration of dialysate in CVVHD, the removal of larger molecular weight organic toxins can be greatly increased by merely increasing the dialysate flow rate. In standard CVVHD since the dialysate is sterile, pre-packaged and expensive, dialysate flow is typically 30-50 ml/min. This slow flow limits the chemical efficiency (clearance) of the system greatly. With carbon-regeneration of dialysate the flow rate can be increased to 400 ml/min without any increase in cost except the cost of the column. The removal of small charged toxins, and replenishment of bicarbonate can be simply provided by changing the bags of dialysate when required to supply the needed changes in body chemistry (such as several five liter bags per day). The concentration of the dialysate can also be chosen or adjusted for "fine tuning" the removal of the small, charged toxins. Thus, for the first time, CVVHD with charcoal regeneration of dialysate gives the physician the capability to control rate of removal of two different types of kidney failure toxins from patients, according to their needs: larger organic toxins and small charged toxins.

Section B: The Filtration Bed for Immobilizing Small Sorbent Particles.

Introduction The second technology for immobilizing powders which we have developed is a filtration bed which positions particles on the outside of the carbon block during fluid flow. For function in a hyperthermia circuit the sorbent used in the filtration bed will be calcium phosphate. The function of the calcium phosphate ($CaHPO_4$) layer is to absorb one toxin (acid, H+) and to modulate or control levels of calcium and phosphate in the dialysate. Working through its solubility product, calcium phosphate will release calcium or phosphate if their levels are low in the dialysate. If the levels are high, it will remove calcium and phosphate. The dissolution or creation of calcium phosphate is possible only when there is a very high surface area/weight, meaning very small particle size (such as a few microns). When employed in the original BioLogic-HDT circuit, the calcium phosphate in the dialysate was precipitated on the surface of the carbon powder particles and held in suspension. The suspension moved through the dialyzer, propelled by membrane motion and vacuum/pressure gradients. In the current application, the calcium phosphate will be a powder that is held motionless in a filtration bed around the carbon block. Other applications of sorbents also require very small particle size, such as use of microporous crystals of zirconium silicate, for binding potassium and ammonium in a dialysate circuit). Note that calcium phosphate is exemplary; other substances may also be used.

Figure 18A:
Figure 18B:

At a modest flow rate such as 250 ml/min a finely powdered sorbent, such as calcium phosphate ($CaHPO_4$) will form a layer fixed on the outside of the carbon block. Fluid flow through the layer proceeds without any significant pressure gradient (with 100 grams of calcium phosphate, about 60 mm Hg pressure drop). With perfusion of dialysate around the particles, calcium phosphate powder can dissociate and deliver soluble phosphate whenever the dialysate calcium×phosphate product decreases below the dissociation constant for calcium phosphate, just as it did in the suspension of the BioLogic-HDT system. The photographs below (FIG. 18) show the carbon block and calcium phosphate powder without fluid flow through the carbon block (left) and with fluid flow of 400 ml/min (right). With fluid flow, the calcium phosphate powder is firmly applied to the outside of the carbon block, but fluid flow continues through this filtration bed of particles without any significant increase in pressure gradient (57 mm Hg at 400 ml/min flow rate). When flow is stopped, the calcium phosphate powder falls downward to the bottom of the canister (as shown on left), and the powder will re-suspend and apply itself to the outside of the carbon block when flow resumes. None of the powdered calcium phosphate penetrates into the block (as shown by sections of the block after use), and no particles permeate the block. The calcium phosphate powder is in intimate contact with all fluid flowing through the filtration bed and apparently, the fluid flow is very uniform.

Concept of Structure and Function of the Carbon Block/ Filtration Bed, and Why Flow and Function is Different from a Standard Sorbent Column It is helpful to compare the present invention with standard packed columns. With a standard sorbent column, large particles or granules are used as sorbent. As discussed above, the finest particles used within sorbent columns is approximately 50 microns, and this small size allows uniformly distributed flow without very high pressures only if the particles are spherical. For applications of carbon in columns the particle size is usually quite large (such as 1-2 mm) and the individual granules are easily palpable. To load a standard column, the dry granules or sorbent particles are usually poured into the open column, a top is attached, the column is inverted to begin filling (allowing air to escape) and fluid flow is begun. When the air has been expelled, the column is inverted again. Sometimes the column is filled with fluid and then the sorbent particles are poured in. Whether filling a wet or dry cannister, the force of gravity and chance determine the position of granules when perfusion starts. Larger granules are interspersed with smaller ones. If one area has a greater proportion of large granules or a small channel space, then during fluid flow through the column this channel will widen and fluid flow here will be more rapid than that through the rest of the portions of the column, as can be demonstrated during dye injection. The result of this rapid flow is early saturation of the sorbent granules of the channel, and subsequent early "breakthrough" of bound toxins or compounds. Further, the interspersing of large and small granules tends to form a tight pack (much like occurs with use of varying gravel size used in road construction). However, to a large degree, the use of uniformly sized particles, sophisticated column packing techniques, packing fluids and apparatus can greatly reduce these problems. Such techniques do, however add significant cost to the column. When we have attempted to make a column out of our calcium phosphate powder, we have found that when we begin fluid flow the powder forms a very dense semi-solid "cake" and perfusion pressures at low flow rates are in the hundreds of mm Hg, for columns that are only about 1 cm thick.

The method of constructing the outer powdered sorbent layer of the carbon block/filtration bed device is quite different. The loose and very fine powder is placed in the bottom of the canister, and the fluid flow is begun. The fluid flow rate exceeds the sedimentation rate of all of the particles and therefore the particles are carried with the fluid against the force of gravity. It is likely that during the fluid flow the finest particles are carried to the surface of the carbon block first, then the larger granules. As the particles form layers around the various portions of the carbon block, then hydraulic resistance of each portion becomes higher and fluid flow automatically re-directs to portions that do not have a powdered bed layer. After the entire carbon block outer surface is covered, then there are probably still portions which have higher flow. However, the higher flow in these channels brings with it more sorbent particles and the channels tend to fill and resolve automatically. The powdered bed appears to be less likely to pack tightly compared to a standard column. Whereas it required several hundred mm Hg of pressure to perfuse a standard column created from calcium phosphate powder, the carbon block/filtration bed held about 50 grams of calcium phosphate powder and when perfused at a rapid rate of 250 ml/min had a pressure gradient of about 57 mm Hg.

Figure 19A:
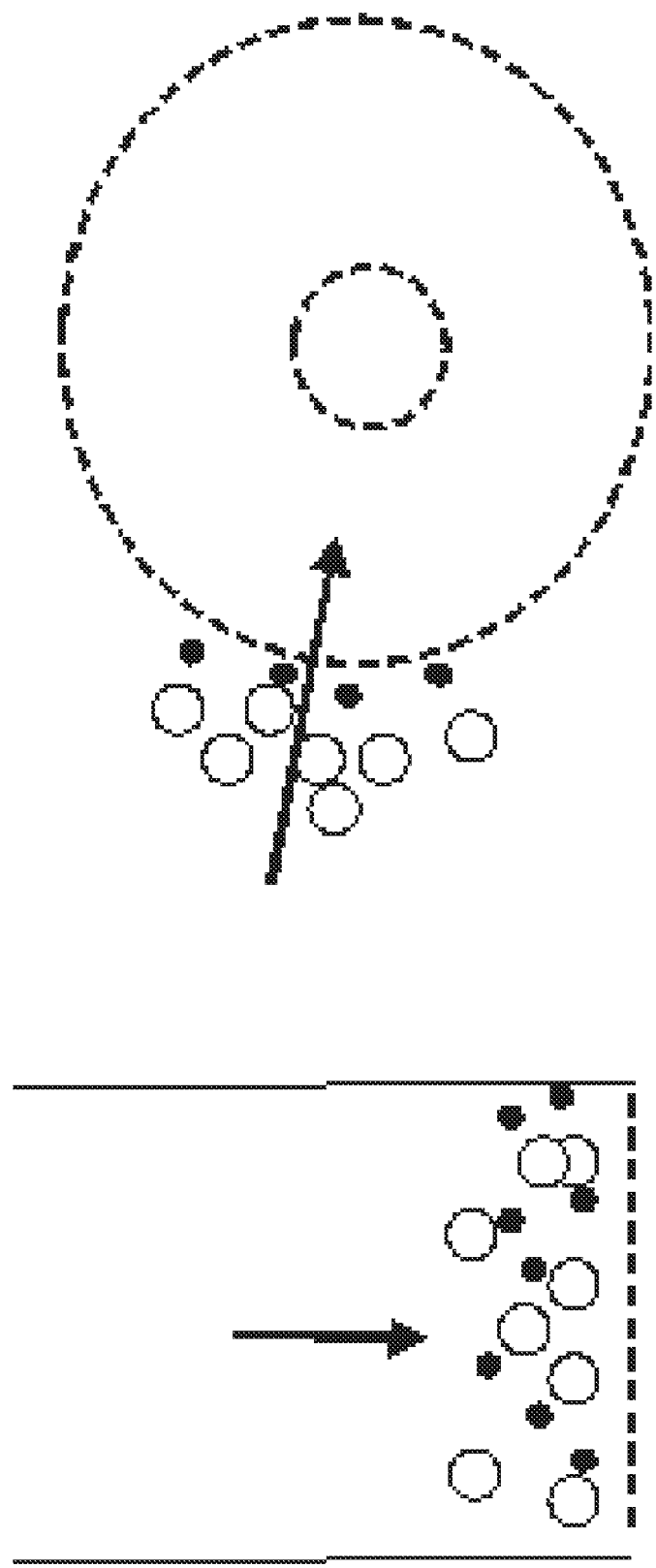

Another feature of the carbon block/filtration bed that distinguishes it from a standard column is the shape of the sorbent layer. Instead of being a cylinder with fluid flow along its axis and a filter at one end, the filtration bed on the carbon block forms as a layer around a cylinder with fluid flow on an inward direction normal to the surface of the cylinder. The use of the outer surface of the carbon block as the filtering surface means that there is a very large surface area for filtration and support of the powdered sorbent bed. This means that a very large amount of powder may be applied to the surface of the carbon block without creating a thick layer of powder. As an example, one size of the Matrixx KX-5 is 2.5 inches in outer diameter and 10 inches long. The circumference is thus about 8 inches and the surface area of the outer portion is about 80 square inches. If this same surface area were created as a flat filter at the bottom of a cylindrical column, the diameter would be approximately 10 inches (about 25 cm). If the desired thickness of the sorbent layer were only 1 cm, this would result in an aspect ratio (width:height) of 25:1 for the column, a configuration which would certainly encourage irregular flow. However, with the filtration bed, it appears that flow is uniform through all parts of the bed (judging from the structure of the bed alone). If a standard column were created with a more standard aspect ratio such as 1; 1 or less, then to utilize the same amount of powdered sorbent it would require a column height many times higher. The longer fluid flow path would greatly increase the hydraulic resistance of the column. The large surface area of the outside of a cylinder has a second advantage, in that it diminishes the rate of fluid flux through the sorbent layer (flow rate per cm2 of filter surface). The result is increased dwell time which improves reaction kinetics. This decreased flow rate also decreases the hydraulic pressure drop through each cm2 of sorbent bed. This benefit is of course another way to describe the benefits of a very high aspect ratio for the filtration bed. A simple depiction of differences between a standard column and the carbon block/filtration bed approach is shown in FIG. 19a.

Figure 19B:
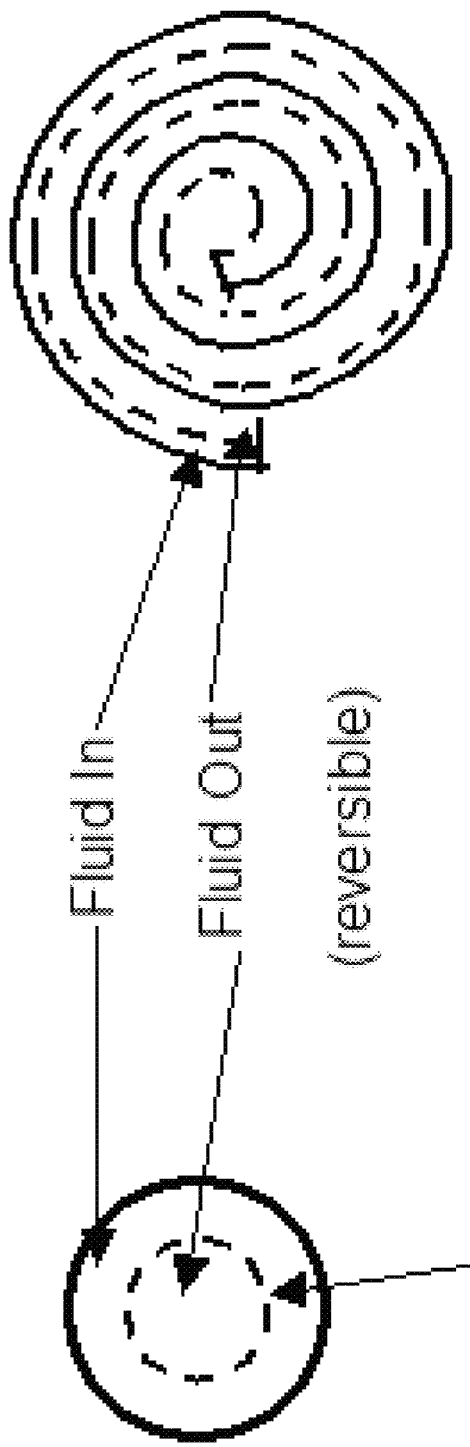

Clearly, other variations on this same principle are possible. For example, a "column" may be constructed with or without the carbon, having a membrane, filter, screen or other means (designated "screen" hereafter in this paragraph) with which to constrain particles. Multiple geometries are possible. In all cases, there are three requirements. First, the zero-flow position of the particles must be substantially away from the screen. Gravity would be the normal means of achieving this, but reverse flow is also a means. Secondly, the particles must readily suspend during flow by means of an appropriate combination of particle size, fluid density and viscosity, other fluid characteristics, fluid/particle affinity, surface tension, etc. Thirdly, the particles must have limited affinity for one another to avoid clumping and other undesirable aggregation. Surfactants in the fluid may possibly be included in the fluid to aid in meeting these requirements. FIG. 19b exemplifies this concept. Also, of course, carbon or other materials or sorbents may be formed into solid porous blocks (in place of the screen of FIG. 19b) of various shapes by which means fluid volume and space requirements may be reduced for a given surface area. A vertical system is also quite possible; the screen is at the top of a short column of large diameter.

Use of Carbon Block/Filtration Bed to Regenerate Dialysate in a Dialysis Machine With the carbon block and filtration bed of calcium phosphate (plus the cone reactor as described below, in some circumstances) we can recreate the chemical function of the BioLogic-HDT system using a dialysate regenerating system in which dialysate flows uni-directionally through the canister. This system is more conventional than was the sorbent suspension system, is more similar to a standard sorbent column, and is easily compatible with regeneration of dialysate flowing through a standard hollow fiber dialyzer. The powdered carbon will effectively remove almost all organic toxins which penetrate the membranes. The calcium phosphate will operate by solubility product to modulate the dialysate concentration of calcium, phosphate and bicarbonate. When any of these electrolytes become abnormally low, the calcium phosphate will automatically replenish them. When any of these electrolytes become abnormally high, the calcium phosphate will remove them.

The Dialysis Machine

For treatment of patients in the current protocol we will use the carbon block/filtration bed canister for removal of toxins from dialysate and provision of phosphate whenever dialysate phosphate diminishes below normal. The carbon block/filtration bed will be provided in clean form and incorporated into the dialysate side of a standard NxStage™ System 100 dialysis system. The NxStage System 100 is a commercially available high permeability dialysis system that is used in many hospitals for continuous dialysis of patients in the ICU. It is also used in treatment of home hemodialysis patients, usually on a short daily schedule. The NxStage machine controls ultrafiltration (UF) automatically through use of two dialysate side pumps, two volumetric chambers and an ultrafiltration pump. The NxStage system is used in the hospital setting with pre-mixed 5 liter bags of sterile dialysate (bicarbonate based). At home, it is often used with a 60 liter bag of lactate based dialysate created on site with the PureFlow™ device. Maximum blood flow rate is 500 ml/min and maximum dialysate flow rate is 250 ml/min. In hyperthermic therapy the NxStage dialysis system will be connected in parallel to part of the blood heating circuit, similar to how the BioLogic-HDT was connected in parallel to the blood heating circuit in the previous BioLogic-HT System. However, with the new system we will control blood flow rate through the dialyzer with the blood side roller pump of the NxStage device, at a controlled rate of 400 ml/min. We will therefore be able to remove blood after the roller pump and replace it just before the heat exchanger, in a co-current mode with all other blood flow in the HTA portion. In the BioLogic-HDT system blood flow was passive through the dialyzer, and counter-current to all the other blood flow, creating significant recirculation of blood through the dialyzer. This recirculation is avoided with the Generation II system.

ThermalCore-HT Circuit Schematic

Figure 20:
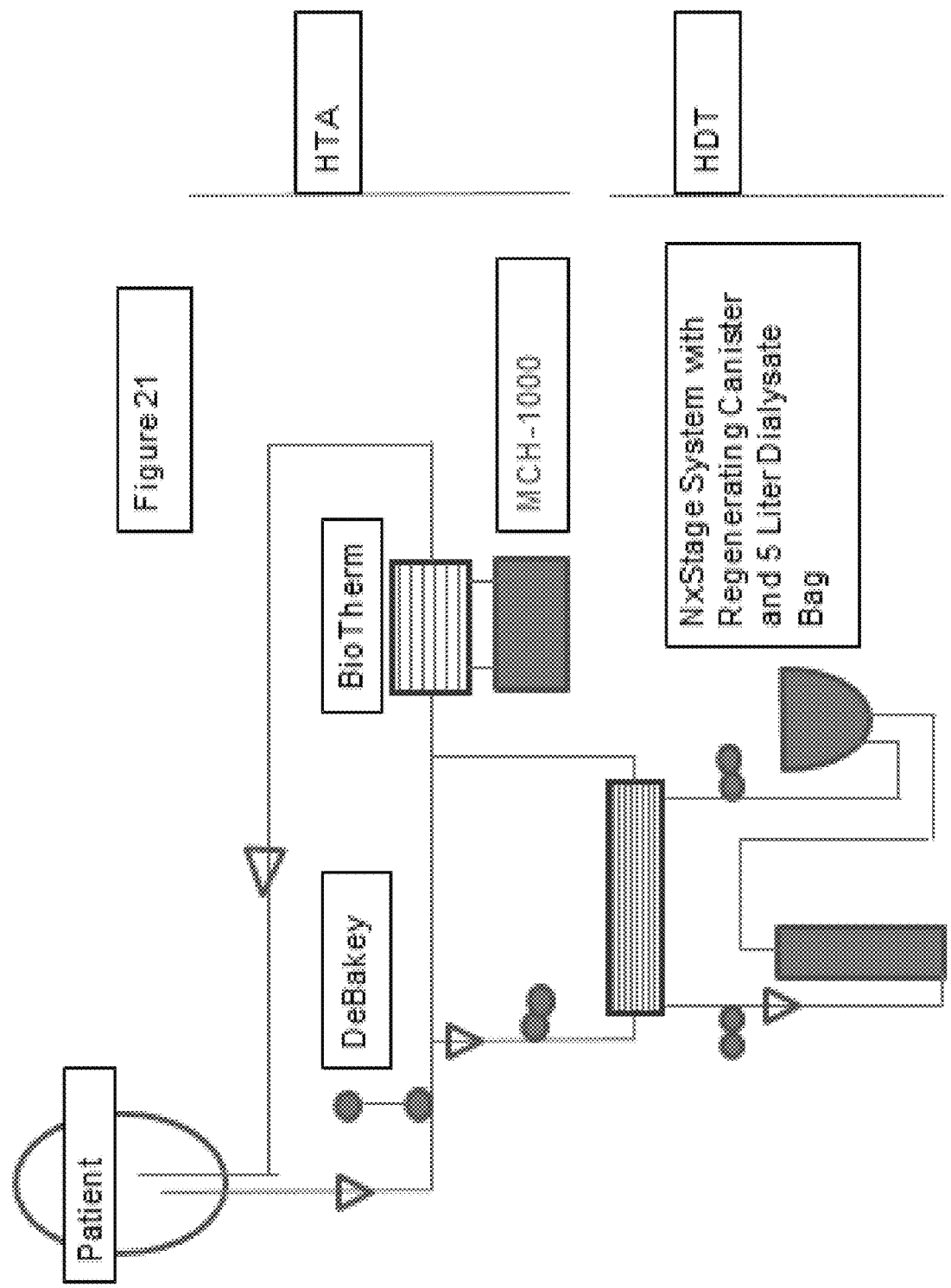
FIG. 20—Diagram of the heating circuit of the Thermal-Core HT System which includes the DeBakey roller pump and BioTherm heat exchanger, and the NxStage sorbent-dialysis system.
Figure 21:
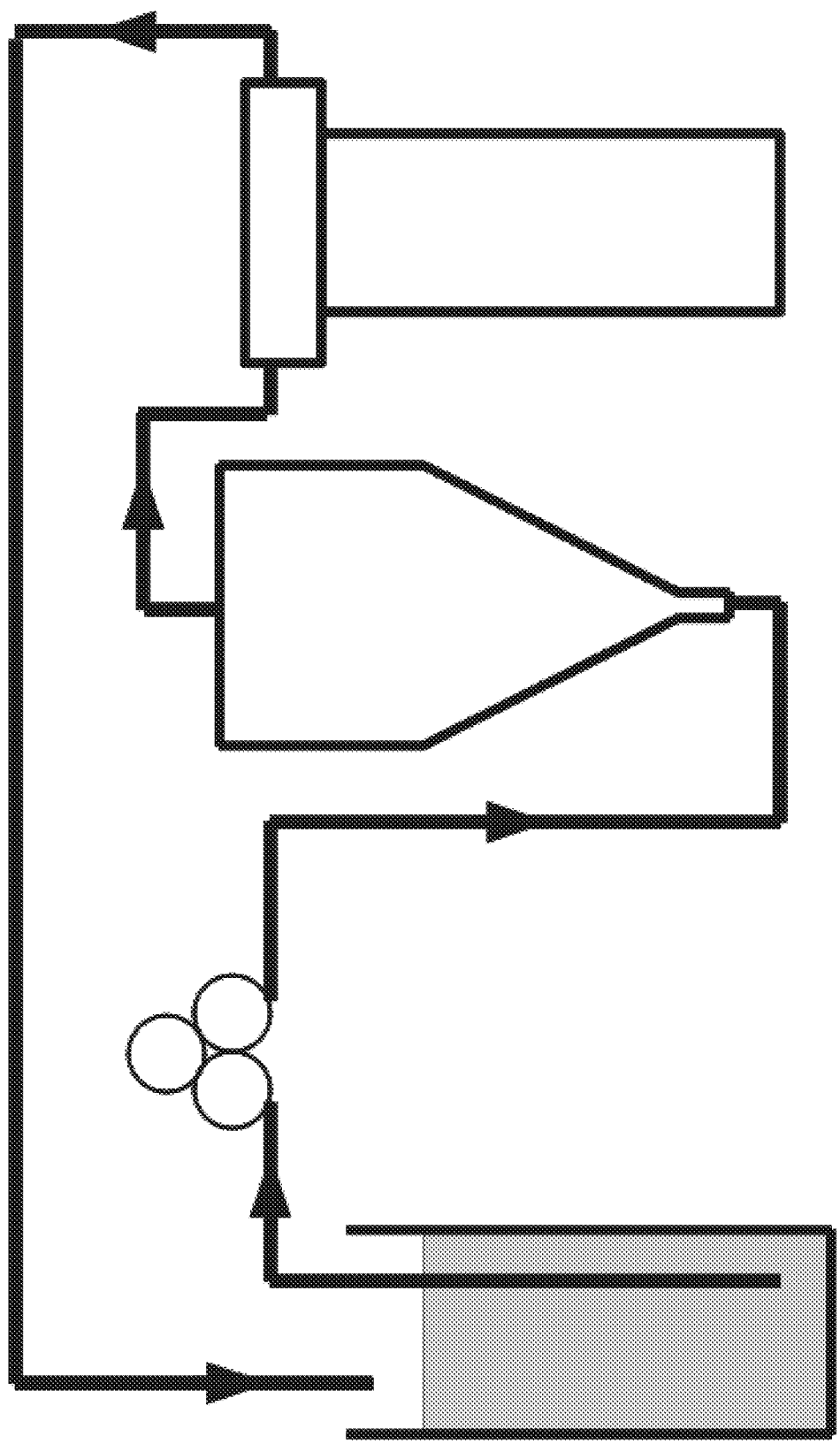
FIG. 21—CCS Test Apparatus
Figure 22:
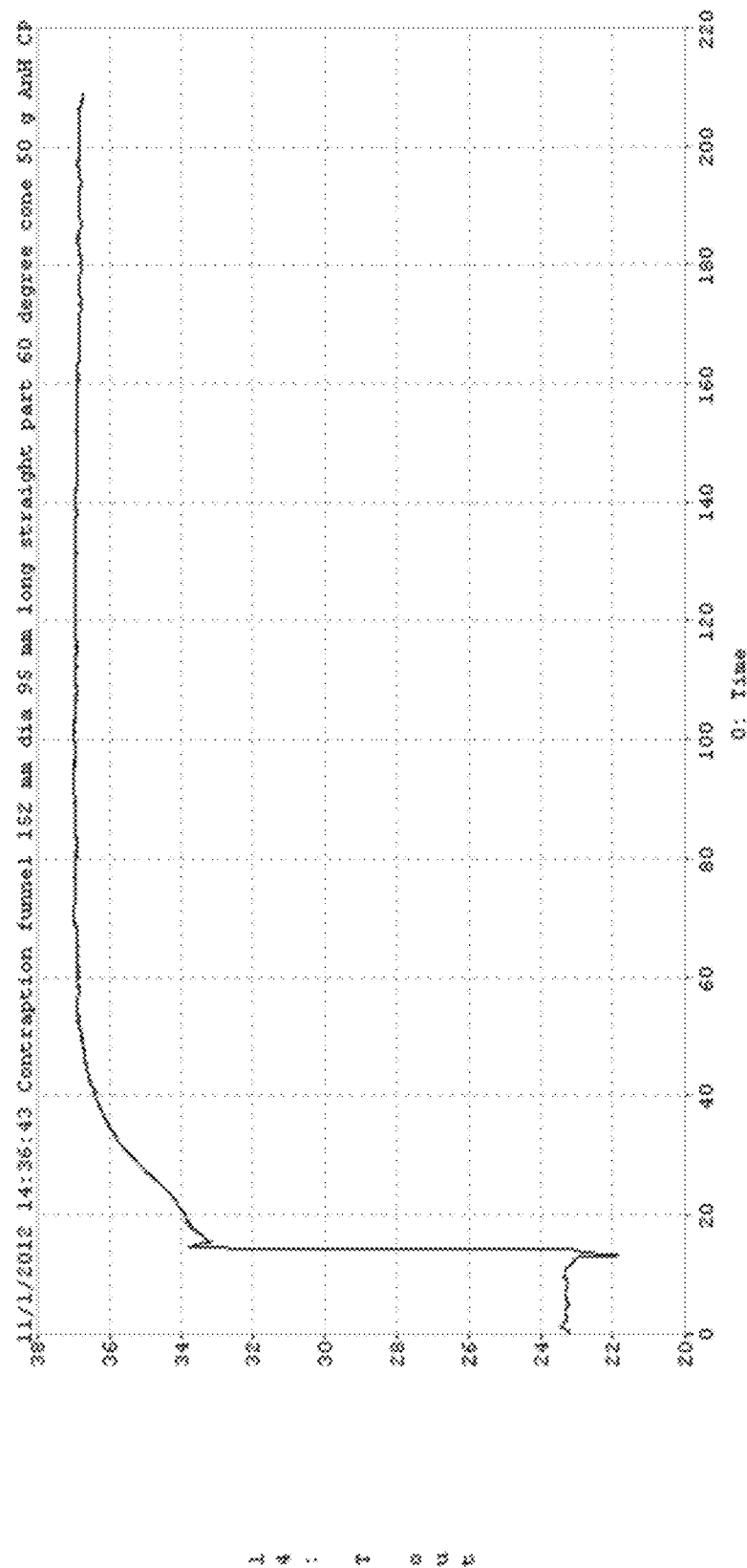
FIG. 22—Outlet Temperature over Time.
Figure 23:
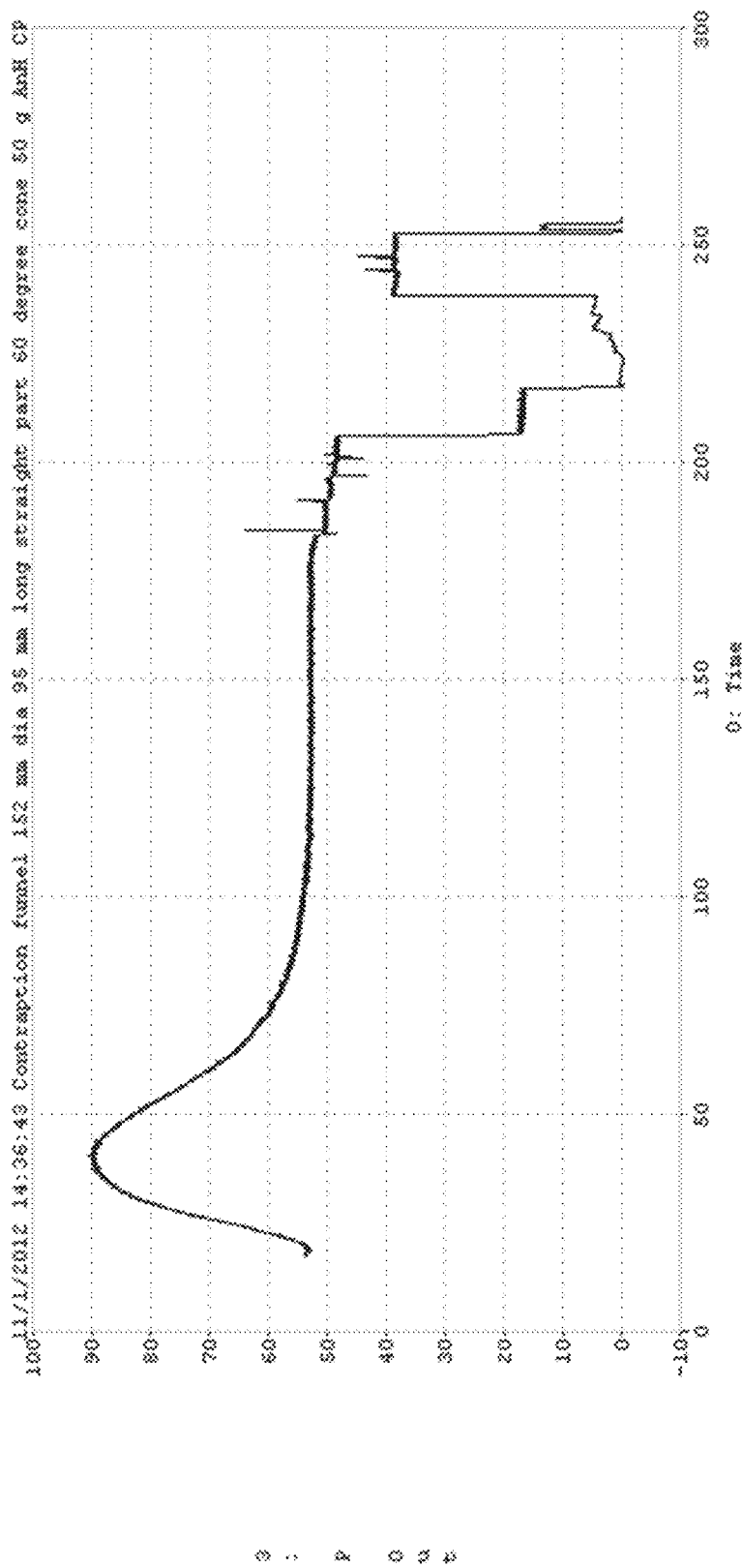
FIG. 23—CBFB Pressure over Time (mmHg)
Figure 24:
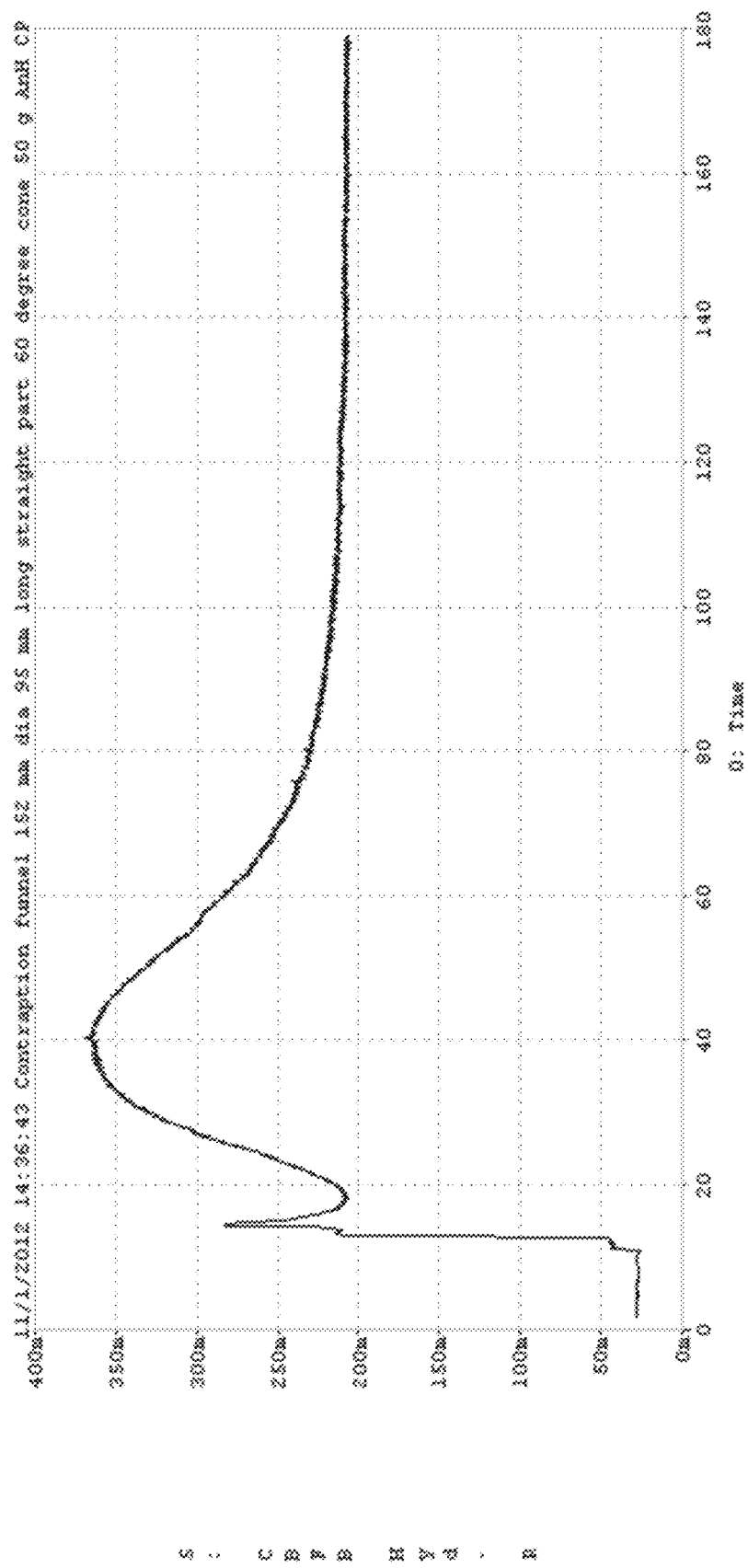
FIG. 24—CBFB Hydraulic Resistance over Time—mmHg/(mL/min)
Figure 25:
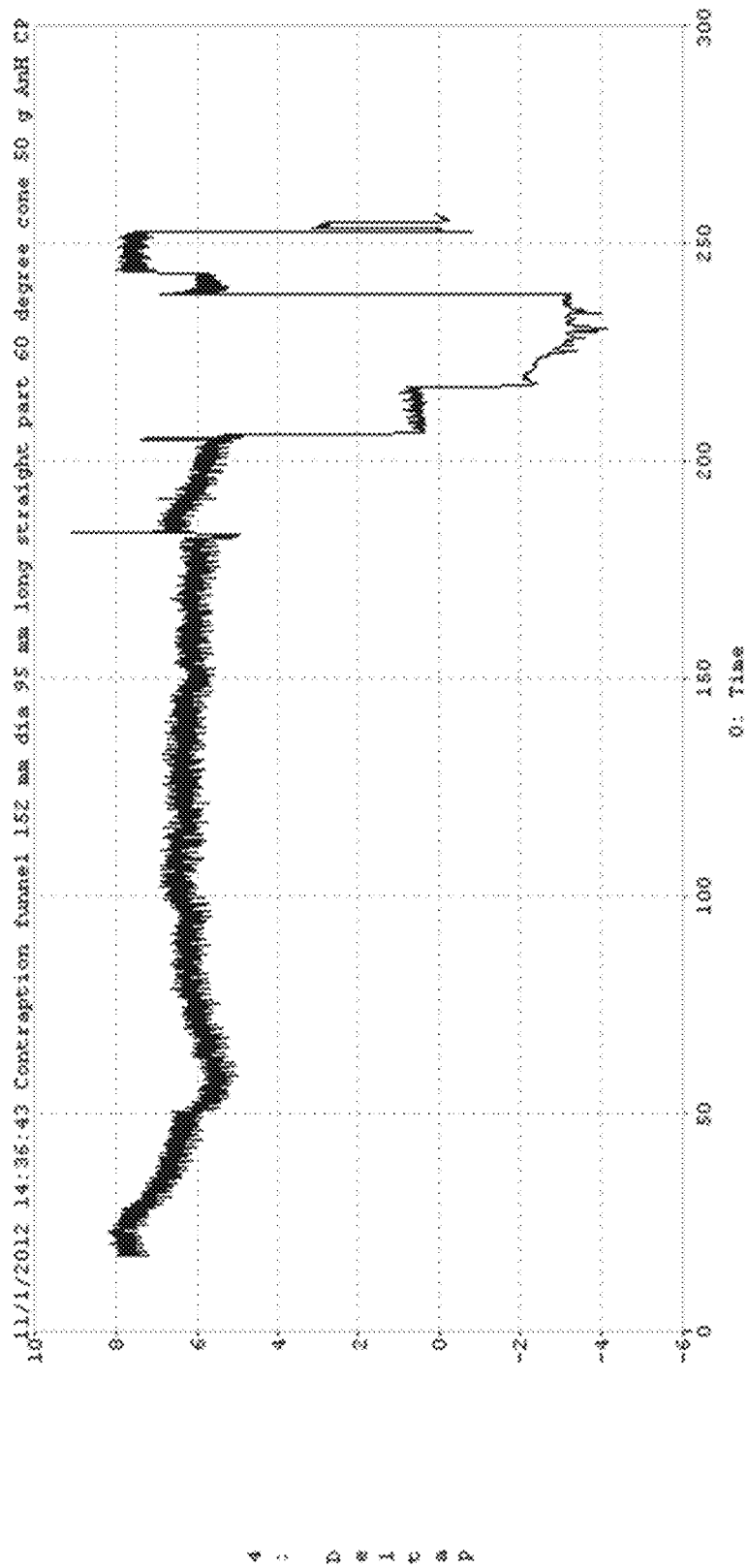
FIG. 25—Cone Reactor Hydraulic Resistance over Time (mmHg)
Figure 26:
FIG. 26—Cone Reactor at Startup
Figure 27:
FIG. 27—Cone Reactor Soon after Startup

Blood flow through the heating circuit will be from 1000-2500 ml/min. The following, FIG. 20, is a diagram of the heating circuit of the ThermalCore HT System which includes the DeBakey roller pump and BioTherm heat exchanger, and the NxStage sorbent-dialysis system.

3.4 the Thermalcore Ht System Operation

With the NxStage system as the HDT circuit we will use 5 liters of bicarbonate-based dialysis fluid. This will provide a larger amount of potassium and bicarbonate than was present in the two liters of fluid in the original HDT circuit, and a greater volume of dialysate for removal of potassium if needed (by using a low potassium concentration in dialysate). The total capacity for balancing electrolytes should be essentially the same as was present with the original HDT circuit containing the electrolyte-balanced polystyrene sulfonate (which remained mostly loaded with divalent cations calcium and magnesium). Changes in calcium, phosphate and bicarbonate concentration will be offset through dissolution of precipitated calcium phosphate (powder), as it was in the original HDT system. We will circulate the dialysate at 250 ml/min, through the dialyzer, through the charcoal block/filtration bed canister, and back to the bag. We will not need a heater in the NxStage circuit, as the 5 liters of dialysate should quickly come to nearly the same temperature as the blood within the patient. We expect to set the ultrafiltration rate of the NxStage circuit to zero, but if it appears the patient has received more fluid than needed, UF could be removed at up to 1000 ml/hour. This ultrafiltered fluid would accumulate in the 5 liter bag, which is used to prime the entire dialysate side of the circuit.

With incorporation of the NxStage System into the ThermalCore HT system, we are using a commercially available and well-proven device to automate the dialysis circuit, monitor ease of blood flow, detect bubbles, control ultrafiltration, and limit blood side chemical changes.

These features and functions are all similar to those that were included in the BioLogic-HT System, but we accomplish these functions using technology that appears much more conventional. The many similarities in function between the original BioLogic-HT System and the current system are demonstrated by the following Comparison Table:

TABLE # 16

Comparison Table of the Original BioLogic-HDT System and the ThermalCore-HDT portions of the Systems:

| Feature | BioLogic-HT | ThermalCore-HT |
| --- | --- | --- |
| Dialyzer | Cellulosic Flat Plate, 1.8 $M^2$ | Polysulfone hollow fiber, 1.6 $M^2$ |
| Blood Flow Rate | 600-800 ml/min with recirculation | 400 ml/min without recirculation |
| Dialysate Flow Rate | 300 ml/min (net out of dialyzer) | 250 ml/min unidirectional |
| Creatinine clearance (in vitro) | 130 ml/min | 150 ml/min |
| Ultrafiltration Rate | 0-1000 ml/hour | Same |
| Powdered Activated Charcoal | 140 grams, Coconut, in suspension | 300 grams, Coconut, supported in carbon block |
| Powdered Calcium Phosphate USP | 50 grams (80 mM), precipitated in bag | 50 grams, precipitated by manufacturer |
| Potassium removal maximum (with zero potassium added to bath, patient K of 6) | 10 meq | 60 meq (from one 5 liter bag, a second bag could be used to contribute more) |
| Potassium donation maximum (starting bath of 6 meq, patient K of 3) | 6 meq | Same |
| Bicarbonate donation maximum (patient bicarbonate of 10) | 40 meq (from 2 liter bag) | Same |
| Phosphate donation maximum (patient phos of 0.5 mM) | 20 mM | Same |
| Bacteriologic Status of dialysate circuit | Clean, not sterile | Same |
| Blood Temperature Monitoring | Outflow of Heater, Inflow Blood Line | Same |
| Patient Temperature Monitoring | Multiple Points | Same |

In terms of function and features, steps of operation, and clinical effects we expect the ThermalCore-HDT System to be highly similar to that used in our prior IDE studies. However, the overall operation will be much simpler.

There are other potential uses for the carbon block/filtration bed technology besides whole body hyperthermia. If the calcium phosphate powder is replaced by an ammonium sorbent such as a cation exchanger like powdered microporous fractionated protonated zirconium silicate (ZS, U.S. Pat. Nos. 5,891,417, 6,579,460, 6,099,737, and published application 2004/0105895), then the carbon block/filtration bed technology should be perfect for treatment of liver failure. If the urease enzyme is bound to the ZS or placed in a layer upstream from it, then the system could effectively treat kidney failure (an anion exchanger would also be needed). If an immune-sorbent is used in the filtration bed and the perfusate is plasma, then various immune diseases might be treated such as lupus erythematosus, Wegener's, rheumatoid arthritis and psoriasis. The charcoal also will bind a number of intermediaries of these immune diseases. Finally, with a sorbent capable of binding endotoxin and TNF (a cytokine) such a system with plasma perfusion could treat the condition of sepsis.

If there is one down-side of the filtration bed, it is that when fluid flow is stopped, the sorbent particles leave the membranes and quickly fall to the bottom of the canister. When fluid flow is re-started there will be some passage of the toxin materials from the bulk fluid through the carbon block, until the filtration bed is re-established by the flow. For toxins of low potency to the patient, this is not a problem. For some toxins such as ammonium created by urease, release to the patient could cause problems. If this is a problem, then there are ways to maintain fluid flow through the filtration bed when blood flow through the dialyzer is stopped. The easiest is to merely continue dialysate flow, even if blood flow is ceased through the dialyzer. Dialysate flow could be bypassed around the dialyzer if such is required.

We have also found that to form a fluidized bed of small particles the flow rate through the CB must be relatively high, such as 400 ml/min for a CB of 2.5" diameter and 10" length. At 250 ml/min the fluidized bed does not form without agitation of the CB and suspension. Further, the formation of the fluidized bed depends on the particle size of the suspension and the density of the particles. For particles over 10 microns in size of reasonably high density such as over 2 gm/cm3, and relatively low flow rate, the fluidized bed may not form well at all. If the fluidized bed does form but becomes too thick, then flow through the CB is very irregular.

There are also many other cases in which, in contrast to the discussion surrounding FIG. 18, powder will not naturally uniformly coat a carbon block, but will form an uneven layer. By using a cone-created fluidized bed, very fine particles which are not contained by the cone reactor will form a uniform layer on the carbon block. As a result, all particles will either be suspended in the fluidized bed or uniformly coat the carbon block. This uniform coating naturally occurs because only freely floating particles will reach the carbon block and uniform flow through the block will uniformly distribute them.

For all of these reasons we have decided to combine the CB and FB with a conical reactor containing a fluidized bed. The fluidized bed will work to perfuse fluid through particles that have too high a sedimentation rate to rise and form a fluidized bed around the CB. Those particles with smaller size will rise and form a layer as FB around the CB, as described below. This layer will be relatively thin and made of small particles, and results in a uniform fluid distribution through the CB.

Section C: Cone Reactor with Fluidized Bed for Use in Combination with CB and FB Introduction The cone shaped reactor is a device to contain a fluidized bed, containing all particles in a suspension with sufficient density and particle size to remain in the reactor during upward flow of fluid. Initial experiments showed that the sorbent calcium phosphate (CP) forms a “cloud” of relatively dense particles, topped by an area of finer particles. It was immediately realized that a cone shaped reactor could permit an equilibrium between the linear flow velocity of the fluid and the settling rate of particles and also allow the fluidized bed to continue to operate over a range of fluid flow rates.

Initial experiments with an Imhoff cone (similar to a funnel with sides 7° off vertical) confirmed this hypothesis. In this experiment, the CP was placed on top of a frit made of a piece of porous plastic with 35 μm nominal pore size. The cone was provided with a lid with which to return fluid to the reservoir. It was found that when fines released by the cone returned to the cone, they gradually plugged up the inlet frit and pressure built up unacceptably. This experiment did, however confirm the basic principle of the cone reactor concept.

At the suggestion of David Carr, a carbon block in an un-modified filter holder was used to catch the fines. This method worked well for both anhydrous particle sizes and for dihydrous CP. The main findings are summarized in Table 1.

TABLE 1

Fluid Velocity vs. CP Bed Height

| CP Type | Flow Rate | Cloud Height | Cone Angle | Fluid Velocity at Top of Cloud (cm/min) |
|---|---|---|---|---|
| Old Anhydrous | 250 | 21.5 | 7 | 3.8 |
| Old Anhydrous | 100 | 14 | 7 | 3.6 |
| New Anhydrous | 117 | 21.5 | 7 | 1.78 |
| New Dihydrous | 86 | 21.5 | 7 | 1.31 |

Also, to determine the limits of cone angles, both anhydrous and dihydrous CP were poured into funnels of various angles, including angles beyond that of the bare funnel by mounting the funnel in a ringstand and tilting the ringstand. The CP was allowed to settle and the funnel surface was examined. Then the funnel was drained at a flow rate determined by gravity and 4.5 mm ID tubing. The funnel surface was then examined again for residual powder. It was found that funnel angles up to 45 degrees off vertical were tolerated, with only a minor dusting of powder on them.

As a result of these experiments, a spreadsheet was created to assist in the analysis and design of cone reactors for CP. To test the validity of the spreadsheet and the functionality of the combination of the cone reactor and carbon block with a coating of CP powder, 3 experiments were performed. We shall call the combination of carbon block with a bed of CP on it (CBFB) and a cone reactor a CCS (CBFB plus Cone reactor System). The output of the spreadsheet is shown in FIGS. 46 and 47.

Analysis also revealed that while a pure cone reactor would work, the large volume of a cone as one goes up in diameter results in fairly useless and large extra volume. Hence, a more volume-efficient cone reactor uses a cylinder on top of a cone, roughly in shape to an unfritted Buchner funnel. That said however, it was found (see Results) that 1-2 cm of headspace in the cone prior to the cylinder seems to reduce fines emission from the effluent. In fact, an “overloaded” cone will naturally have a level 1-2 cm below the cylinder.

With this information in hand, three experiments were performed.

As may be seen in FIG. 21, following the arrows from the reservoir on the left, fluid is pumped using a roller pump to the bottom of the cone reactor. The effluent from the cone reactor goes to the filter holder, thence to the outside of the carbon in the CBFB, then through the carbon block to the center hole and out back to the reservoir. The reservoir was heated to 41+/−1° C., and stirred continuously. Flow and pressures across the two reactors were acquired by a proprietary data acquisition system.

The reactor was an ordinary laboratory funnel with sides a 30° angle from vertical. A cylinder 15.2 cm inside diameter was placed on top of the funnel and sealed with permanently sticky butyl caulk. A top was provided for the cylinder with an O-ring and provision to adjust the height of the top so as to vary the cylinder height and volume. Calculated volumes for the cone reactor were 793 mL for the cone and 905 mL for the cylinder giving a total of 2968 mL for a 5 cm headspace. Each additional cm is approximately 181 mL.

In each experiment, flow was initially set to approximately 250 mL/min. Conditions were varied as seemed necessary or as thought might yield interesting results. The first experiment was designed to test a steady state condition. The second experiment had more of a goal to "break" the functionality of the CCS, and the third experiment was designed to test the interface with the NxStage machine.

250 mL/min was selected as it was thought that this is the maximum NxStage flow; the maximum is actually 200 mL/min.

TABLE 2

Experiment Conditions Summary

| Experiment | Initial Anhydrous CP Load (g) | Initial Flow (mL/min) | Headspace (cm) | Fluid | Remarks |
|---|---|---|---|---|---|
| 1 | 50 | 250 | 9.5 | 0.9% NaCl | 250 mL/min entire run except for short run at 100 mL/min and stop-flow test. |
| 2 | 50 | 262 | 5.0 | RFP-404 | 370 mL/min tested without ill effect. Also tested at 100 and 160 g without ill effect. Fluid was at room temperature (20 C.) until t = 33 min, then heater turned on, set to 42 C. |
| 3 | 33 | 200 | 5.0 | RFP-404 + NaCl | NxStage Machine testing. Machine had pauses which collapsed CBFB bed. |

Figure 28:
FIG. 28—"Mature" Cone Reactor
Figure 29:
FIG. 29—Particle Cloud at Highest Point

In FIG. 28, note how there is a line just below the rim of sealant. That line is the start of the cylinder. The check valve may just be seen above the worm drive clamp at the bottom. It is the black ring inside. The check valve was made of half of a rubber stopper, top diameter 13.1 mm, bottom diameter 10.9 mm, length 14.2 mm, with a long screw to weight it down and keep it straight. Total mass was 3.54 g. The check valve was not intended to stop reverse fluid flow, only keep powder from exiting the cone reactor during flow stop, a job it did well. In experiments omitting the check valve, powder consistently entered the influent tubing at zero flow. It should also be possible to use a clamp around the tubing if the screw extends below the cone into the tubing. The temporary clamp retains powder during shipping. A similar scheme can be used at the outlet. In production units, other refinements are possible such as using a plastic rod instead of a screw and scoring the plastic rod whose end is attached to the tube. The user bends the tube to break the rod at the score to release the check valve for operation.

Figure 30:
FIG. 30—Reactor at End of Experiment 1
Figure 31:
FIG. 31—Early CBFB Flow Uniformity Test

Observe in FIG. 30 how much lower the suspended CP bed is. Much of the CP has gone to the CBFB. CP not retained by the cone reactor was deposited on the carbon in the CBFB as seen in FIGS. 31 and 32.

Figure 32:
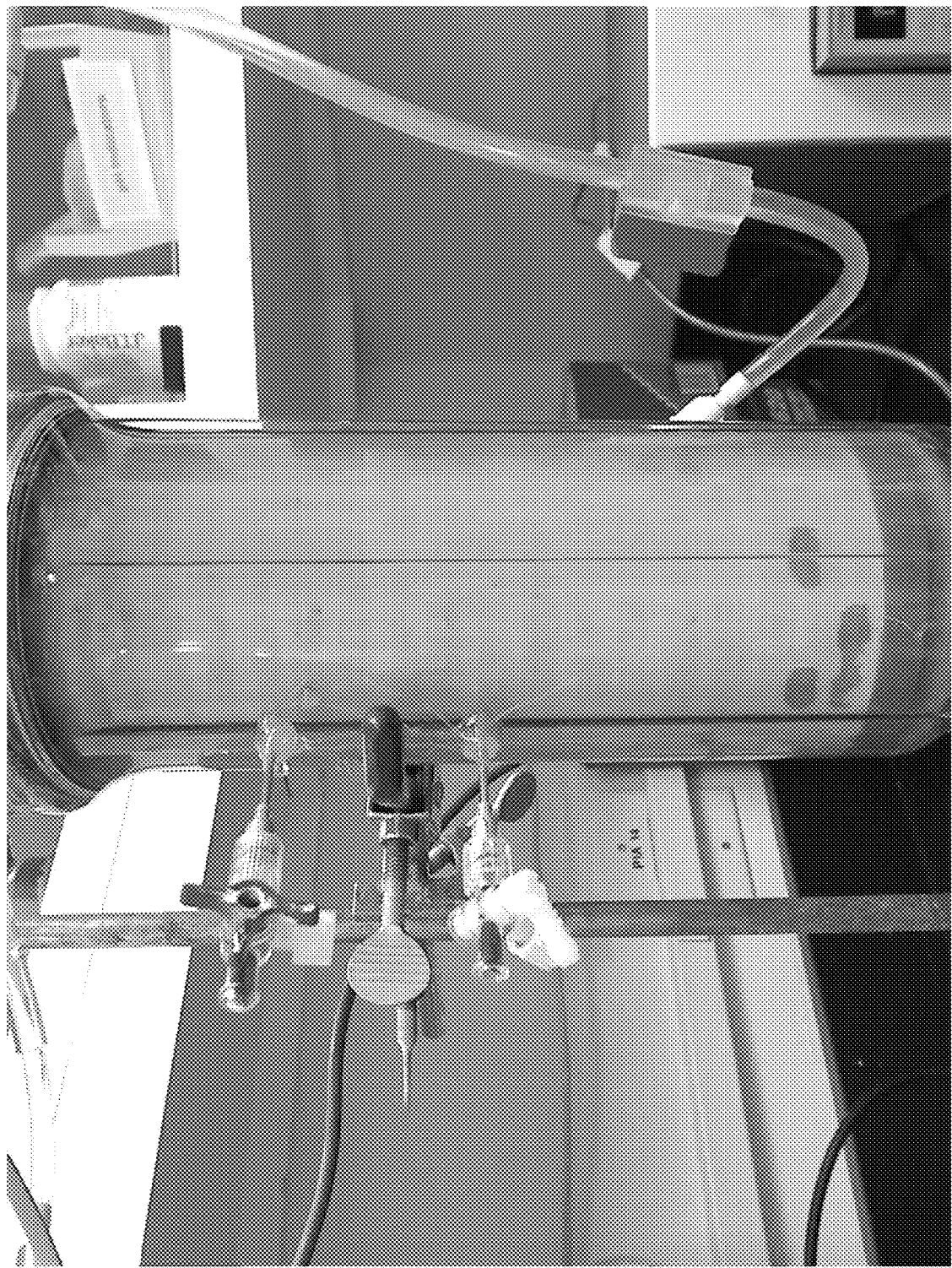
FIG. 32—CBFB Flow Uniformity Test at End of 4 h Run

FIG. 32 shows that no harm had come to the CBFB's flow uniformity, but during a stop-flow test, some CP was not retained on the carbon and fell to the bottom.

Significant observations included the ability of the CCS to perform well at 100 mL/min, and partly re-start after a stopped-flow condition.

At the end of experiment 1, the CP in both the CR (Cone Reactor) and CBFB were washed into beakers. The supernatant was sucked off after an overnight settling time, then the remaining substance dried. The CBFB was found to contain 12.5 g and the CR 32.8 g, including a 5 g loss. Thus, the CBFB ended up with 28% of the CP by weight.

The "natural" cloud height was about 1.6 to 2.2 cm below the start of the cylinder. This is not a "hard and fast" rule—due to the stochastic processes involved, there is never an actual cessation of particle carryover to the CBFB.

Experiment 2

Figure 33:
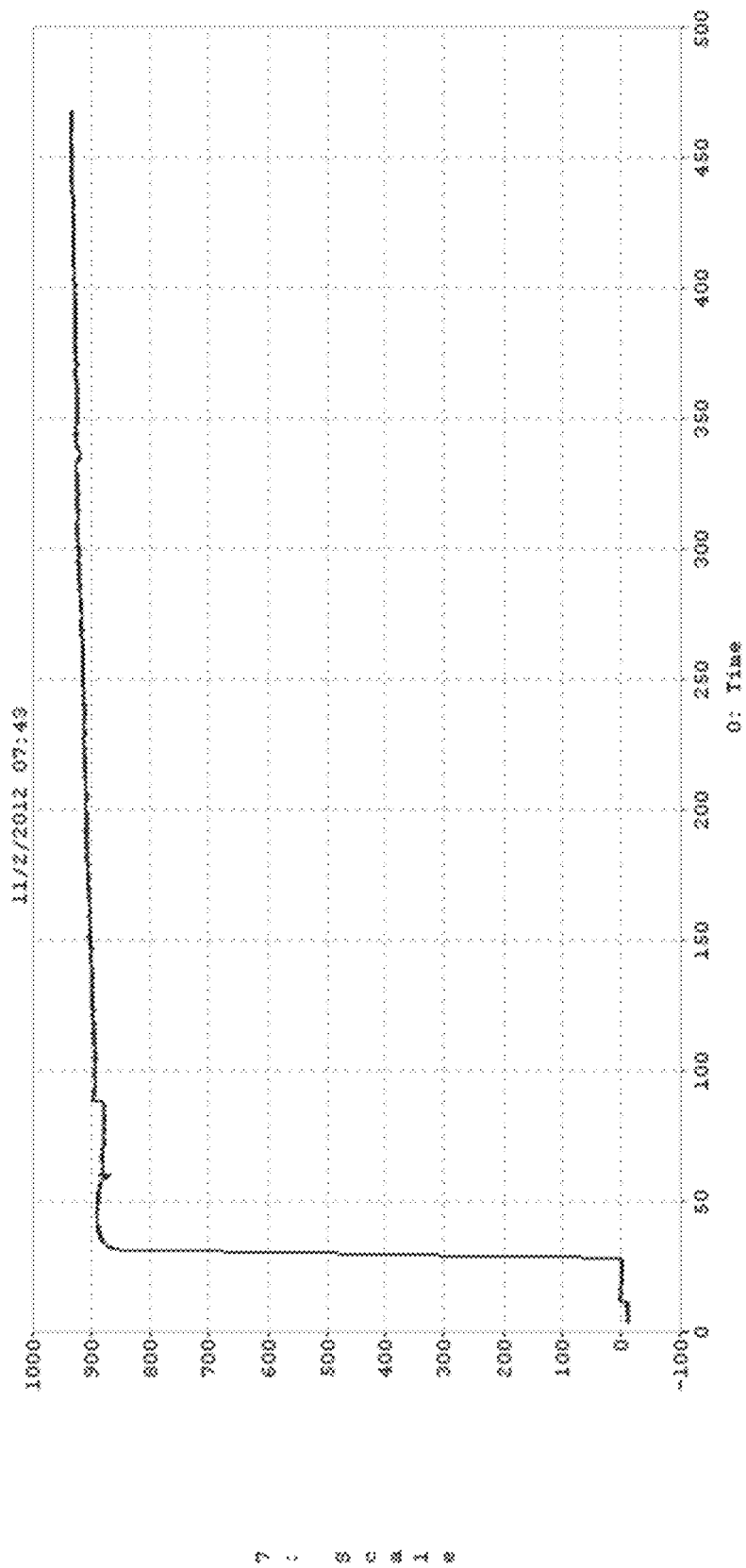
FIG. 33—CBFB Weight Gain Over Time
Figure 34:
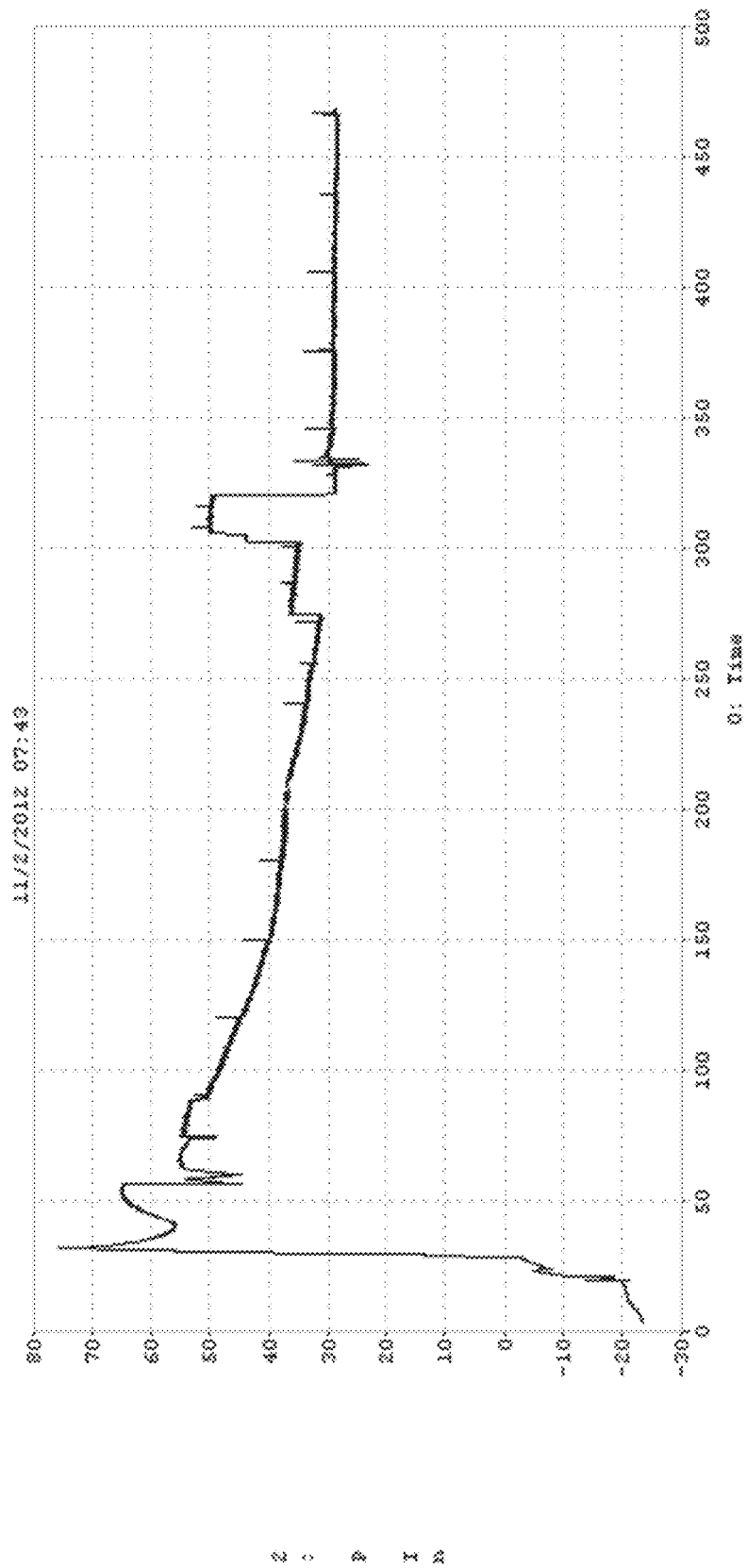
FIG. 34—Experiment 2 Total Inlet Pressure over Time
Figure 35:
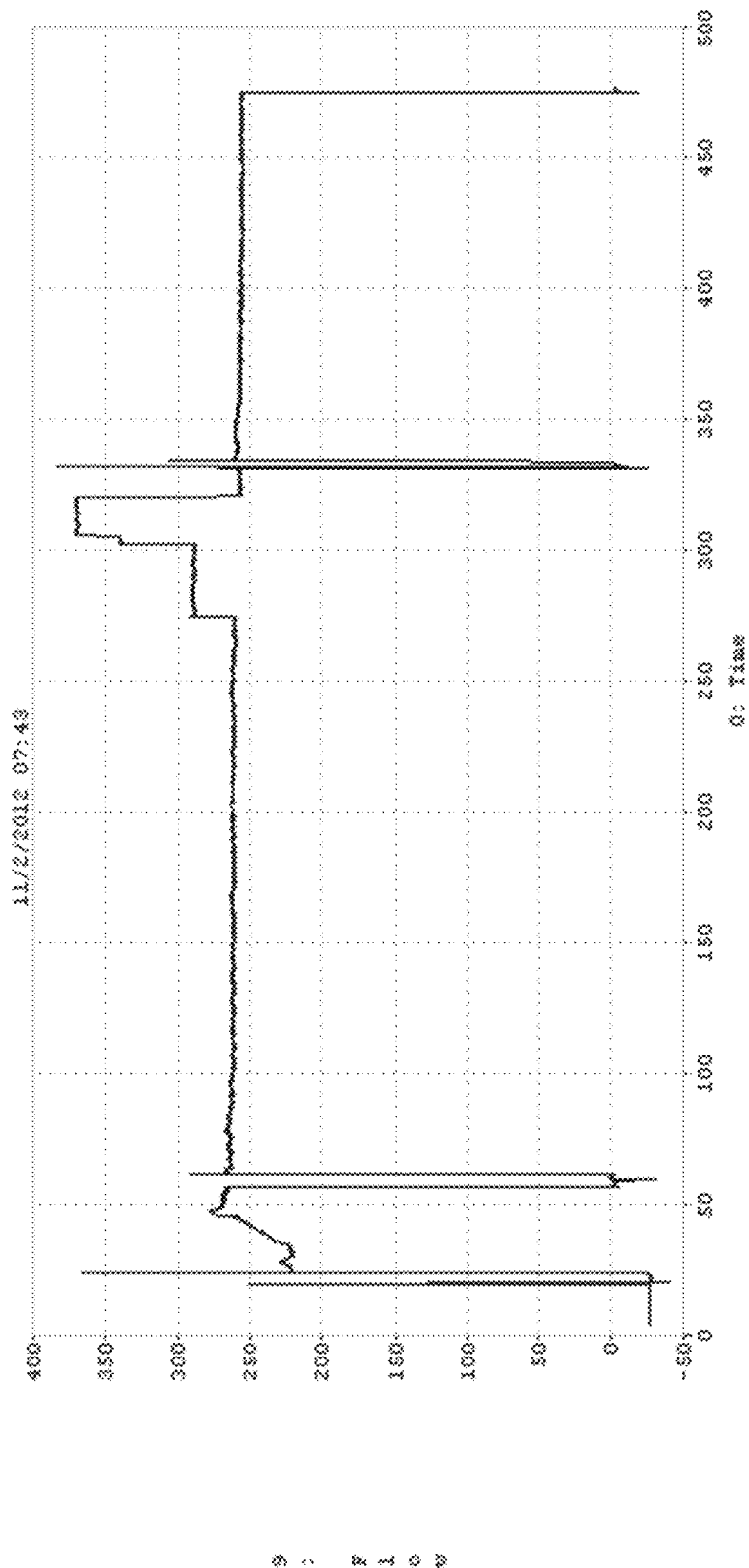
FIG. 35—Experiment 2 Flow

As may be seen in FIG. 33, the fluid volume of the CBFB is not more than 935 mL. The weight steadily increases; the proportions due to powder accumulation and air emission are not known.

Figure 36:
FIG. 36—Cloud In Cylinder Acts As Particle Size Classifier
Figure 37:
FIG. 37—CBFB Flow Uniformity

Significant observations in Experiment 2 included:
Change in salt solution from NaCl to RFP-404 had no effect
Change in startup temperature from 42° C. (Experiment 1) to 20° C. (Experiment 2) had no noticeable effect.
CP could be slurry loaded, but larger particles remained in pump tubing for the duration of the experiment.
The ability to successfully slurry load an additional 50 g at t=60 minutes for a total of 100 g and at another 60 g at t=111 minutes for a total of 160 g, with an increase in cloud size and particle carryover to the CBFB, but without any drastic effects.
The ability to operate at 50% greater than design flow rate with only additional particle carryover.
In the event of an "overload," where the cloud extends into the cylinder, the cylinder essentially becomes a "particle classifier" as seen in FIG. 36.
Worst case CBFB powder load did not impair uniform flow through the carbon.
Increasing CP load does significantly increase cloud size.
The final CP mass in the CBFB was 28.19 g, and in the CR 131.4 g. Loss was less than 0.5 g. The percent of CP in the CBFB was 18%, and in the CR 82%.

Experiment 3—NxStage Machine

This experiment was primarily designed to test the interface with the NxStage machine. One objective was to simply test overall functionality—would the two systems work together with a significant safety margin.

Figure 38:
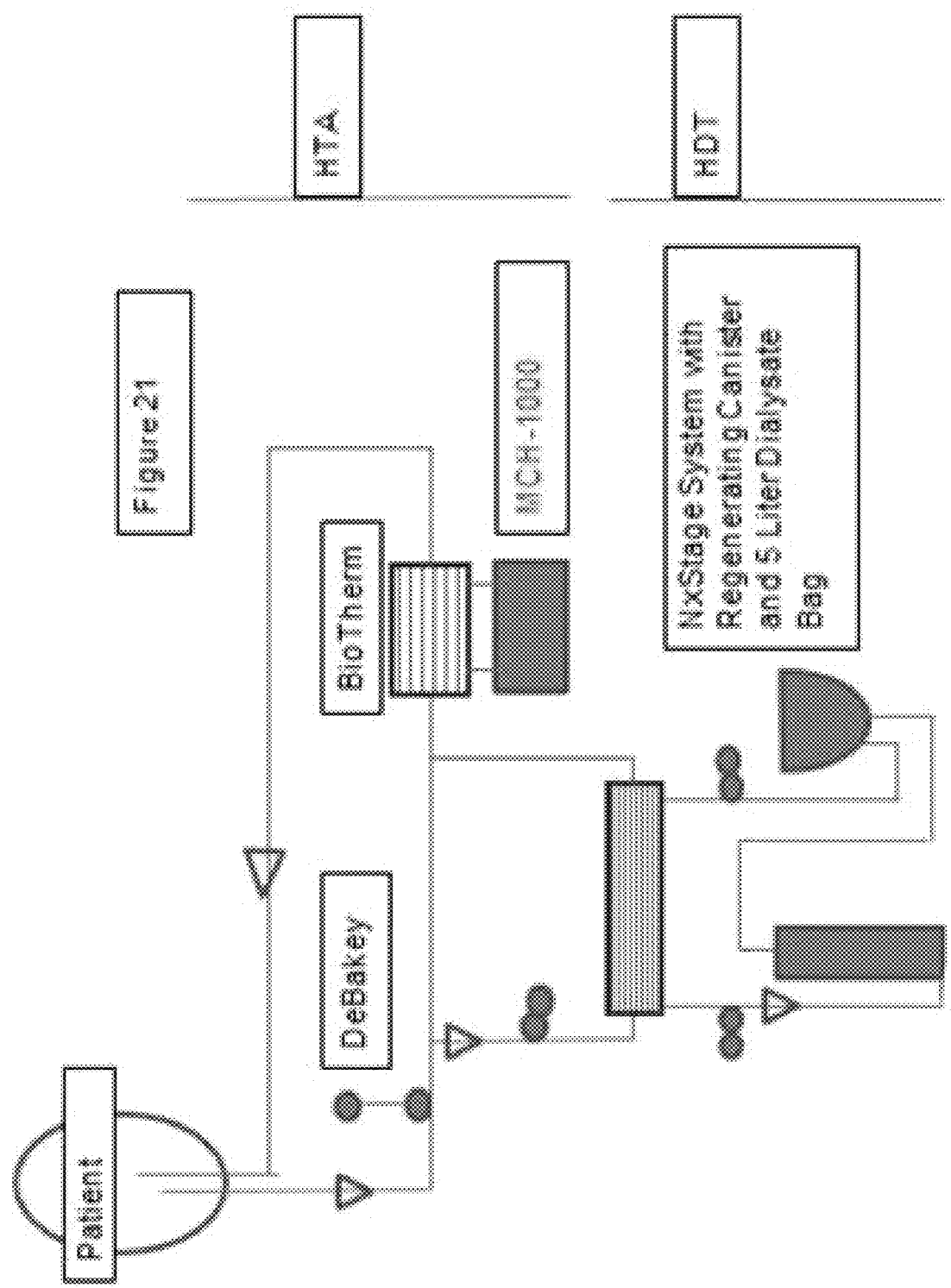
FIG. 38—Experiment 3 Setup

In FIG. 38, The box denoted by the red arrow includes a CR followed by a CBFB. The MCH-1000 and Biotherm were simulated by a simple resistance of about 80-120 mmHg. Flow through the CCS was 200 mL/min. Flow through the simulated Biotherm/MCH-1000 was typically about 754 mL/min.

Figure 39:
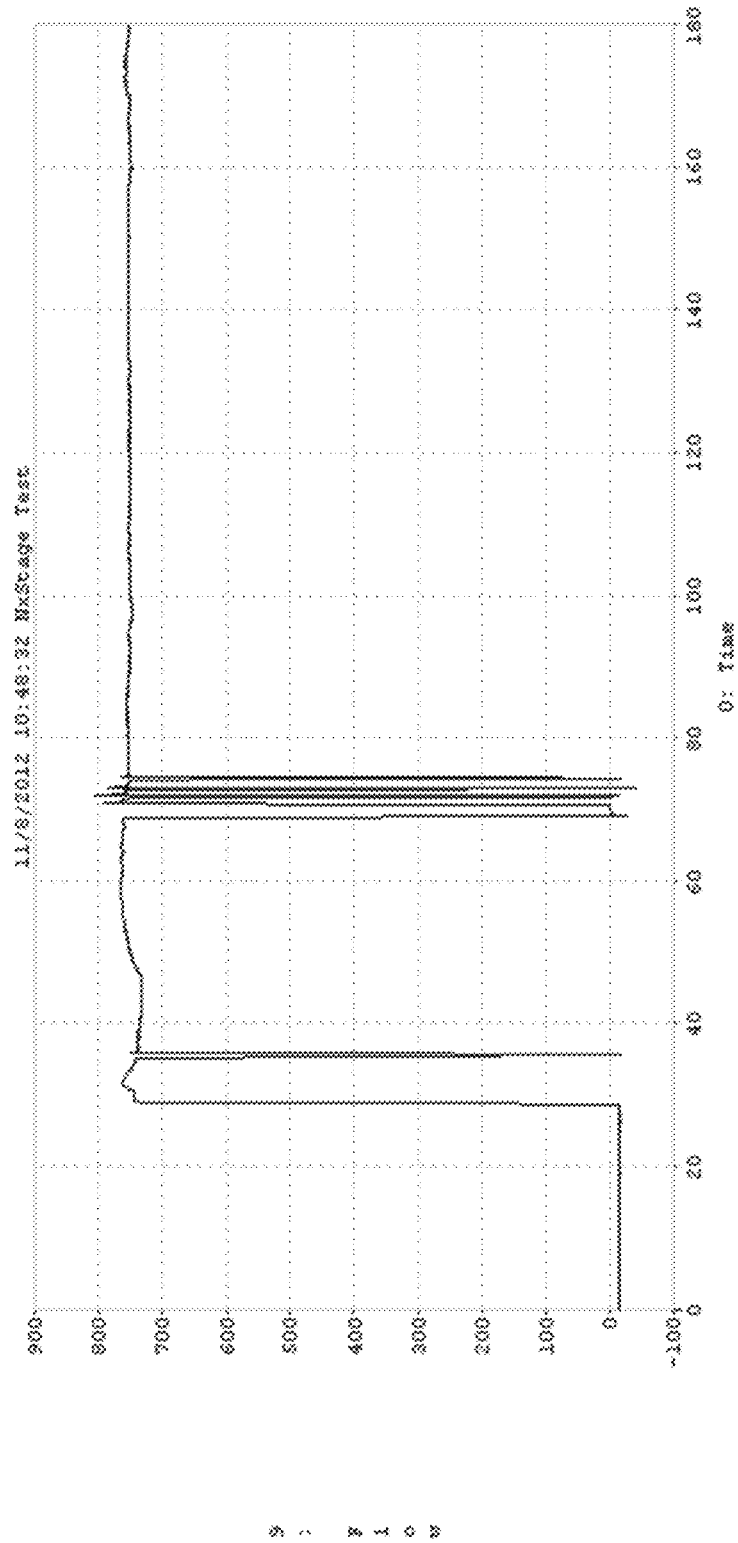
FIG. 39—Experiment 3—Simulated Blood Flow through Biotherm/MCH-1000 over Time
Figure 40:
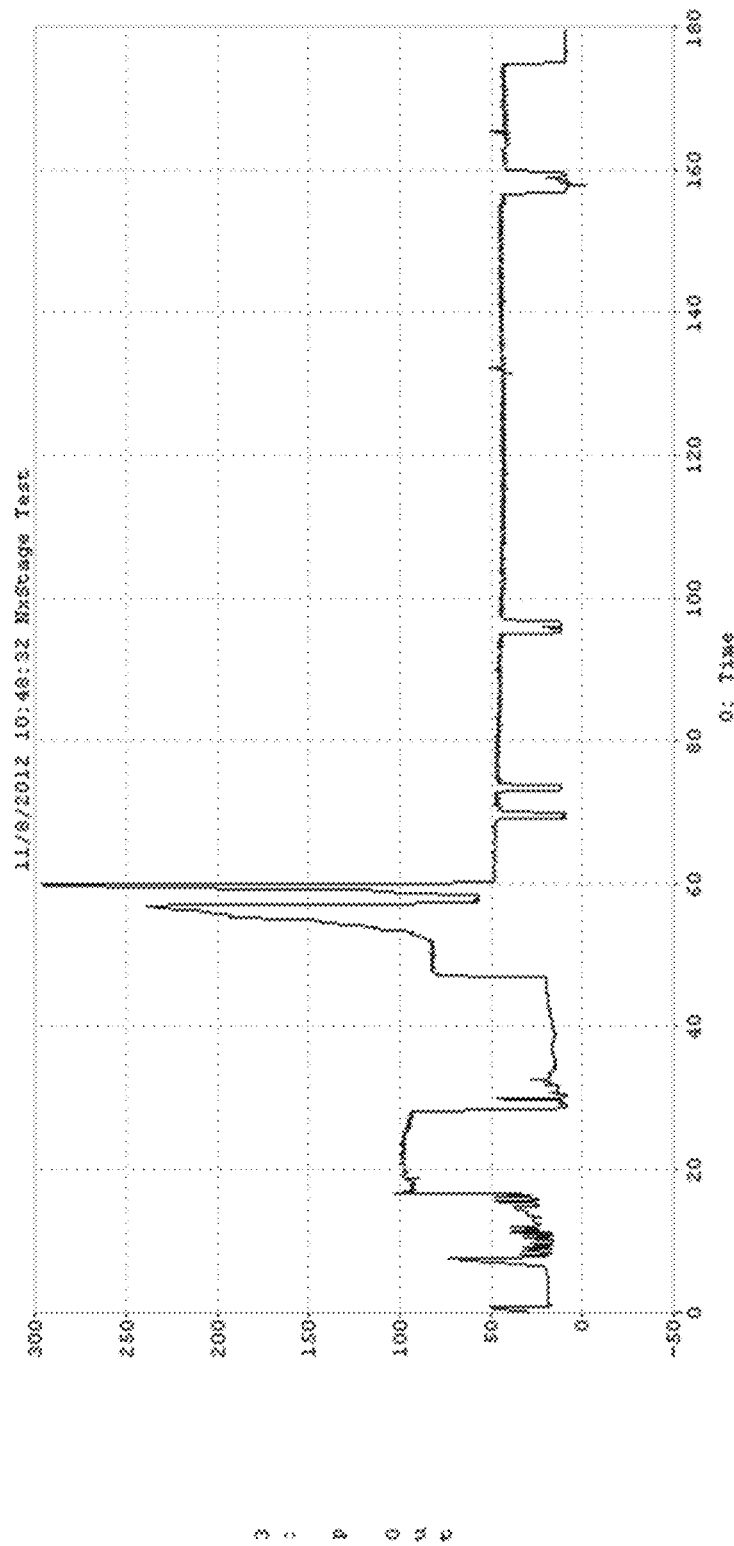
FIG. 40—Experiment 3 CBFB Inlet Pressure over Time
Figure 41:
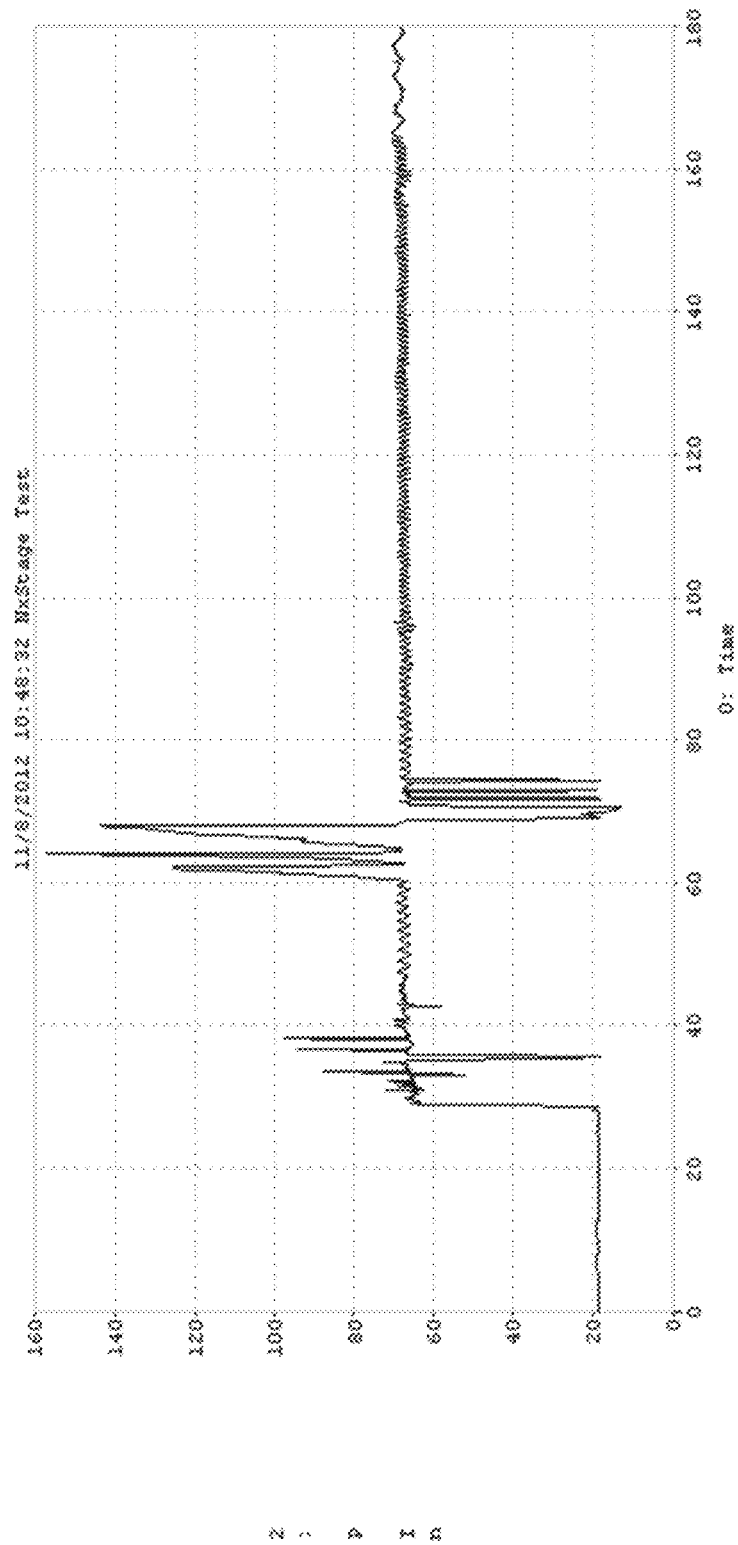
FIG. 41—Experiment 3 "Blood" Pressure over Time

To test the ability of the NxStage machine to tolerate the CCS with a good safety margin, three tests were performed, which, along with periodic machine starts and stops will explain FIGS. 39, 40 and 41.

In the first test, an adjustable flow restrictor was placed in the CBFB effluent line. The effects may be seen at t=50 to t=60 in FIG. 40. The NxStage machine did not give any alarms or error indications. The approximate 300 mmHg limit was the operator's comfort limit.

In the second test, note in FIG. 38 that both the venous and arterial lines are essentially at the same pressure. A flow restrictor was placed at the outlet of the blood line (returned to the "patient"). The effects may be seen from t=60 to t=68 in FIG. 41. The machine generated alarms at 125, 156 and 143 mmHg. The reader is cautioned that the machine algorithms with respect to rise and fall times, time delays and limits are not known and should be determined from the manufacturer.

In the third test, the main blood flow pump was suddenly turned off or on, as may be seen at t=69 to t=75. In all cases, the pump could be suddenly started without a response from the machine. However, if the pump was suddenly stopped the machine would generate a non-fatal alarm. The pump could be stopped by a ramp-down over a period of very approximately 3-5 s without generating an alarm.

Figure 42:
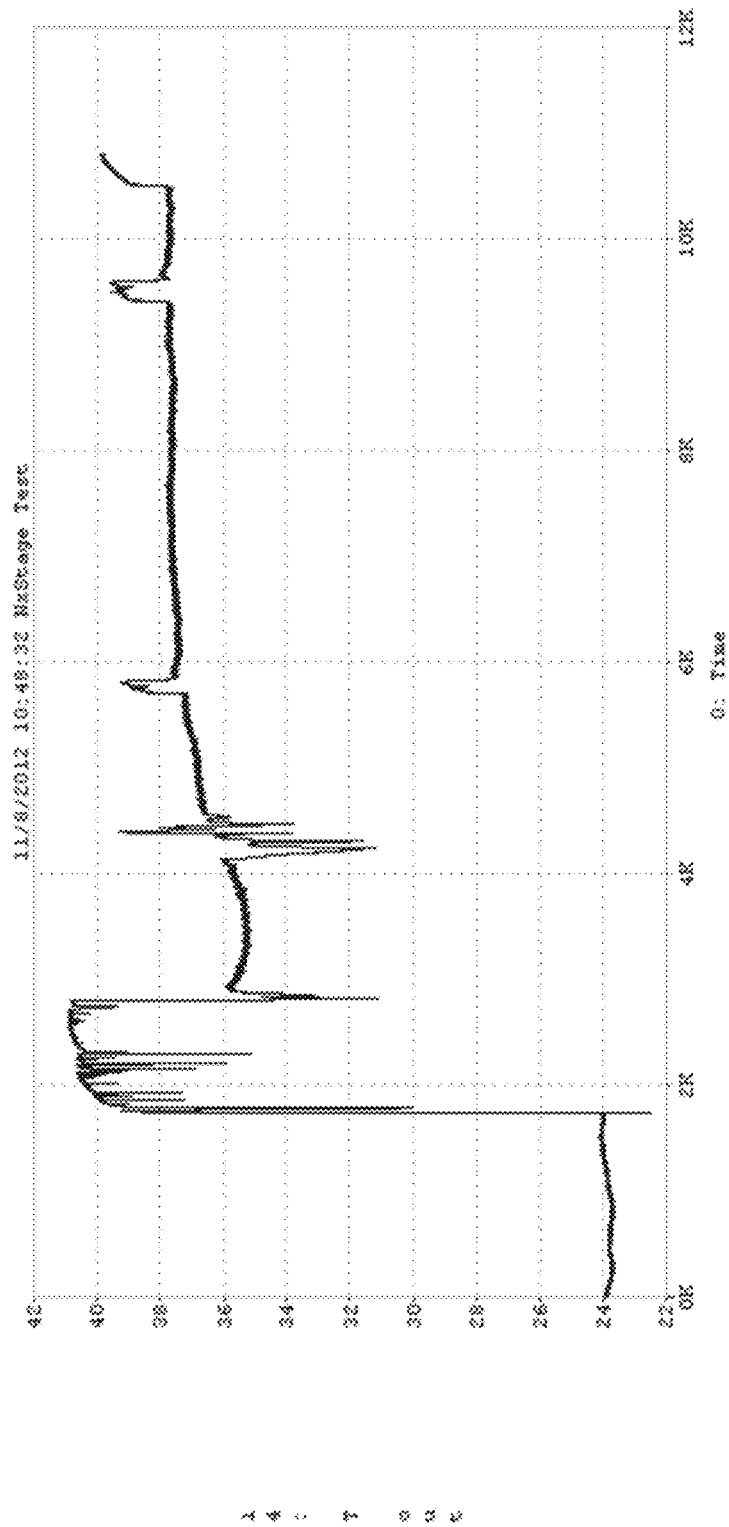
FIG. 42—NxStage Temperature—Trace is Output Temperature of "Blood" to Reservoir

The NxStage also never complained about the temperature of the blood. See FIG. 42.

Three times however during the final 115 minutes of the experiment, the NxStage machine stopped dialysate flow. The duration and spacing of these pauses is apparently random. During the final pause, the CP bed on the CBFB collapsed. At no time was uniformity of flow impaired, but unused CP was left at the bottom of the filter holder.

The CP level in the funnel was noticeably lower than in earlier experiments. Unfortunately, the measurements are lost due to a change in the funnel configuration that was overlooked.

NxStage Operating Notes

The NxStage machine has a maximum DFR of 200 mL/min (recently increased to 400 ml/min).

The return from the CCS needs to go to a separate bag port than the main port to avoid adjacent lines ingesting air. It would also appear helpful to raise this port slightly to keep air well away from the main port. This will require a dual-male luer connector not provided with the disposables kit from NxStage.

It is necessary to break the "frangible seal" on the extra bag port.

The line with the green clamp needs to be connected to the bag.

Recommendation

Figure 43:
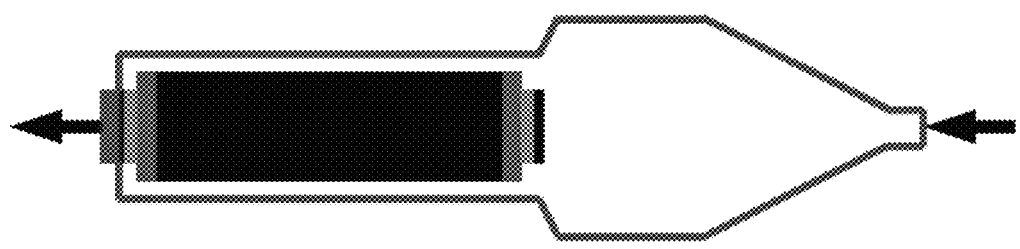
FIG. 43—Unitary CCS

FIG. 43 (not to scale) is a schematic of a significant refinement of an idea suggested by Dr. Steve Ash. The issue with pauses can be eliminated if the falling CP is returned to the cone reactor. Additionally, the number of modifications to the original CBFB system have become sufficiently extensive as to warrant a fully custom unit. In FIG. 43, the inlet check valve is not shown. The cone plus cylinder version of the cone reactor is used. Directly on top of it is a carbon block to create a CBFB. The lower, inner hole of the carbon block is plugged. Flow begins at the bottom, proceeds to the carbon area, goes through the carbon into the inner hole in the carbon and out the top outlet. It may be found expedient to fill the bottom lip of the carbon filter end cap to keep it from trapping falling CP. Alternatively, a block without an end cap may be used and a blank plate substituted.

Detailed design of an actual CCS as shown in FIG. 43 must await one or two additional experiments and work authorization.

Conclusions and Summary

Definition: CCS a combination of a CBFB+a Cone Reactor System.

Evacuating the CBFB is may be contraindicated for some applications unless it is filled off-line. The CBFB may thus be either filled off-line or shipped filled with liquid. In the latter case, the CBFB needs to be well shaken before use.

A CCS, or CBFB may possibly need to be placed on the floor or a table to avoid disturbance due to machine vibrations. Excessive vibrations from some machines could disturb the filter bed.

Cone reactor hydraulic resistance is negligible, about 10 mmHg at 250 mL/min. Fittings will do that. (Note that a 31 inch height difference in water levels produces about 60 mmHg pressure differential.)

There should not be a distributor in a cone reactor. A check valve consisting of an elastomeric plug with a long rod extending into the inlet tube acts as a weight and retainer. This simple method keeps powder out of the lines during shutdown. A clamp on a tube can hold the rod tight against the funnel inlet to keep powder contained during shipping. Other methods are possible as well.

Effective dwell time is some fraction, around 0.8 of cone volume, not entire reactor volume, divided by flow.

A cone reactor performs well at any flow which places the cloud top less than about 2 cm of top of cone. In this case, the filter bed will be relatively thin.

Higher flows push the cloud into cylinder. The cylinder then acts as a classifier and retains larger particles while sending smaller ones to CBFB. In this case, the filter bead will be relatively thick.

A good length of time, about 3 h is required to fully evaluate a CCS. This is due to the statistical nature of fluid and particle flow. This does not imply that the adsorption kinetics of the powder change significantly during this startup time.

Particle transfer is a function of fluid mechanical and thermodynamic probabilities, as well as the particle size distribution. The situation is analogous to water in a pan on the stove. Eventually it will evaporate. Turn on the gas and it will boil. But the process is essentially the same. Thus, particles are continuously, at some rate, transferred from the CR to the CBFB.

Cloud volume, to a large degree, is a function of the amount of CP loaded into the system.

At end of experiment 1, 50 g of CP put 13 g on the CBFB, leaving the rest (72%) in the CR. (12.5 g/32.8 g=~28% in CBFB, 72% in CR—~5 g lost). In the second experiment, 18% was in the CBFB and 82% in the CR. In the third experiment 12.5 g was on carbon, and 34.6 g in CR, for 27% and 73% respectively.

Since the CBFB receives the smallest particles from the CR at a slow rate, the buildup on the CBFB is uniform. Flow is uniform through the block.

Due to the stochastic nature of particle retention and transfer, "overloads" of the CCS, whether from excessive flow rate or excessive CP load, smoothly transfer CP mass to the CBFB at an increasing rate without sudden breakdowns of the process. This assumes that nothing is grossly undersized.

Depending upon schedule, it is possible that further refinements may be made in the design. E.g., it is not known at what point the CBFB becomes actually overloaded and fails to provide uniform distribution.

CBFB resistance goes up initially, then down with time. This is likely to be a function of fluid temperature, possibly from changes in fluid density or increased Brownian motion. Particle dissolution could also be a factor.

The 9 to 11 μm particle size Anhydrous CP seems to have a fairly wide distribution. Some particles remained in pump tubing during slurry fill.

Under some conditions, slurry fill of powder may be possible with very fine powders. This may be useful if a powder must be added to an already running system.

A cone reactor may be restarted after 25 minutes.

A CBFB with a light coating will start falling off after about 25 minutes after a stop-flow event. Data suggests that hold-up time may be a function of trapped air continuing very small flow for a time.

Comparing dwell time to dissolution data indicates reasonable feasibility.

Crude estimate of CP needed: 250 mL/min*60 min/h*3 h/1000=45 L. 45 L*0.2 g/L=9 g. Another source gives 0.316 g/L at 38° C., for 14.2 g. Using 50 g given to FDA, corrected for molar ratios gives a dihydrous load of 63.5 g, which should be enough.

The combined CCS of FIG. 43 has significant advantages and may be easily manufactured by any competent machinist in prototype quantities or in large quantities by normal plastic injection or blow molding.

Section D: Prior Art use of a Suspension Powdered Sorbents for Dialysate Regeration, the BioLogic Series of Devices The following is a description of prior art for using powdered sorbents to regenerate dialysate in an extracorporeal circuit. The prior device was the BioLogic-HDT™ system, with a suspension of powdered sorbents which passed directly through a plate cellulosic dialyzer.

The BioLogic-HDT™ System

An important advance in whole body hyperthermia came with the use of a dialysis system with sorbents to remove various organic toxins and to limit changes in various electrolytes such as phosphorus and bicarbonate during treatment. This was accomplished in our prior studies of PISH through use of an adaptation of the BioLogic-DT (Liver Dialysis) machine. The DT machine had a suspension containing activated charcoal powder to remove organic toxins, and a sodium-loaded cation exchanger powder (polystyrene sulfonate, PSS) to remove small amounts of potassium and ammonium. In the HDT system we also precipitated 80 mM of calcium phosphate within the sorbent suspension (50 grams). Through dissolution, the calcium phosphate precipitate would increase the phosphate level in dialysate if it was lowered by a decreasing phosphate concentration in the blood. We also changed the loading of the cation exchanger so that it was in equilibrium with the normal plasma levels of potassium, magnesium, calcium and hydrogen. In this way, the PSS would release a small amount of these cations into dialysate if concentrations fell below normal, and absorb a small amount if the concentrations rose above normal. The automatic control of changes in dialysate chemistry would then offset and diminish changes in chemical concentration in the blood during whole body hyperthermia treatment (WBHT) therapy (called perfusion-induced systemic hyperthermia (PISH) if perfusion-induced).

Description of the Biologic-HDT Machine

The following is our description of the Biologic-HDT dialysis circuit from our 1996 Food and Drug Administration Investigational Device Exemption (IDE) (G960257/S) for a clinical trial of WBHT in treatment of patients with advanced lung carcinoma (page 6 of the Operator's Manual):

"The dialysate side contains a 2-liter suspension of powdered sorbents (charcoal and cation exchanger) which circulates between the dialyzer and a bag, and controls chemical composition of the dialysate according to binding characteristics and loading of the sorbents. The ultrafiltration rate is measured by changes in weight of the sorbent bag; simple algorithms adjust the ratio of blood inflow and outflow cycle times to obtain the minimal ultrafiltration rate, and automatically reinfuse fluid to the patient to obtain exactly the prescribed weight increase or decrease during treatment. The sorbent components of the BioLogic-HDT machine were as follows:

1. 200 grams of cation exchanger, pre-loaded with sodium, calcium, potassium, hydrogen, and magnesium in amounts to maintain equilibrium with normal blood concentrations,
2. 140 grams of powdered activated charcoal with 80 mMoles of calcium phosphate (50 grams) precipitated on the surface to dissociate whenever the surrounding solubility product is lower than the normal blood solubility product,
3. Sodium bicarbonate and sodium chloride in physiologic concentrations,
4. Flow-inducing agents,
5. And glucose absorbed to the powdered charcoal to dissociate and maintain normal or slightly high blood glucose.

Additional calcium chloride is infused into the venous return line of the HT at a rate necessary to maintain a normal blood calcium concentration. In-room analysis of plasma phosphate prompts addition of disodium phosphate to the sorbent suspension whenever plasma phosphate decreased below normal levels (which happens only during high temperature WBHT). From previous studies, a solution of disodium phosphate and sodium bicarbonate was devised which, when added to the sorbent suspension during high-temperature PISH, should result in normal blood chemistries at the end of the procedure, eventually obviating the need for performing blood chemical analysis during PISH."

The BioLogic-HDT system contained a plate dialyzer in which membrane expansion and compression mixed the sorbent suspension at the membrane surface. In the BioLogic-HDT system blood through the dialyzer was passive, created by positive pressure on the return limb of the blood circuit, and carrying blood back to the inflow limb where pressures were negative. Blood flow rates were 1500-2000 ml/min through the roller pump/heating circuit and 600-800 ml/min through the dialyzer. Blood flowing through the HDT portion returned to the inflow side of the roller pump, so there was some recirculation of treated blood through the dialysis system. Sorbent was circulated by alternating pressure in a reservoir on the outflow side of the dialyzer. The following diagram of the circuit was included in our 1996 IDE Application:

BioLogic-HT™ Circuit Schematic

Figure 44:
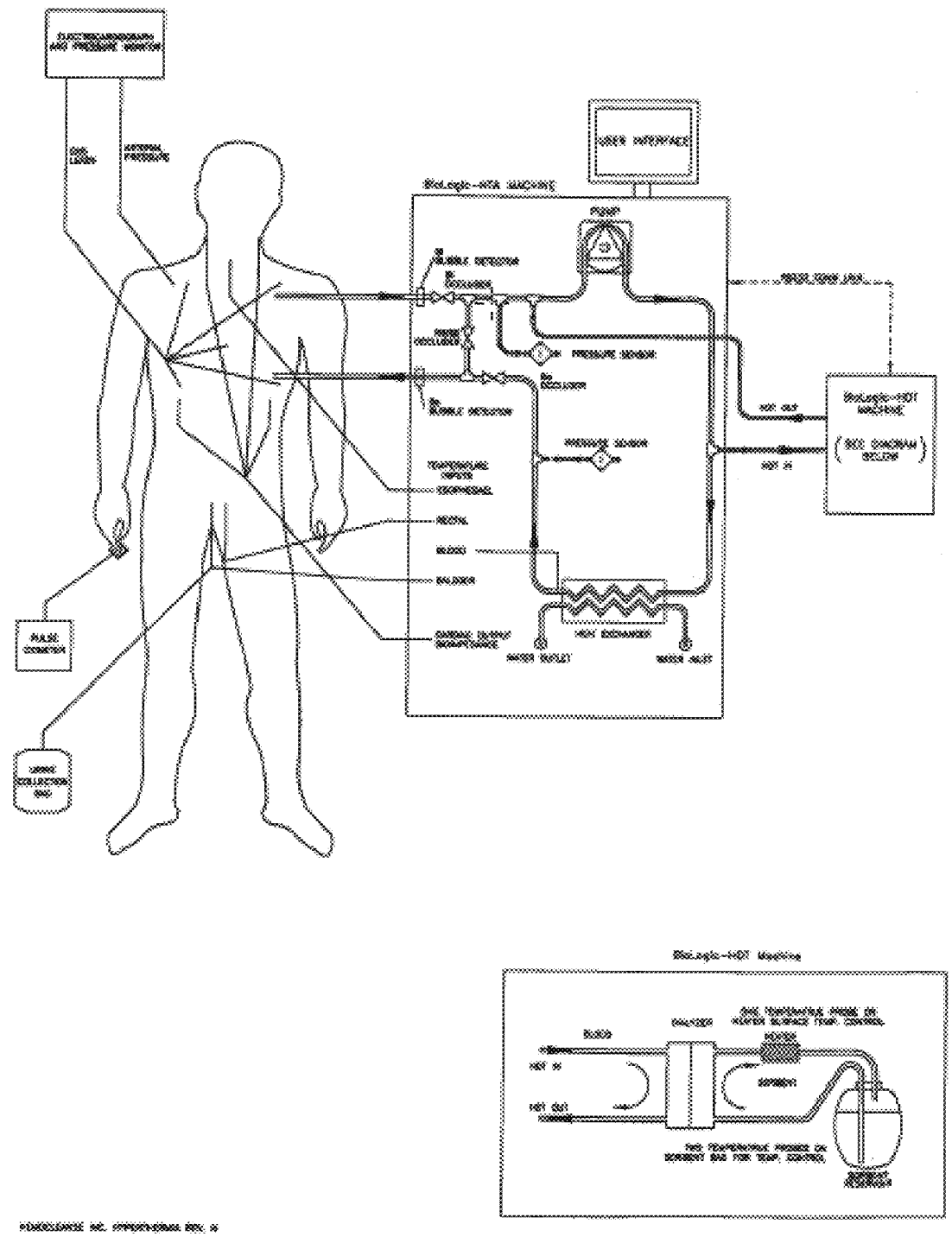
FIG. 44 BioLogic—HT Circuit Schematic

The BioLogic-HT Circuit is shown in FIG. 44.

Results of Clinical Trial with the BioLogic-HT System

Clinical trials of the BioLogic-HT system demonstrated that during PISH with this system there were minimal changes in calcium, magnesium, phosphate and serum bicarbonate. Further, the patients remained physiologically stable with modest fluid replacement, during the WBHT treatments.

After initiation of our clinical trials of the BioLogic-HT system in treatment of patients with cancer we received FDA approval to market the BioLogic-DT system for treatment of hepatic failure with coma or drug overdose. Initial marketing efforts of this treatment were highly successful, but wider market entry was limited by the need for a specialized machine for this therapy, requiring installation of a new machine and training at each hospital planning to treat patients with liver failure or drug overdose. Currently the BioLogic-DT system is no longer available through its manufacturer, and the plate dialyzer is no longer available. The BioLogic-DT system with some modifications was the device used in the BioLogic-HT System.

In terms of other prior art, another method for constraining powdered sorbents to allow perfusion is a "nanofiber" felt. If layers of nanofiber polymeric materials are bound to powdered sorbents and then either rolled up or layered, the fine powder particles are held motionless during perfusion. There are almost no fines released during perfusion and flow distribution is good. The downside is that there is a very low packing density. Only about 10% of the volume of the nanofiber felt layers is due to the sorbent particles. By comparison, the carbon block and filtration bed are each more than 80% by weight and 50% by volume of powdered sorbent.

Another technology we developed for powdered sorbent regeneration of biologic fluids was to create a bidirectional flow of plasma from blood through membranes, allowing the filtrate to contact powdered sorbents in a suspension transiently and then return to the blood. This application was implemented in the BioLogic-PF for plasma depuration, and also was shown to work with hemofiltration membranes (membranes which allow passage of mostly protein-free fluid). In summary, there are four methods for restraining fine particles. In summary, there are five ways to restrain powdered sorbent particles in order to perfuse them with fluid for effective depuration and regeneration: Nanofiber felt bed, Solid extruded block, Sorbent suspension passing through a flat-plate dialyzer, Bidirectional filtration across hollow fiber membranes into a sorbent suspension, and a filtration bed applied by hydraulic flow around a cylindrical filter. Of these five approaches, we have invented the last three.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A regeneration system for partial dialysate regeneration of dialysate in an extracorporeal blood treatment comprising:
   a housing comprising an interior volume and at least one inlet and at least one outlet;
   a carbon block positioned within the housing between the at least one inlet and the interior volume:
   a replaceable dialysate bag for removal of small charged toxins and replenishment of bicarbonate, wherein the removal of small and charged toxins and replenishment of bicarbonate is provided by changing the replaceable dialysate bag to supply the needed changes in body chemistry,
   a circulating fluid line system including fluid lines connecting each of the housing, the replaceable dialysate bag, and a dialyzer,
   wherein the carbon block comprises of active carbon sorbent, wherein the active carbon sorbent is porous and allows the dialysate to pass through it, wherein the pore structure of the carbon block has a short mean diffusion path length; and wherein the carbon block comprising a pulverized active carbon with a binder.

2. The regeneration system of claim 1, further comprising a dialysate pump which removes fluid from the dialyzer, and the dialysate pump or another pump pumps dialysate through the carbon block; wherein the flow of dialysate is in opposite direction of a blood flow.

3. The regeneration system of claim 1, wherein further comprising
   a separate infusion pump and infusate reservoir, to provide a continuous addition of substances to a patient,
   an effluent pump and reservoir", for continuous exchange of fluid wherein the fluid is dialysate, and
   wherein the flow of dialysate from the infusate reservoir to the effluent reservoir removes substances from the patient which are not removed by the carbon block.

4. The regeneration system of claim 3, wherein the substances that are not removed by the carbon block are small and charged toxins of kidney failure, wherein the small and charged toxins are selected from the group consisting of urea, phosphate, sodium, potassium, acid and combinations thereof.

5. The regeneration system of claim 3, Wherein the carbon block performs dialysate purification and regeneration.

6. The regeneration system of claim 3, further comprising a replaceable dialysate bag for the removal of substances which are not removed by the carbon block and for the replenishment of bicarbonate, wherein the removal of substances and replenishment of bicarbonate is provided by changing the replaceable dialysate bag to supply the needed changes in body chemistry.

7. The regeneration system of claim 3, Wherein the replaceable dialysate bag is connected to the carbon block through a bidirectional circuit.

8. The regeneration system of claim 1, wherein the nominal mean pore sizes of the carbon block are about 0.5 to 10 μm.

9. The regeneration system Of claim 1, wherein the mean diffusion path length is equal or shorter than 5 microns.

10. The regeneration system of claim 1, wherein the carbon block is a cylindrical hollow structure.

11. The regeneration system of claim 1, wherein the carbon block presents a hydraulic resistance equal or lower than 1 mm Hg per ml/min of fluid flow.

12. The regeneration system of claim 1, wherein the pulverized active carbon has a particle size of about 1 to 20 microns.

13. The regeneration system of claim 1, wherein the carbon block is made through the process comprising the steps of:
   mixing the pulverized active carbon with the binder, and
   extruding or processing the mixture into a hollow structure.

14. The regeneration system of claim 1, wherein the binder is polypropylene or polyethylene.

15. The regeneration system of claim 1, wherein the circulating fluid line system further comprises a housing-to-replaceable dialysate bag fluid line directly coupling the housing to the replaceable dialysate bag and wherein the circulating fluid line system further comprises a replaceable dialysate bag-to-dialyzer fluid line directly coupling the replaceable dialysate bag to the dialyzer.

16. The regeneration system of claim 15, further comprising at least one spike directly coupled to the housing-to-replaceable dialysate bag fluid line and the replaceable dialysate bag and directly coupled to the replaceable dialysate bag and the replaceable dialysate bag-to-dialyzer fluid line.

17. The regeneration system of claim 1, wherein the extracorporeal blood treatment is continuous veno-venous hemodialysis.

* * * * *